United States Patent
Yu et al.

(10) Patent No.: US 11,033,570 B2
(45) Date of Patent: Jun. 15, 2021

(54) MODULATION OF LNC05 EXPRESSION

(71) Applicants: Cold Spring Harbor Laboratory, Cold Spring Harbor, NY (US); Ionis Pharmaceuticals, Inc., Carlsbad, CA (US)

(72) Inventors: Allen Tingjin Yu, Pleasanton, CA (US); David L. Spector, Cold Spring Harbor, NY (US); Frank Rigo, Carlsbad, CA (US); Susan M. Freier, San Diego, CA (US); Jan Bergmann, Basel (CH); Carmen Berasain, Pamploma (ES)

(73) Assignees: Cold Spring Harbor Laboratory, Cold Spring Harbor, NY (US); Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/465,083

(22) PCT Filed: Dec. 1, 2017

(86) PCT No.: PCT/US2017/064306
§ 371 (c)(1),
(2) Date: May 29, 2019

(87) PCT Pub. No.: WO2018/102745
PCT Pub. Date: Jun. 7, 2018

(65) Prior Publication Data
US 2019/0343863 A1    Nov. 14, 2019

Related U.S. Application Data

(60) Provisional application No. 62/429,634, filed on Dec. 2, 2016.

(51) Int. Cl.
| | |
|---|---|
| *A61K 31/713* | (2006.01) |
| *C12N 15/113* | (2010.01) |
| *A61K 9/00* | (2006.01) |
| *A61K 31/7125* | (2006.01) |
| *A61K 45/06* | (2006.01) |

(52) U.S. Cl.
CPC .......... *A61K 31/713* (2013.01); *A61K 9/0019* (2013.01); *A61K 31/7125* (2013.01); *C12N 15/113* (2013.01); *A61K 45/06* (2013.01); *C12N 2310/11* (2013.01); *C12N 2310/113* (2013.01); *C12N 2310/315* (2013.01); *C12N 2310/321* (2013.01); *C12N 2310/3231* (2013.01); *C12N 2310/3341* (2013.01); *C12N 2310/341* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr. et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |

(Continued)

FOREIGN PATENT DOCUMENTS

| | | |
|---|---|---|
| WO | WO 1999/014226 A2 | 3/1999 |
| WO | WO 2000/063364 A2 | 10/2000 |

(Continued)

OTHER PUBLICATIONS

European Patent Office Extended Search Report for Application No. 17877203.4 dated Jun. 23, 2020 (5 pages).

(Continued)

*Primary Examiner* — Sean McGarry
(74) *Attorney, Agent, or Firm* — Michael Best & Friedrich LLP

(57) ABSTRACT

Provided herein are methods, compounds, and compositions for reducing expression of lnc05 in a cell or individual. Such methods, compounds, and compositions are useful to treat, prevent, delay, or ameliorate a cancer in an individual.

13 Claims, No Drawings

Specification includes a Sequence Listing.

(56) References Cited

U.S. PATENT DOCUMENTS

| | | |
|---|---|---|
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,811,534 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'o |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,670,461 B1 | 12/2003 | Wengel et al. |
| 6,673,661 B1 | 1/2004 | Liu et al. |
| 6,770,748 B2 | 8/2004 | Imanishi et al. |
| 6,794,499 B2 | 9/2004 | Wengel et al. |
| 6,906,182 B2 | 6/2005 | Ts'o et al. |
| 7,015,315 B1 | 3/2006 | Cook et al. |
| 7,034,133 B2 | 4/2006 | Wengel et al. |
| 7,053,207 B2 | 5/2006 | Wengel |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Seth et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Seth et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |

(56) References Cited

U.S. PATENT DOCUMENTS

| | | | |
|---|---|---|---|
| 9,290,760 | B2 | 3/2016 | Rajeev et al. |
| 2001/0053519 | A1 | 12/2001 | Fodor et al. |
| 2003/0082807 | A1 | 5/2003 | Wengel |
| 2003/0158403 | A1 | 8/2003 | Manoharan et al. |
| 2003/0175906 | A1 | 9/2003 | Manoharan et al. |
| 2003/0207841 | A1 | 11/2003 | Kaneko et al. |
| 2003/0224377 | A1 | 12/2003 | Wengel et al. |
| 2003/0228597 | A1 | 12/2003 | Cowsert et al. |
| 2004/0143114 | A1 | 7/2004 | Imanishi et al. |
| 2004/0171570 | A1 | 9/2004 | Allerson et al. |
| 2004/0192918 | A1 | 9/2004 | Imanishi et al. |
| 2005/0130923 | A1 | 6/2005 | Bhat et al. |
| 2006/0148740 | A1 | 7/2006 | Platenburg |
| 2007/0031844 | A1 | 2/2007 | Khvorova et al. |
| 2008/0039618 | A1 | 2/2008 | Allerson et al. |
| 2010/0190837 | A1 | 7/2010 | Migawa et al. |
| 2010/0197762 | A1 | 8/2010 | Swayze et al. |
| 2011/0123520 | A1 | 5/2011 | Manoharan et al. |
| 2013/0130378 | A1 | 5/2013 | Manoharan et al. |
| 2013/0203836 | A1 | 8/2013 | Rajeev et al. |
| 2014/0107330 | A1 | 4/2014 | Freier et al. |
| 2015/0018540 | A1 | 1/2015 | Prakash et al. |
| 2015/0184153 | A1 | 7/2015 | Freier et al. |
| 2015/0191727 | A1 | 7/2015 | Migawa et al. |
| 2015/0267195 | A1 | 9/2015 | Seth et al. |
| 2015/0275212 | A1 | 10/2015 | Alback et al. |

FOREIGN PATENT DOCUMENTS

| | | | |
|---|---|---|---|
| WO | WO 2004/106356 | A1 | 12/2004 |
| WO | WO 2007/134181 | A2 | 11/2007 |
| WO | WO 2008/101157 | A1 | 8/2008 |
| WO | WO 2011/133876 | A2 | 10/2011 |
| WO | WO 2015/106128 | A2 | 7/2015 |

OTHER PUBLICATIONS

Chen et al., "Progress and Prospects of Long Noncoding RNAs (lncRNAs) in Hepatocellular Carcinoma," Cellular Physiology and Biochemistry, Jan. 2015, 36(2):423-434.
International Search Report and Written Opinion for Application No. PCT/US2017/064306 dated Apr. 13, 2018 (10 pages).
Albaek et al., "Analogues of a Locked Nucleic Acid with Three-Carbon 2',4'-Linkages: Synthesis by Ring-Closing Metathesis and Influence on Nucleic Acid Duplex Stability and Structure," J. Org. Chem., 2006, 71(20):7731-7740.
Altschul et al., "Basic local alignment search tool," J. Mol. Biol., 1990, 215(3):403-410.
Bennett, "Pharmacological Properties of 2'-O-Methoxyethyl-Modified Oligonucleotides," Antisense Drug Technology, Second Edition, CRC Press (2008) Chapter 10, pp. 273-303.
Bergmann et al., "Regulation of the ESC transcriptome by nuclear long noncoding RNAs," Genome Research, 2015, 25(9):1336-1346.
Bhanot, "Development Antisense Drugs for Metabolic Diseases: A Novel Therapeutic Approach," Antisense Drug Technology, Second Edition, CRC Press (2008) Chapter 23, pp. 641-663.
Braasch et al., "Locked nucleic acid (LNA): fine-tuning the recognition of DNA and RNA," Chem. Biol., 2001, 8(1):1-7.
Braasch et al., "Novel Antisense and Peptide Nucleic Acid Strategies for Controlling gene Expression," Biochemistry, 2002, 41(14):4503-4510.
Branch et al., "A good antisense molecule is hard to find," TIBS (1998) 23:45-50.
Capaldi et al., "Manufacturing and Analytical Processes for 2'-O-(2-Methoxyethyl)-Modified Oligonucleotides," Antisense Drug Technology, Second Edition, CRC Press (2008) Chapter 14, pp. 401-434.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1, pp. 1-50.
Crooke et al., "Cardiovascular Therapeutic Applications," Antisense Drug Technology, Second Edition, CRC Press (2008) Chapter 22, pp. 601-639.
Crooke et al., "Mechanisms of Antisense Drug Action, an Introduction," Antisense Drug Technology, Second Edition, CRC Press (2008) Chapter 1, pp. 4-46.
De Fougerolles et al., "Discovery and Development of RNAi Therapeutics," Antisense Drug Technology, Second Edition, CRC Press (2008) Chapter 16, pp. 465-484.
Eckersley-Maslin et al., "Random Monoallelic Gene Expression Increases upon Embryonic Stem Cell Differentiation," Developmental Cell, 2014, 28(4):351-365.
Egli et al., "Synthesis, Improved Antisense Activity and Structural Rationale for the Divergent RNA Affinities of 3'-Fluoro Hexitol Nucleic Acid (FHNA and Ara-FHNA) Modified Oligonucleotides," J. Am. Chem. Soc., 2011, 133(41):16642-16649.
Elayadi et al., "Application of PNA and LNA oligomers to chemotherapy," Curr. Opinion Invens. Drugs, 2001, 2(4):558-561.
Englisch et al., "Chemically Modified Oligonucleotides as Probes and Inhibitors," Angewandte Chemie, International Edition, 1991, 30(6):613-629.
Freier et al., "Basic Principles of Antisense Drug Discovery," Antisense Drug Technology, Second Edition, CRC Press (2008) Chapter 5, pp. 117-141.
Freier et al., "The ups and downs of nucleic acid duplex stability: structure-stability studies on chemically-modified DNA:RNA duplexes," Nucleic Acids Research, 1997, 25(22):4429-4443.
Frieden et al., "Expanding the design horizon of antisense oligonucleotides with alpha-I-LNA," Nucleic Acids Research, 2003, 31(21):6365-6372.
Gautschi et al., "Activity of a Novel bcl-2/bcl-xL-Bispecific Antisense Oligonucleotide Against Tumor of Diverse Histologic Origins," J. Natl. Cancer Inst., 2001, 93(6):463-471.
Geary et al., "Pharmacokinetic/Pharmacodynamic Properties of Phosphorothioate 2'-O-(2-Methoxyethyl)-Modified Antisense Oligonucleotides in Animals and Man," Antisense Drug Technology, Second Edition, CRC Press (2008) Chapter 11, pp. 305-326.
GenBank Accession NR_040064.1, "*Homo sapiens* long intergenic non-protein coding RNA 862 (LINC008620), long non-coding RNA," 2016.
Gregory et al., "Inflammatory Diseases," Antisense Drug Technology, Second Edition, CRC Press (2008) Chapter 24, pp. 665-697.
Grillone et al., "Potential Therapeutic Application of Antisense Oligonucleotides in Ophtalmology," Antisense Drug Technology, Second Edition, CRC Press (2008) Chapter 21, pp. 585-600.
Hadaschik et al., "Antisense Oligonucleotides for the Treatment of Cancer," Antisense Drug Technology, Second Edition, CRC Press (2008) Chapter 25, pp. 699-720.
Hardee et al., "Routes and Formulations for Delivery of Antisense Oligonucleotides," Antisense Drug Technology, Second Edition, CRC Press (2008) Chapter 8, pp. 217-236.
Henry et al., "Toxicologic Properties of 2'-O-Methoxyethyl Chimeric Antisense Inhibitors in Animals and Man," Antisense Drug Technology, Second Edition, CRC Press (2008) Chapter 12, pp. 327-363.
Iversen, "Morpholinos," Antisense Drug Technology, Second Edition, CRC Press (2008) Chapter 20, pp. 565-582.
Koch et al., "Locked Nucleic Acid," Antisense Drug Technology, Second Edition, CRC Press (2008) Chapter 19, pp. 519-564.
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, 1998, 54(14):3607-3630.
Kumar et al., "Design, synthesis, biophysical and primer extension studies of novel acyclic butyl nucleic acid (BuNA)," Org. Biomol. Chem., 2013, 11:5853-5865.
Kumar et al., "The first analogues of LNA (Locked Nucleic Acids): Phosphorothioate-LNA and 2'-thio-LNA," Bioorg. Med. Chem. Lett., 1998, 8(16):2219-2222.

(56) References Cited

OTHER PUBLICATIONS

Kwoh, "An Overview of the Clinical Safety Experience of First- and-Second-Generation Antisense Oligonecleotides," Antisense Drug Technology, Second Edition, CRC Press (2008) Chapter 13, pp. 365-399.

Leumann, "DNA analogues: from supramolecular principles to biological properties," Bioorg. & Med. Chem., 2002, 10(4):841-854.

Levin et al., "Basic Principles of the Pharmacokinetics of Antisense Oligonucleotide Drugs," Antisense Drug Technology, Second Edition, CRC Press (2008) Chapter 7, pp. 183-215.

Lima et al., "The Rhase H Mechanism," Antisense Drug Technology, Second Edition, CRC Press (2008) Chapter 2, pp. 47-74.

MacLachlan, "Liposomal Formulations for Nucleic Acid Delivery," Antisense Drug Technology, Second Edition, CRC Press (2008) Chapter 9, pp. 237-270.

Maher et al., "Comparative hybrid arrest by tandem anti-sense oligodeoxyribonucleotides or oligodeoxyribonucleoside methylphosphonates in a cell-free system," Nuc. Acid. Res., 1988, 16:3341-3358.

Manoharan et al., "Utilizing Chemistry to Harness RNA Interference Pathways for Therapeutics: Chemically Modified siRNAs and Antagomirs," Antisense Drug Technology, Second Edition, CRC Press (2008) Chapter 15, 99. 437-464.

Monia et al., "Optimization of Second-Generation Antisense Drugs: Going Beyond Generation 2.0," Antisense Drug Technology, Second Edition, CRC Press (2008) Chapter 17, pp. 487-506.

New England Biolabs 1998/99 Catalog (cover page and pp. 121 and 284).

Nielsen, "Modulating Gene Function with Peptide Nucleic Acids (PNA)," Antisense Drug Technology, Second Edition, CRC Press (2008) Chapter 18, pp. 507-518.

Orum et al., "Locked nucleic acids: A promising molecular family for gene-function analysis and antisense drug development," Curr. Opinion Mol. Ther., 2001, 3:239-243.

Parkhomchuk et al., "Transcriptome Analysis by Strand-Specific Sequencing of Complementary DNA," Nucleic Acids Research, 2009, 37(18):e123.

Reynolds et al., "Rational siRNA design for RNA interference" Nature Biotechnology (2004) 22(3):326-330.

Sanghvi et al., "Carbohydrates: Synthetic Methods and Applications in Antisense Therapeutics, An Overview," Carbohydrate Modifications in Antisense Research, ACS Symposium Series, 1994, 22 pages.

Sanghvi, "Heterocyclic Base Modifications in Nucleic Acids and Their Applications in Antisense Oligonucleotides," Antisense Research and Applications, CRC Press, 1993, Chapter 15, pp. 273-288.

Sazani et al., "Splice Switching Oligonucleotides as Potential Therapeutics," Antisense Drug Technology, Second Edition, CRC Press (2008) Chapter 4, pp. 90-114.

Seth et al., "Short Antisense Oligonucleotides with Novel 2'-4' Conformationaly Restricted Nucleoside Analogues Show Improved Potency without Increased Toxicity in Animals," J. Med. Chem., 2009, 52(1):10-13.

Sigova et al., "Small RNA Silencing Pathways," Antisense Drug Technology, Second Edition, CRC Press (2008) Chapter 3, pp. 75-89.

Singh et al., "LNA (locked nucleic acids): synthesis and high-affinity nucleic acid recognition ," Chem. Commun., 1998, 4:455-456.

Singh et al., "Synthesis of 2'-Amino-LNA: A Novel Conformationally Restricted High-Affinity Oligonucleotide Analogue with a Handle," J. Org. Chem., 1998, 63(26):10035-10039.

Smith et al., "Comparison of biosequences," Adv. Appl. Math., 1981, 2(4):482-489.

Smith et al., "Targeting Neurological Disorders with Antisense Oligonucleotides," Antisense Drug Technology, Second Edition, CRC Press (2008) Chapter 26, pp. 721-745.

Srivastava et al., "Five- and Six-Membered Conformationally Locked 2',4'-Carbocyclic ribo-Thymidines: Synthesis, Structure, and Biochemical Studies," J. Am. Chem. Soc., 2007, 129(26):8362-8379.

Swayze et al., "The Medicinal Chemistry of Oligonucleotides," Antisense Drug Technology, Second Edition, CRC Press (2008) Chapter 6, pp. 143-182.

The Concise Encyclopedia of Polymer Science and Engineering, Kroschwitz, J.I., Ed., John Wiley & Sons, 1990, pp. 858-859.

The ENCODE Project Consortium, "An integrated encyclopedia of DNA elements in the human genome," Nature, 2012, 489(7414):57-74.

Vollmer et al., "Mechanisms and Therapeutic Applications of Immune Modulatory Oligodeoxynucleotide and Oligoribonucleotide Ligands for Troll-Like Receptors," Antisense Drug Technology, Second Edition, CRC Press (2008) Chapter 27, pp. 747-772.

Wahlestedt et al., "Potent and nontoxic antisense oligonucleotides containing locked nucleic acids," Proc. Natl. Acad. Sci. U. S. A., 2000, 97(10):5633-5638.

Wilson, "Aptamer Opportunities and Challenges," Antisense Drug Technology, Second Edition, CRC Press (2008) Chapter 28, pp. 773-799.

Woolf et al., "Specificity of antisense oligonucleotides in vivo," Proc. Natl. Acad. Sci. USA, 1992, 89:7305-7309.

Yu et al., "Probing the Role of a Highly Expressed Long Non Coding RNA in Hepatocellular Carcinoma," American Society of Cell Biology 2016 Annual Meeting Poster 343. Available on the internet Nov. 18, 2018.

Zhang et al., "PowerBLAST: a new network BLAST application for interactive or automated sequence analysis and annotation," Genome Res., 1997, 7(6):649-656.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties," J. Org. Chem., 2009, 74(1):118-134.

Li et al., "Progress and Prospects of Long Noncoding RNAs (lncRNAs) in Hepatocellular Carcinoma", Cell. Physiol. Biochem., 36: 423-434 (2015).

SEQUENCE LISTING

<160> NUMBER OF SEQ ID NOS: 9

<210> SEQ ID NO 1
<211> LENGTH: 1445

<212> TYPE: DNA
<213> ORGANISM: Homo sapiens

<400> SEQUENCE: 1

```
tgatgaattt gtgtgtgttg tggctgatgt gcattttggt gctttgtatg caagtttaag      60
aatatcttag caataggaaa ggaagattta tggcagttta attaatgaat ataatgaagg     120
ctaaaacttg tagataaatt tataaggtgc ttaagagctc ttcaatttgt taatggaaag     180
aaacaccatt tacaccggat ggctacaaag caaccttatt ctgagagaga ggatctcatt     240
ctgtcaccca ggctggagtg catgatcata gctcactgca gcctcgacct cctgggctca     300
agtgatcctc ctgctccagc ctctcaagta gctaggacta cagatctttt ctcagaatag     360
cagtctgtag gctgtcacct aaagtgtcct gttttcagtg ctgcacctgc tctgagcttc     420
atctttttac gaagacgtca tggtgtgcta tctgtactgg gaaactttcc ccagcatcag     480
ccatctcctg aagataacat tgtctgctag agattgtcat gtatgtggat tgaatctctt     540
tatcttcatg gatccagttg aaaatcaggc attgcatcca gttatcatgg ctttaatctt     600
aatgccttcc ctgcactgtt tgggaatat cttaatactg ctattttga agagtccagc       660
tcagttattc tgcagaatgt ctgttgattt ggctttgctg tttcctcata agtagatcca     720
gattatacgt ttttgttgat gttgggttct tctcagtgaa tcacatccga tgatgtcagc     780
acgaggcctg atcatttggt ttaggtagct ttcactagac tttttcattg taaaggtacc     840
tatccctttt ctaattaata agtaatatgt tgggtgatag tttgtgtgtg aatatccttt     900
tctccagtga cctttcatcc aatggtttca gcattttaaa tgatcctggg ctgagtcagt     960
tttcagtggt ggctgcagac ttgtggtttt ccaattcttt catcacttt acatttatta    1020
attggcagtc tatgacttct tatagccaca taaagataat tcaggaatta tctgaaccta    1080
tgaatgttac cttatttgga aaaagagtct ttgcagatac aattcaatta agaatcttga    1140
gatgaggaga ttatcctgga ttatccaatg ggccctaaat ccaatgacaa atgtccttgg    1200
cagagggaga tttgagacag gagaagagaa gacacgaagg agggaaggaa gtgatgtgac    1260
cacagaggca gcgattggag tgatgtagtc acaagccaag gagcaccaac agccaccagg    1320
agctggaaga gcccaagagt atatactaat acctggattt gggacttggg acttctggtc    1380
tctagaagta ggaaagaata acatctgtt ttttgttaaa aaaaaaaaaa aaaaaaaaa     1440
aaaaa                                                                1445
```

<210> SEQ ID NO 2
<211> LENGTH: 1417
<212> TYPE: DNA
<213> ORGANISM: Homo sapiens

<400> SEQUENCE: 2

```
tgatgaattt gtgtgtgttg tggctgatgt gcattttggt gctttgtatg caagtttaag      60
aatatcttag caataggaaa ggaagattta tggcagttta attaatgaat ataatgaagg     120
ctaaaacttg tagataaatt tataaggtgc ttaagagctc ttcaatttgt taatggaaag     180
aaacaccatt tacaccggat ggctacaaag caaccttatt ctgagagaga ggatctcatt     240
ctgtcaccca ggctggagtg catgatcata gctcactgca gcctcgacct cctgggctca     300
agtgatcctc ctgctccagc ctctcaagta gctaggacta cagatctttt ctcagaatag     360
cagtctgtag gctgtcacct aaagtgtcct gttttcagtg ctgcacctgc tctgagcttc     420
atctttttac gaagacgtca tggtgtgcta tctgtactgg gaaactttcc ccagcatcag     480
```

```
ccatctcctg aagataacat tgtctgctag agattgtcat gtatgtggat tgaatctctt      540
tatcttcatg gatccagttg aaaatcaggc attgcatcca gttatcatgg ctttaatctt      600
aatgccttcc ctgcactgtt ttgggaatat cttaatactg ctatttttga agagtccagc      660
tcagttattc tgcagaatgt ctgttgattt ggctttgctg tttcctcata agtagatcca      720
gattatacgt ttttgttgat gttgggttct tctcagtgaa tcacatccga tgatgtcagc      780
acgaggcctg atcatttggt ttaggtagct ttcactagac ttttcattg taaaggtacc       840 tatccctttt ctaattaata agtaatatgt tgggtgatag tttgtgtgtg aatatccttt      900
tctccagtga cctttcatcc aatggtttca gcattttaaa tgatcctggg ctgagtcagt      960
tttcagtggt ggctgcagac ttgtggtttt ccaattcttt catcacttt acatttatta      1020 attggcagtc tatgacttct tatagccaca taaagataat tcaggaatta tctgaaccta     1080
tgaatgttac cttatttgga aaaagagtct ttgcagatac aattcaatta agaatcttga     1140
gatgaggaga ttatcctgga ttatccaatg ggccctaaat ccaatgacaa atgtccttgg     1200
cagagggaga tttgagacag gagaagagaa gacacgaagg agggaaggaa gtgatgtgac     1260
cacagaggca gcgattggag tgatgtagtc acaagccaag gagcaccaac agccaccagg     1320
agctggaaga gcccaagagt atatactaat acctggatt gggacttggg acttctggtc     1380
tctagaagta ggaaagaata aacatctgtt ttttgtt                             1417

<210> SEQ ID NO 3
<211> LENGTH: 31249
<212> TYPE: DNA
<213> ORGANISM: Homo sapiens

<400> SEQUENCE: 3
tgatgaattt gtgtgtgttg tggctgatgt gcattttggt gctttgtatg caagtttaag       60
aatatcttag caataggaaa ggaagattta tggcagttta attaatgaat ataatgaagg      120
ctaaaacttg tagataaatt tataaggtac acaattattt ttatagctta ttttagcac       180 aaaggtgatt gtattttgtt gctttaagaa aggacctctt gataatactg gcgtgttta       240 tatttcaatg tgaccagttt aactgatatg caaacaatta ttttttaagg gaaataaat       300 gaggcagtag tacaacttag cgaagaggac actgtggcag attctaacga ctagattaaa      360
tttgagctct tatttggctt ttactaccaa ctgactgcat aactttgggt cagttatttg      420 gctcttttt ttttttaatt tacaaaatta gaatgagaac tacagatagt gaaaatattt       480
ggaaaagctt tttgaagtcc cacgtgaaag gcatcagaaa aaagagttgg gtgattttt       540 ttaatgggaa ataatctgat attgtcagta aacctaaatt ttttgtatat taatttattt      600
tttaagctgt tatttaattt caggtgctta agagctcttc aatttgttaa tggaaagaaa      660
caccatttac accggatggc tacaaagcaa ccttattctg gtaaaataat ctcttaaatc      720
cttatataca cagtcactaa ctgttggctt tataaggtca gtagtagcaa acagccctg       780 tggcagttag aagctcagca tgtccaagat agcactaacg gggaacaaac acaaaaaaca      840
gcaaacagtt taaacagtac catttgattt gaatttaacc caatcttaaa cagaggactc      900
taaaaaaaca attccagca aagttacatt aattagggag atcattaggt tgtatcaatg       960
cagtttagct atgccttta aaaagtgaag atggactaga agcggtggct catacctgta     1020
atttcagcac tttgggaggc caaggtggga ggatcccttg aactcaggac tttgagacca    1080
acttgggcaa caaagtgaga ccatcatgtc tacaaaattt taaaaattag ctgggtgtgg    1140
tggggtatgc ctgtggtccc aactatttgg aaggctgaag caggaggatc gcttgagccc    1200
```

```
aggaggtcaa ggctgcagta agccatgatt gtgctactgc actccaacct gggcaactga    1260
gtgagaccct gtctcaaaaa aagaaaaag attgaacttg caggccaaca tttatttctg     1320
actattgact acttttgaaa gagaaagctt tggacactaa cattctagtc tcagaggcct    1380
caaagaagca cagccctgta aagaagaaaa ttctgctggg attagcaaga gcctcaaggt    1440
tttgggaact tggaatgcca ggctcagtgt tccgagttcc aatgttgact ctgcctgtga    1500
gtcaccctga actagtcact cagtctcttg tgtttccccc tttagagaag agctaagact    1560
attgactttt caggagttgc aaaacatgtt acaaaggat aggaaagtac tatgcaaaca     1620
tgtaaatatc atgaaatatt ggggggtac attttaataa agataagctg cattcttctg     1680
ataattggaa gttgataatc tttatgtaaa gacagggaga ttgatttcaa aatagaggtt    1740
aatgcttgaa attttaattc gaacagtgta aatttggatc attgtttgct ctgttagtcg    1800
atgttgctta ctgaaaggaa actcttaaca agttgtctta ctagaatggc ttattttcag    1860
agtcagaccc ccaggctttc tagaaatgtg tattaaaatt tagtaacctc actttcaatt    1920
gttgagtata ggacactgtg gttgggtttc tatatatgtt gtaaacaagc caaatacaca    1980
aagtgaactc tctatggacc ttaaaaaagt cttaaaaatt ttttttttgag gatattgaat   2040 gaggcaccta ttttattcct tacttttgca ggatagcttg tcagtgccag cttgggtttt    2100
tgaattctga ctttttgctg gccatgattt ggctgtctca ttaataagac aaacctttct    2160
aaagtggagc tcattgtttt ttagttcttt taatggtgtg gctagcctct cattgttaaa    2220
gaaaagaaag aatataattt ttattcttcg ttctttctgg caactttata ccctctacta    2280
acccacccag tcctgaaatc ctgttagttt ttccatctgt gactagcatc tctcttctga    2340
ttcccagtaa acgctactat attcccatca ttcaaaatta caactgttaa ttattttgt     2400 catatcttct tcaatttttt taaagaaata aaacaaaaca ttgatgataa aatcaagttg    2460
cctttgaata ttaattccaa gtccattttcc tccttctgtc ctcacttccc agagcccatg   2520
ttcagtttgt actttttta atttttata tatatttgta tgtacccata gttaatatgt      2580
agtattgttt tatggattta aatatacata aatgttttct tttttagaga gagaggatct    2640
cattctgtca cccaggctgg agtgcatgat catagctcac tgcagcctcg acctcctggg    2700
ctcaagtgat cctcctgctc cagcctctca agtagctagg actacaggtt gtgccacta    2760 tgcttggcta atttttttt ttttttgta gagatgggat cttacaatgt tgcctggtct     2820
caaactcctg gcctcaagag atcctcccgc ctctgcttcc caaaatgcta ggattacaag    2880
tatgaaccac catgcccagc caactgttat atgatttgtt tactttctct gagcattgtt    2940
tttaaggtct agccatgttt ttgtacagac acacacacac gtgcacacac acacacaccc    3000
atctatatat atatattcat tatttttaat tgctgtctag catttctttt ctttcttttt    3060
cttttttttt tttttgagaa agactctcgc tctgtcaccc agactggagt gcagtggcac    3120
gatctcagct cactgcaacc tctgcctccc gggttcaagc aattcttctg cctcagcctc    3180
ccaagtagct gggactacag gcgcctgcca ccaagcccgg ctaattttg tattttagt      3240 agagacgggg tttcaacata ttggccagtc tggtctcaaa ctcccgacct caggtgatct    3300
gcccgccttg gcctcccaaa gtgctgggat tataggcatg agccaccaca cccggctatt    3360
tgctgtctag catttcatgg cataaataat accacatttt atcagtccat ttattagtga    3420
atatatgatt gtttatattt ttttcactaa tatataggca atagtttctt agtcttgatt    3480
cctagatgca ggattgctac attttgaata tgcacaattt aacttttaag agatattacc    3540
```

```
aaattgattt tcaactgttg gaaaactgtt tccccagata ctttccaaca cttgtcagac    3600
ttcttaatct ttgccaattt tagggggtaac aaatggtttt ccctgggctt tctagcttta   3660
tttcagttca tcctattcat agttgctggc ctaatccttt ctaaggacag cactgctcag    3720
ggccttgcct ggtcaaacac tctcagaagc tctgcactat ctactcagtc caaactgccc    3780
caagtcctct gcaagcaacc tgtcccacct catctatcca tgcccagctg gaccagaacg    3840
tgcaacttac cactttctca aactcagctt ttacttttct gcctctgcaa cttgatcatg    3900
ctcttctgca ttcctgtatt gattcaacaa atatttattg agctctttac ttcctgccag    3960
gtgctgggaa tataagggtg aaaaagaaag accatatcta ggcatttatg ggacttaaca    4020
attttagca gaggatgggg atgggcagaa ataatccag taaaaaaatt gagcacgata      4080
attttccata gtactttata agtactataa agaaagtaaa atagaatgtt aatgagtttg    4140
tgtggaggag tgacgggggt ggatgtgggg catgtccagg tgggaacttt agaggggcag    4200
gtgctcagcg aaggctttac agagaaggtt atattcccct tgagaccagc agtgtgaagc    4260
tcattcacag accagaagta tttctgatcc tgagcaagtg cagatccctg catgtagggg    4320
tggcctcaga ggatcctgag aggagcagag ctgcccttgt ggctggcagt tggggctagg    4380
agagtggtgg atgctgtagg agacaaaggc aggcaaagcc atgcctctca gggccttgtg    4440
gatgctctct accaaagcca ctgcaggaaa ccgtagtttg ccctttaaag ccctgtaaag    4500
ccgtgatcaa atcctctctt cataatcatt cctgatccag ctggctgggc gcgctctttc    4560
tggaccacca ttgcacagta gtggtgcctc ttaaggcatt taacatagca ctttgggatc    4620
atgatgtctg tccttcccat gagctattag aatttgtttt catgttgctg ttttgtttct    4680
acctcacaag ggacaatact ttattgtctg gaaagaggaa agtagaggag gaaaaggtag    4740
aacacagaag aagcctgtca ttttttattg agtctggaat gaactgagtt tcagtgaaat    4800
aagctttcct gttgtatatt tgagctgatt ttcacaatgg caaatatgac aaatttaatt    4860
ttccttaaaa attgataaga ccagttggag ttctaaaagt gatttttttct accccttgaa   4920
gatcttttct cagaatagca gtctgtaggc tgtcacctaa agtgtcctgt tttcagtgct    4980
gcacctgctc tgagcttcat cttttttacga agacgtcatg gtgtgctatc tgtactggga   5040
aactttcccc agcatcagcc atctcctgaa gataacattg tctgctagag attgtcatgt    5100
atgtggattt aatctcttta tcttcatggt aagtttggag ttgtgtatta gacctacctt    5160
actggtgaaa agaatgaagg ttcgtagagg tcattacttg tctgtccgca ggttacgaaa    5220
ttagagaata gcgaagctga cacttgaatc tggggctact gaccaattct ctatgaagct    5280
tccacacttt aagtagtaac atagcaaaga ccaagcactt aaaattattt ctagatgaag    5340
cctttgtgct ctgaaccact gtgatcactg ttgatcgcat tttccttctt gaactcattt    5400
tctattaata ggagcattta tcacagacag tgagaggcag tttgtgcagc ggggaagagc    5460
acgggctgtc tgaagctaga ctgtctgagt cagggtcttc tgtgccagct tgctagctgt    5520
gtggggaag ttacttaaca tttctgtggt taagtttcct tatttttagt atgaggataa     5580
taacagcacc tacctcattg ggttgttgta aggattaaat aggataatgt acttaaaagg    5640
cttagaacag agccttgtac ttaataagtc ctcagttaat gctctcctag tctcaggtct    5700
cagctcaaat gtcctctcct agggaggcct tacctggccc ctgtagctag cctgggcctc    5760
ccccaggcat tcaacatctt caccctctgc ctgcaccctg cctacttccc tcatggtgtt    5820
ttccctcttt tgggggtacca ggtttattac agggttgtct cctctgtgac aatgtgagct   5880
ttccatgggt tggcttgtat gttccagttt ccagctccag gacagtgcct ggcatgtagt    5940
```

```
ttgctctcaa tgtacatttg tttaacggct ctctgtttct gaaaatcctg aatcagagct      6000
ttcattttga acaaaatcgt tgctactctg gtttcttctc aatatgccat atgtattagt      6060
gttccctgaa acttcattcc cacagcttca gacatgatcc caaatggctc aagaatttgt      6120
acttctagcc ctgactcctc tttctttact tttttttttg agacagagtc tcactctgtc      6180
gcctgggctg gagtacagtg gcgcgatctt ggctcactgc aacctctgcc tcccaggttc      6240
aggcaattct cctgccgcag cctcccaagt agctgggatt acaggcgccc gccactatgc      6300
ccagctaatt ttttgtattt ttagtagtga tggggtttca ccatgttggc caggctggtc      6360
ttgaactcct gacctcatga ttcgaccacc tcggcctccc aaagttctgg gattacaggt      6420
gtgagccacc aagcccggcc ctgactcctc tttcaatctg tatttccaac taactgttca      6480
taaaacaaat tctggtaggt gtccttagca caacatgttc aaaaccaaat gcactacttt      6540
tttttttttt tttctaaacc aggtcctctt tctgtgcccc cagcccggtt gacaatgtgt      6600
gccttcactc acccaattag aaaccttgga ggtatcctgt actcttctgt cacttaccct      6660
cagcctaaag ccaatcagtc accaaagtat tgtctgtcat tatcatcatc atcatcatca      6720
tcactgtcac cactgatgga gtgagaacct tgtgcagttg agcatgaacc ccaatttcat      6780
ttgcaaaatg acccagacag cagatttcat ctcatatgaa ataagcaagg tgaggttttg      6840
atgacgttac agacatggct aagaagaggt tgagaaccag cattcagccc acctgactcc      6900
aaagctcatg ccccgaacct cagaaacttc tccagtgagt tcctttttt taatggcagg      6960 atcacaccat tagtttggac tggatccaac ctggattgtt gcaacagcct ttgatctgat      7020
ctgtcaagcc ctgtgccttc tgtgcaaccc attctctacc ctggcacgag cattactaaa      7080
ataccaatct ggtcctatga ctcctctgca taaaaaccac ggctggggct ggtcaagtgc      7140
aacagtgttt acaactaatt gatcacaacc agttacagat atctttgttc cttctttagc      7200
caaaaacaaa cagaaaaaca aacaaaaccc aaataacaaa aacaaacaca aaaaaccccc      7260
cattgtttgt tccctttttgc atcttttgaa ttctaaactc ctcacatagc ataaaatccc      7320
cttctgggtc ttttcccagc ctacaaccca cttcccacc tgccccattc ccctgttgc      7380 tcctacctct ggccttactt cagccccagg gtccctgct ggacatggca ggcccagcac      7440
atgctgccct gggcccttc actttgcttt gtgacatatt tttcatcctt caaccttcag      7500
ctcataagcc atattctctg tgaaggcatc cagagggccc gagacagccc ctcccacctg      7560
tgttcctcag agcattctgt gcccataatt agggtgaaca catttctgaa tcagcagtgg      7620
aaatgtttca gttcagacag ttacgcatgt gcccctgaag gcaatgggac agttaataga      7680
gcaaagtcca gaagaaactc ttggagatga ttcctcttta tctgtctgct accctgtaga      7740
ggggtgggga aggtacttcc agggtagaga gctgtgggtg gcccttgtat ctcttggaga      7800
tgattcctct ttgtctgtct gctaccctgt agaggggtgg ggaaggtact tccagggtag      7860
agagctgtgg gtggtccttg tatttgccca cacctgacac gatgcctaac tgttgtttgc      7920
tgaatgtatg aagactatgc caggcctgag attcttttga acataaccaa atgtcatgtg      7980
taaatttctc caaataacca accaacaaac ccagctcttt ataacaatgg acaatccagc      8040
atgagtatta ggactctgtt taagtctcag gtttatcact agaacaattc tcatagacac      8100
acttcttcat ctgtaaaatg gggataatag tagctactta cgggagttgc agtgaagact      8160
ctgtgaatga attgaaggaa attagcaggc acagagtctg gcaaagaagt ctttgtttca      8220
ggcacaaaga tatgtgtagc tcatcactat aaacaggaac tagaaggcaa ggtcatgttc      8280
```

-continued

```
tagaataact tttaaaagtt aggatattgt tgggaatttt aaaaggtaag acaattaaaa      8340
atatgactaa tatttgtcag cttttttttt tttttttttt gatacagagt cttgctcttt      8400
tacccaggct ggagtgaagt ggcgccatct cagctcatta cagcctctgc ctcccgggtt      8460
taagcgattc tccctcctca gccttcttga gtagctggga ttacaggcac ccgccatcat      8520
gcccggctaa ttttttgtatt tttagtagag actggggttc accgtgttgt tcaggctggt      8580
cttgaactcc tgacctcaag tgatccaccc acctcgacct cccaaagtgc tgggattaca      8640
ggcttgagcc actgcgcctg gcctcatttg ttagctttaa catatgaaga gacatcctcc      8700
taaatgttaa agtactcttt gacattttac ctatgcattt tacagttggg ctgggagaga      8760
tgtgactccc ggtttgtttt gcctcacctt tgcatttcat cagctgtgtc tgatcccagc      8820
ctagcctgtg tgtcggaatc acttggatga gtgttttaca gactcctggg ctctacccca      8880
aacccactga atcagaatgg ggacaggaag ggaactgtaa atctacattt atgaaaacct      8940 cccctgtgg ttttgatagt ctgcaaggtt tgggaatcac tagttcccaa acacaccagt       9000
agaaaagcat atagtaatta acattctcaa tttctcagct ttacagtgtt tgtaattaaa      9060 aattttatt tgcttttttg taagcaatat tagctttctc aatgtctgtt tcaccttcac        9120
tgcagtctgt ttatccagcc tgggaaaaaa actggctcca cttaaacaat gagacaaaaa      9180
aggtgcaaac ctgacagctt ccctaccttt tttgcattag cgtgtaggta tttcctccat      9240
gtcctaccag ggccatttaa atgctaatat agttaagtac aacaatcttt ttagcaatca      9300
gatggaattg tttttttacca caatcttatt tctcatttct ccagtccgta ctttttcctttt   9360 tttgggggcag ggtgggggta gggctagagg ggcatacatt taaattcttt gacctttcaa     9420
accttaacaa aaattctctc ctaatatctt ctcagcagtt cttgcaatgt gtgtatcctc      9480
taaacctgag ctctgtaatt tgaatgtgct gagtcacctt gtctttgcag ggtcaaacat      9540
tttgcatcca ggaaaagtac tgcagaaaat cacaccatta gcagctagct ggtatgttat      9600
ttgaatattt gaatacaaat aggaagactg gaaaggagaa agttactgtg tacatagata      9660
catagtaact tacatatact taaaacaacc ttttttttttt ttctaatagt ctgctaagtc     9720
ctctttctga ttgatgactt ttttgtgtgt gaaattctct aaatatttat ttgtgttcct      9780
agaaagtgaa aatgaatata aatggtaaag cagttgcctt gcaatgttta ataaaaggag      9840
aaaatagtct ttgctattat actgaagctt tgcataatta agattcttga attaattta       9900 aagaattaat aacaaaaaaa tacaatcatg aaccagatat tgagagttaa tgtctaattt      9960
aagttcaact tttagggagt ccgttttcct atttttgatca tgtagttgaa tagacagtga     10020
ggagatgtta ctacaactgt attaatagag gaagtggcag gaagctacag tttccttaga     10080
atcagaaaga aagtttatag aactcactgg aaatgagggt tatagataaa gattgaagta     10140
ggataacctt ctatttagaa ttgctattgt atttttgtaa cataagagtg gttttctttta    10200 aagtaagtat ttgggggctaa agagaatgcc aacactccac tcacagggaa gtcggaaagc    10260
ttaccagtat taacaaacat ccgaagtcat ttcacaaggt ggaagtttac tatagaacca    10320
gtaaacataa tcttcctcca gggtgttttg agtcatgaat ggggagcaac ttgctccctt    10380
cgtggatgga gcactgggga caagcttctc tgcatcagag cctgtgaaat atcaatagca    10440
acagctactg tactctgagt gctcacttcc tctatgccag aggctggctc tggtctttaa    10500
ttgaattcgc tcactataca gcccctata cagaaggaac gctaattttc aatacctaa      10560 agaggccaaa tcattcccac agcattagtg gcagagggg tatttgaacc caggcagaat     10620
gactcgaact ccctggtaat tagccatggt ggagaatgtc tcccagctca caaaaatgac    10680
```

```
tactcactgg caagtaacac taagtacaga aagaatgtca tcagttggtt ggtgttcttg   10740
ctttctctcc gtgaacaatt aagagggcgc agaggtgaga tggggtgggg tgggataaag   10800
ggaaggcctg gaagaaggga cagaagggct gcaaataatc acccgggagc ccagtgagac   10860
tcagagaaag attctaacct aaaatactct tctgctgtca gctattctgt aattaacatc   10920
cacagatgaa aacatgaagt gtattaaaaa tcctttgtgt ttttttttcaa ttttgactga   10980 tggacataat ataatgactt gataattaaa aaaaagaaa gaaagaaaac ccacaaaacc   11040
caacaaccca aaattctaaa ctaactgctt ttcatcattc tactccctga ttagacatgg   11100
aattgggctc gttactacgg gtagaacaat ggcctgtgtt gggcaggaca agggcatgga   11160
agctctccag caagcagcac agtgggacag cacaggcttc tagcaggcat ggtttcagtc   11220
tcaattgttt acaagccttg ggatctggaa caattgattt gagccctaca acattagaat   11280
ggttcctttt ctcagggcct aatatggggt cagagaaggc actcagcaag gagggttttt   11340
tcagaggccc aggaagaact agttcagagg ccgagcctcc tggagaaaca cgtagatgag   11400
tggggtcagg tgcctgtgtc tgagatctag ctcaggtcag ggcagttttc attgagaagg   11460
tgacatttga acaaagattt gaagttgctg agtgagttag ccatgtggga atctcaatag   11520
aagagatttc caagcagagg aaacaactaa ggagaaacag gaaattgcct tctggcaaga   11580
tgtaggaaca gcaaggaagt aagtgtggct gaaacagagt gagtgagggg taaagtagtt   11640
gaaagtgagg tcgggagta agagagtcag actggccagc atcattttaa ggactctgag   11700
ttttaactat gagaggaaca tggagccatt gcaaagttct gagcagagga ggacatgtga   11760
ctgagagttt aaaaagatgg ctctaagcca ggtgcaatgg ctcatgcctg taatcccagc   11820
actctgggag gccgaggcag gaggatcact tgaggccagg agtttgagac cagcctggac   11880
aacatagcct gacctcatct ccactaaaaa agaaataaag ctgggtatgc tggttgcgta   11940
cctgtagtcc cagctactca ggaggctgag gtgggaggat cacttgagcc tgggaagttg   12000
agggtgcact gagtcatgat catgccactg tactccagcc tgggcaacag agcaagaccc   12060
tgtctcaaaa acaacagcaa caacaaaaat ctaaaacgat tgctctgatt gctatattca   12120
gaatagactg ggtttgaagc agaaagacca gttaggagcc attgagtaat ccagacaaga   12180
gatgatgatg ggtctgacca gggttcataa cagtatgagg gtgagaagtg ggcagattct   12240
ggatctatgt tgaaggtaaa accaacagga tttatccctg ggttggatat ggaatgtgag   12300
tggaaaagag aacgtgagga tttattccag ggcttatggc atgagcaact ggaaggatgg   12360
cattgccaat acctggggtg gcaaggatat gcagaggaaa cagatttggg gggaacacca   12420
agggttcatt tttgcccatg ttgagtgtga gatgtccact tgatatccaa gtggagatca   12480 aatgaggag agaaagggt ctggtctggt gatacgcttt tagaaattac cagtatataa   12540
atatttaaag cccagagaca aagagatcat aaagggagta ctgacagaga agagaaggga   12600
tcagcagact gagctttgag gtgctacaat aactgagagt tctagaaaaa gaggagggag   12660
ccccagaggg gacttgaaat ggagcaacaa atgaggctgt cttgaagatg gcattcacca   12720
ggcagagagt agggaaagaa ttctaggtga ggggaagggt gggtacccag actcagaggt   12780
acaaaagcct gatctgggag agggacgggg aagatagtaa gtggtgtggt atggggaaga   12840
gtagagtaga ggctgcaaga tgggcttctt tgacatgtaa gggacttgga ccttcaatgg   12900
aagactttgg gagttaattt cttgataatt atgaggaagt tgatggcagc taagactcat   12960
tgacgtatta ttctaactta ttattctagc atgtgtcaag cactgtgcta agcaaattac   13020
```

-continued

```
atacattatc tcacttaatc tttacaccta ccctttaaga aagatagtag tattatcctc   13080
tgcagatgaa gaaatgggct caggggtca aagttatcag tgagtaaact gcctttaacc    13140
caggtagttc cattccagag tccatccttt taaccactaa cctgtcctgt ctccttgagg   13200
tctggcactt cttaaccagg tctcagaggg tcagcctgag agcatgtgtc atttccccat   13260
agaggacctg acttcactgt ttctcagatg aggtgcttta cctgcaaagg gttaaggtag   13320
attctgggca ccagtgaagg agttcaagtg gaggagcaac ttgacaggat ttgcttgtgt   13380
aggatgttga tctggcagca gtgtggtgaa cagagtgcat gagggtgcct gctagtaagg   13440
gagatctatt tggggaagat tagctcaatg tgagacctat tgaggggcct gagggctgat   13500
gaagcagtgt gcttcaggct gcagggtcag ggtcttagta agagatgagc tagatttgag   13560
agtcacgtgg ctgcaaatag aatcagtggt tctgagggag ggaagcaatt ttcagatatt   13620
cactgtccat atatacacac ttttctcaaa tggatcccct agagaacagg gaaaatgcac   13680
acctcttgca cttccatcat cttcctatgt tgtgtttggg aaggtaaaaa aaaacctccg   13740
ggacccaaac ctaggtccaa tttcaaatat aatgcatgta ggagaatgtg aatgactcag   13800
ggccagtgac acttccttt acaagtcaga tgagtctggc tgttcgcttt caacatactt    13860
gaagggagac ctaaacacac acacacacac acacacacac acacacacag acacacacac   13920
tctttagaga tagggtctta ccatgttgcc caggctggag tgcagtggct gttcacaggt   13980
gtgatcatag tacactacag cctggaactt caagtggtcc tcccacctca gcctcaaagg   14040
gtgtgggatt acagttgcac accactgtgc ctggctgaac ataaggatag attacaacgt   14100
gatttggggc tatgactttc aaggatttca aagatttgag tgacattgct gtagctaaaa   14160
tacttccatt cttttatta tttaaaaata atttctcagt tattgtatct ataaaaagaa    14220
cagtagtgat ataattatac caatggtttc attataataa taagtcatcc acaaacccat   14280
taactaataa taggaaaata aacccagttc atcgcattaa tctcattaaa gaatgtattt   14340
ccaataaaac tttatattga atgattgtca aagtttataa tatacttatg atgtttgat    14400 taattgtgta ctatgaataa ctggaattta ctactactta atccagagga attttcttt    14460 gtctacctag aggattatgg tcacaatttt tttttttctat tttaaatctt aatttatgtc   14520
catagttttg tggatgagat ctatgaatgg gttattaata aaaggttttt gtttgtttgt    14580
ttgtttggtt ttttttttgag acagagtctc actctgtcat ccaggctgga gtacagcagc   14640
gtgatctcag ctcactgcaa cctccaactt ccaggttcaa gcgattcttg tgcctcagct   14700
tcccgagtag ctgggattac agatgctcgc caccatgccc agctaatttt tgtattttta   14760
gtagagatgg ggtttttccca tgttggccag gctggtcttg aactcctgac ctcaggtcat   14820
ccgctggcct cagtttccca aagtgctgag attacaggca tgggccactg tccctggcca   14880
ataaaagctt ttgaagcata aaacaaatt tcatttataa ttggtgggta aaacaaaaac    14940
ttgcatccaa atgtttgtag cagccttatt cataataacc aaaaagtgga aacaattcaa   15000
atgtccacca gctgatgaat ggataaacaa aatgtggcat atccatacaa ttgaatatta   15060
ttggacagta aaaggaatga gtactgattc attccacaac atggatgaac cttgaaatat    15120
tatgctaagt aaaagaagcc agtcacaaaa gattacatat tatatgattc catttgtatg    15180
aaatgttcag aataggcaaa tttatggaga cagaaagtag atcagtggtt gtttagggct   15240
gtagtagggg aggggacaat gaggaatgag tgctaatggg tactaggttt attttttgggg   15300 tgatgaagat gtcttaaggc tgattgtacc aacgattgca gctgtaaata tgctgaaaac   15360
cattaagttg cattctttaa atggataaat tatatggtat atgttttgtt ttgttttgtc   15420
```

```
ttgtttttga gacagagtct cactctatca cccaggttgg agtgcagtgg cgcagtctca   15480
gctcactgca acctctgtct cctgggttca agtgattctc ctgcctcagc ctccccagta   15540
gctgggataa caggtgcaca ccaccatgcc tggctaatgt tttgtatttt tagtagagat   15600
ggggtttcat catgctggcc agactggtct cgaactcctg acctcatgat ccacccacct   15660
cagcctccca cagtgctgag attacaggca tgagacactg tgcacagcca gtatgtgttt   15720
tatatctcaa taaggctgtt aaaatatctg tgggaggttg ggcacagtgg cttatgcctg   15780
taatcccagc acttttttt tttttgaga tggagtcccg ttttgtcgca caggctggag   15840
tgcagtggcg tgatcccggc ttactgcaac ctccgcctcc cgggttcaag cgattctcct   15900
gcctcagcct cccaagtagc tgggactaca aagtgcgcc accatgcctg gctaattttt   15960
tgtatttta gtagacgg ggtttcactg tgttagccag gatggtctcg atctcttgac   16020
ctcgtgatcc gcctgcctcg gcctcccaaa gtgctgggat tacaggtgtg agccaccata   16080
cccagcctaa tcccagcagt ttgggaggcc gaggcaggag gatcacttga ggccaggagt   16140
tcaaaacaag cttgggcaac atagtgagaa cccagtctct acaaaagaaa aagtaaaaag   16200
ttagctggat gtggtggccc atacctgtag cctcagctac ctgagagtct gaggcagaga   16260
atcttttgag cccaggagtt tgaagccacg tgagctacca ttgcaccact gcactccagc   16320
ctgagcaaca aaacaagacc tggtctcccc caacctcctc ccccaccaga attctgtgga   16380
gtaagtgaat gaaaacagaa gttaaagcag atataagaat gatacaatat tctgactata   16440
aagaagatc ttgtacattt acaaaacact atcaattcat tgcaaccatt taaatttggg   16500
attatagcta cttgggaggc tgaggcagtt ggattgcttg agttcagaag tttgagacta   16560
cagtgagcca taatcgcccc actgcactct agcttggatg aagagtgagc cccgtcaagt   16620
aaataaataa taaaataaat aaataaataa tttggatgtc aaatcagaaa ttgcatagga   16680
gggccgggct cacgcctgta atcccagcac tttgggtggc ccaggtgggc agatcatgag   16740
gtcaggagat caagaccagt cttgccaaca aggtgaaacc ctgtctctac taaaatacaa   16800
aaaattagtc gagcgtggtg gtgcacacct gtagtcccag ctactcggaa ggccgaggca   16860
ggggaatcgc ttgaacccgg gaagtggagg ttgcatgagc caagatcgcg ccactgcact   16920
ccagcctggt gacagggga cactctgtct caaaacaaac aaacaaacaa aagaaattg   16980
cataggaata tgtagttttg tttttgtggg gttttctgtt ttgtttgtt ttttgagac   17040
aggatctcgc tctgtcactc aggctggaga gtagtggtgt gatcccggct cactgcagcc   17100
tccacctcct gggttcaagc gattctccca cctcagcctc ctgggtgtct gggaccacag   17160
gcctactgcc acaaaaccgc ctgcctcggc ctcccaaagt gctgggatta caagcgtgag   17220
ccaccgtgcg cagccctgta gtttttattt taggagattc ttaagcaaaa aagcctgaag   17280
cccagagaat taaatctctt aaagagaatg ctagattaa atgagaaaag aggactaaag   17340
aaggaaaatt tcagactagc cgatgtggca aaccctgtc tctacaaaaa atccaaaaat   17400
tagctgggca tggtggtgtg tacctgtagt ctcaggtatg caggagctga ggcaggagga   17460
tcactttgac ctagtctcat ttaaaaacaa caaaaacaaa acaaaaacaa aaggaaaga   17520
gagaaaatta ggaatactag catctaaaga aaatgcagga gaaatggaga agtaggacta   17580
gaaccacaga aggactgttt acagctggag ggtagtgtca agcatccctc aggattgtgg   17640
aagctcagga ctcaaaatca tctgtgattg gcaattatga agtctttgac tttggcacca   17700
cccatttcag tgaattaatt gcagtccagc acagagactg atggctggga acaggagttc   17760
```

```
agagaggtta gaggcgagaa tcagagggag gaagtgaaga catcaactgt gaactacttt    17820
cttgagaagt tagaacagaa ataatacggc agtagtttgg taacttttgg gagaagtggt    17880
gtaaaggtag ttgttactac tttgaaaacg agattgattt gaacataaac caaaggtaaa    17940
aagctggtga gtgagagaga ggagggatgc tcatttctgt tgtatgcaaa atgttctgca    18000
aatcagctag ccttggctgt gacccctggg aagccagagg ggatgccatc cccttactt     18060 cagaattgtg gcctttctct tctggtgagc taggaatttt attcagtact tctcgggaat    18120
tttacaaact cttatctagg cagtgagcca ctatcttgat actcagtttc caaaaccgct    18180
tgtttctaca gagctcattt ccaatgttgc caatgtttag tgctacaaca gggatggggg    18240
tgtggatgga ccaacaggct agctcaacat tcttttgaat ttgggttaag tgactgattt    18300
agggtaagag tggctcccag ggccaggcgc ggtggctcac gcctgtaatc ccagcacttt    18360
gggaggccga ggcgggcgga tcacaaggtc agaagatcga aaccatcctg gctaacatgg    18420
tgaaaccccg tctctactaa aaatacaaaa aattagccgg gtatggtggc gggcgcctgt    18480
tgtcccagct actcgggagg ctgaggcagg agaatggagt gaacccggga ggcggagctt    18540
gtagtgagcc gagatcgcgc cagtgcattc cagcctgggc tacagagtga gactccgtct    18600
caaaaaaaaa aaaaaaaaaa aaaaaaaag agtggctccc gaatttcttg ggtaggagta    18660
aaaaagattt tacggtattt tttttctca ccttagttct ttagaattat gctggaagga     18720
accaattcac ctcaaatacc aaggaaatgg gtgtgatgta gtaggcagag gagtagcctt    18780
ttccatactg ccagcagaat ggagacagac ctgggctcgc acacaccacc cggacccagg    18840
agtgggtggt tcaatgtgta ctgttaagac taaagaaggt tggccaggcg tgatggctca    18900
tgcatgtaat cccaacattt tgggaggcca atgcgggcgg atcactcgag cgcaggagtt    18960
tgagaccagc ctgtgcaaca tggcgaaact ccatctctac aaaaaataca gaaaagctgg    19020
gtgtgttggc acgcacctgt agtcccagct gctctggagg ctgagttggg agaatcacct    19080
gagctcagga ggttgaggct gtgtgagcca tggttgcacc actgcactcc agcctgggcg    19140
acagagaccc tgtctcaatt aaaataaaaa agaaggtcat gtgaaagctc actgtgaaca    19200 ggacttttt ttctctgtag gtgcttcatt gttacttcag tttacttgaa ctcatttcat     19260
tgttttcaca ctgttatgaa atgctctcaa caataactgc aacaacaaat agagaagaaa    19320
ggaagtattt agtaatatca agagagggcc gtggttagca tgagacatct tgcgttattc    19380
accactgcaa tgagaagaaa aagactgagc aaagggaatt tcatccattt ctcaaggatt    19440
tagagagcta catgctccat ttgaaggtca cattgtacat ggtgaggtca cattaaggga    19500
attgacttcc tcctctaaat cccctgatc tttatatatt tctttccatg gttttatgct     19560
aatactttga agaactgaag aatgttatga ggtggccagg gaatgctatg gttccaggta    19620
aatgtatttt caaggtcttt ggcagtcggt aaaccatttt ccaggacaca ctttggtgta    19680
agcatactag tagtaaatagt aacaagtatt agcaggaaaa actatcttag ttttttgaat    19740
ttatacttaa tattgttatt gttcttacct tgttttatag ctgagatatt aagttccctg    19800
ctgtgtgctg agggcattga gaacccaaag ataaagagga cacagcccct ctaaaaacct    19860
ttctagggcc ctgtggctcc ttgtccttgg gtggaattca ggggccctgt gaacttttat    19920
aggaaaagat tacagtttta tcaccctcta actgcaatac agtatttcct tcagttatca    19980
atggtaatga caagccacag gagtgacagc tattcccatt tatacatatc actactttga    20040
aataatggta gtcatttgat ttaccactag atcaataaca aggcacatat ggtatgcacag   20100 ccaataaatg tttgaatagt ttgataactg tatttcataa ttagtttct gcatatgcct     20160
```

```
atgtctattt taccatattt tgagaaggct ttaggaggca caaaaaaagg ttaagaaccc   20220
ctttctgttt actatctcat gaggaaggct agaagcttca acagataaaa tcagtacaaa   20280
gtggtgagtg gcagctagaa acatgctcag gagctgtgga gcacaggctt gagcagagat   20340
tcagggaagg ctgatggaga agattcctga gctgcatctg gaatgaagaa gaaacagaag   20400
caggaaaagg tcattcccag gagagaacag aacagatctt agggcaggaa atggcctatg   20460
tggaaggcgg gtactgacag tcagagcttg cttactgtgc taagtcttgg gggctcaaga   20520
atgaatgagg gacctcctag gtggtcagtg tgctcactgt tcagaacaat gtttatgggg   20580
acagggtgga gaggggtata gtttgaaaaa ggaaattttt tttttggaca cggagtctca   20640
ctctgtctcc caggctggag tgcaatggca tgatctcggc tcactgcaat gtctgcctcc   20700
caggttcaag cgattctcct gcctcagcct ctcgagtagc tgggattaca ggtgtccacc   20760
accatgcccg gctaattttt gtattttag  tagagatggg gtttcaccat gttggccagg   20820
ctggtctcaa actcccaacc ttaggtgatc cgctcgcctt ggcctcccaa agtgctggga   20880
ttacaggcat gagccactgt gcctggccgc cttttctagaa ttttatatga gtggaatcat   20940
acaccatgtg ctcttctctt tggtctggct tctttcacat ggcataatgc atttgagatt   21000
tgttcatgct gttgcaaatc aacagttcat tcccaatttt tttgccaagc agtatttatt   21060
atagaattat atactctgaa aaggggaaaa aaaccaacct ttgttttcat aaaacaaaat   21120
tttaaaaagg agtgagattt ttaatgctta tcaaatggga atatgagtta aaaattgttg   21180
agaaatgctg ctccagcatg tggtcagaga gcattccagc ccaagatttt cttatgtcaa   21240
tgctaaattt gagcacattt ggaagtattt tagacctgaa agaaggcagg acatcaaaac   21300
aaccactaga gccgagtggg cctttgtaac cacagactct ctgacgaaaa gatttgtaaa   21360
gactctgcct aatgaagagt tcaaaaagca ttttgtgtgt catctgtttt ccttacagtc   21420
tccttacttg gtagataagg ggcaagaatt attttccatg ttgcataaat aggaaatgag   21480
gtatagcgag tttgagatac ttattaccca agatcccagg gagtcagagg cagactgagg   21540
actgcaaaag atccctcctg gtccacaatc ttagccttgc cagtaggctg ggctgaaagc   21600
tttaaaaaaa aatacagtaa tttcactttc acttttgttc ttgtttgggt tgtgatacaa   21660
tctttaattt gaaagaatga agggttttct tttccttctt tgttttttaaa actttcccct   21720 ctcttcttgg taaacaccaa catgtgtgtt gactctatcc agttgaactc aacaacctaa   21780 tgcctgttt  gtgccaggct cttttccagg cactaaggag gcactgatct ggacaaatcc   21840
tggaggttac tgtgaagcag gaaggacaaa atgaccaaat gagaattaaa ttactttttt   21900
agggtcgtgg aagatttgaa aatctgggga acatatgtg  tcctctttcc cccaaaaaat   21960
gcacatagtg tgtacacaca cacacacaca cacacacaca cacgtgtgtg tgtgcgcttg   22020
ggctcacatg attttgcaat gattttagcg tgtttagaga ccccccagaa cttgtgtgta   22080
ggattggcct ttgatgagt  attttttggca tagaatgaaa tagtaatgcc ttgaaggcag   22140
cacaaagcca tagtcactga atagagagaa agattcagag gatcctgtga gatgggtggg   22200
gctgttagtg ttttgataga cacgtgtact gagttgggag ggtactaatt tctggaaggc   22260
aatattccag gcagagggca catctgagaa aggtaggagg ggagggaagc agaaaaatgc   22320
aaagcaatct gagaaaccca gtttggctgg aggatagatt atatgaagag caatcttcag   22380
aaacacccat agaaaggtag gcaggggtca tattgtgagt gatactgagt aagcaaggtg   22440
agtagtcttc tttttattct ccccagtaaa atattctgca gttccttta  tttttaatta   22500
```

```
gatggcaaaa ccccatctct atcaaaaaac acaaaaatta gccgggcttg gtggtgcatg   22560
cctgtagtcc cagctacttg ggaggctgag gcaagaggat cacttgagag tgagctgtga   22620
tcatgccact gcactccagc atggctgaca cagcaagatg ctgtctcaaa aatatgtata   22680
tattatatac agttttctgt tgttgtttgt ttggtttttt tggagatgga gtttcattct   22740
tgttgcccag gctggagtgc agtggtgtga cctctgctca ctgcaacctc cgcctcctgg   22800
gttcaagtga ttctcctgcc tcagcctccc gagtagctag gactacaggt gtgcaccacc   22860
acacccagct aattttttata gtttagtag agatggggtt ttaccatgtt agtcaggctg   22920
gtcttgaact gctgacctca ggtgatccac caaccttggc ctcccaaagt gctaggatta   22980
caggcgactg gcctttttttt ttttttttttt tttttgagat ggagtcttgc tctgtcacct   23040
aggctggagt gcagtggcac aatctcggct cactgcaacc tccgcctccc gggttcaagc   23100
gattcttctg cctcagcctc atgagtagct gggactgcag ttgcgtgcca ccacacccag   23160 ctaattttttg aatttttagt agagacgggg tttcaccata ttggccaggc tggaggtttt   23220
tgtttgtttt ttttttttttg agatggagtc tcactctgat gcccaggctg gagtgcagtg   23280
gcacagtctc agttcactgc aacctctggt tcccgggttt aaacagttct cctgtctcag   23340
cctcctgagt agctgggact acaggtgcat gccaccaaga ccagctaatt tttgtatttt   23400
tagtagagat agagtttcac catattggcc aggctggagg tttttttttt tttttgagat   23460
ggagtctcac tctgatgtcc aggctggagt gcagtggtgc aatctcagct cactgcaacc   23520
tctgctttcc aggtttaagg aattatcctg tctcagcctc ctgagtagct ggtacttaca   23580
ggcacatgcc accacgacca gctaattttt gtattttttag tagagaaggg gtttcaccct   23640
gtcaccatat tggatggggt ttcaccatat tggcctcaaa ctcctgacct caggtgatcc   23700
actcacctca gcctcccaaa agtgctggga ttacaggcat gagccactga gcctggccaa   23760
atcagttagt ttttgctagt aacaattccc cctaccacta aaatttcatg gctttaaaca   23820
atcatatatt tagcttgtga ttttgtggtc agatgattct agtctgggca gctcagctgg   23880
gtagctgatg tcttctgggc ttgtccccat gtctggagcc aaccaatggg ttagatggtg   23940
gccaggtgat ccaggaaggc ttcccttatg tgtggccact ggctaagagc cttggtgctc   24000
ctccatgttt ccactcctct agcaggctag cacgggctta ttcacatggt ggtcttaggg   24060
atacaaatgc aagcaggaga gtaaacccag agcacaggtg aattaaagcc actgcttgcg   24120
tacatttgct tcacaagtca catggccaac taaaatgcag gggcaggaaa tagactcaac   24180
tttctgatgg gaagaactgc aacatcacat tgcaggatg tggaagggag aacttgtggt   24240 ggttttgta aactacctca cctggtcatt gaatacattg attccacagt atatgataga   24300
tacaggcagc taacaaaaat ttggattatt ggataaatta ttggccatat atatacatgt   24360
atatatgtac catacttatt ttgcaaatag gcttgaagcc tgcctaggaa aaactgagtc   24420 tttttttttct agcctatctt attttttggat ccttatatta gtgatatatg gagcttaaat   24480
attgcagaac tagtaacaaa atgttaatgt caatacctca gaaaagggag ttactgaaga   24540
atactgaact taatgtacag ttgaattaaa taaagatagt agcctaagcc aaatattatt   24600
agactagtga atgatagaaa caaaaagcta caagaggtt tggtttgcat gttaaaaagt   24660
atcctatgca tgaaaccact tcacatctttt atgcctcatt gtcatttcca attagactac   24720
tctctagaat tatttcacat ttccaaaatg gttgaattag ttgggttaca attccagctg   24780
catacaggat tattttacag gtaagctagc catatctggg ttacaaaaca gtgtcagaaa   24840
tatggtgaat ggtgtttacc attcttgcac tcatatatct acacatgcag actaacagtg   24900
```

```
atgggacatg acttatgcac caggcattgt aatacagaga aaaatcagac aaaaccctct   24960
ccctccagga gctcatatgc tttgtgaggg agagagatac ataagtacag ttccagagat   25020
aagtgctagt aaaattttgc agatgatact acagagccta gattttttt tttttcaaga   25080
tctctctctg tcactcaggc tggagtacag tggtgcaatc aaggctcaca gcagcctcaa   25140
cctcctgggc tcaggtgatc ctctcacctc tgcctcccaa gtagctggaa ccacaggcgc   25200
attagcatgc ctgtctaatt tttttttttt tttccgagac agagtgttac tctattgccc   25260
aggctggagt gtagcggtac gatctcggct cactgcaacc tccgcctccc gggctcaagc   25320
aattctcctg cctcagcctc ccaagtagct gggattacag gcatgcgcca ccacgcccgg   25380
ctaattttta tattttaat aaagacaggg tttcaccatg ttggccaggc tggtcgcgaa   25440
ctcttgacct catgatccgc ctgcctcagc ctctcaaagt tctgggatta caggtgtgag   25500
ccactgtgcc cggccctaat ttttaaagtt tggagagata gactctccct acgttgccca   25560
ggctggtctc aaactcctgg gctccagtga gacttccacc tcagcctgcc aaagtgctgg   25620
gattacaggc gtgagccccc atgcctgggc cagattttta acattggctt tttttttttt   25680
tttttttttt tttttttaag attgagtttt gctcttgttg cccaggctgg agtgcaatgt   25740
cctgatcttg gctcaccaca acctccacct cctgggttca agcgattctc ctgcctcagc   25800
ctcccaagta gctgggatta caggcatgtg ccaccactcc tggctaattt tgtatttta   25860
gtagagacgg agtttctcct tgttggccag gctggtctcg aactcctgac ctcagatgat   25920
ccacctgcct tggcctccca aagtggtggg attacaggca tgagccacca cgcctggcct   25980
aacattggtt ttttatatta gtaatgacat agcaagtcac tctggaactt ttataaagga   26040
catctgccca ggtattaacc ctggagattc tcattcattg gtatggagt ggggaccaga   26100
tggctgtatt ttggaaaggc acaaatgata ctgagaggta cttctaagaa ccattgcttt   26160
ataaaatgtt agtgtggccg ggtgcggtgg ctcacgcctg taatcccagc actttgggtg   26220
gccgaggtgg gtggatcacc tgaggtcagg agtttgagag cagcttggcc aacatggtga   26280
gaccccctct ctactaaaaa tacaaaaact agccagacgt ggtggcgggc acttgtaatc   26340
tcagctacta gagaggccga ggccagagaa tcgcttgaac cccggaggcg gaggttgcac   26400
tgagccgaga tcgcgccact gcactccatc ctgggtgaca gagtgagact ctgtctcaaa   26460
aagaaaaaaa aatgatgaaa gataggttta ttggtttttt tttttttttg agatggagtc   26520
tcactctgtc gcccacgctg gagtgcagcg gcgcgatctc ggctcactgc aagctccacc   26580
tcccgagctc acaccattct cctgcctcag cctccggagt agctgggact acaggtgcct   26640
gccactacgc ctggctaatt gtttgcattt tttttttttt tttagtagag acgtggtttc   26700
accatgttag ccaggatggt ctccatctcc tgacctcatg atccgcccgc gtcgacctcc   26760
caaagtgctg ggattaggtt tattgtttta agaatagtt ttattgagat atgattcaca   26820
taaatgtaat tcacccactt aaagtgtaaa ttcggtggtt ttaaatatag tcacagaatt   26880
gtgcaaccat caccagaatc aattttaggg cattcttatt gctccacaaa gaaacctcgt   26940
gcctattacc agtcactccc cacatcttct caactcgtcc agtcctaggc aaccactaat   27000
gtactttctg tctccagatt tgtctctcct ggacatttca tataatatgt ggtcttttgt   27060
gactggcttc ttcctttctc gcttccctc cgctcccctc cctccgttc cctccctc    27120
cactccactc cttcctccc cactcccctc ccttcctctc ccttccctc ccgtttcctt    27180
tttgatggag tctccctatg tcacccaggc tggagtgcag tgacgcgatc ttggctcact   27240
```

| | | | | | |
|---|---|---|---|---|---|
| gcaacctctg | cctcccggat | tcaagcaatt | ctcttgcttc | cgcctcccaa | gtagctggga | 27300 |
| ttacaggtgt | ccaccaccac | acccagctaa | ttttttgtact | tttagtagag | atggggtttc | 27360 |
| accatgttgg | ccaggctggt | cttgaactcc | caacctcaag | tgatccaccc | acctcagcct | 27420 |
| cccaaagtgc | tgagattaca | ggtgtgagcc | accacacctg | gcctgactgg | cttcttcac | 27480 |
| atagcataat | gttttcaagg | ttcatccgtg | ttatagcatg | tgtcagttct | tcattctctt | 27540 |
| tcatggatga | atagtattcc | attgcatgaa | ttaaatgtag | tacaatttgt | ttatctattt | 27600 |
| ctcatttggg | ttgtttccag | tatttgccca | atatgaataa | gaatgatgct | gctggccggg | 27660 |
| cgagatggct | cacgcctgta | atcccagcac | ttttgggagg | ctgacggggg | tggatcacct | 27720 |
| gaggtcaaga | gtttgaaact | agccttgacc | aacatggtga | aaccccgtct | ctactaaaaa | 27780 |
| tacaaaaatt | agctgggcgt | tgtggcatcc | gcctgtaatc | ccagctacta | gggagactga | 27840 |
| ggcaggagaa | tcgcttgaac | ccgggaggca | aaggttgcag | tgagccgaga | tcgtgccgtt | 27900 |
| gcactacagc | ctgggcaaca | agagcaaaac | tccatctcaa | aaaaaaaaaa | aaaaaaaaa | 27960 |
| aagatgctgc | tatgaacagt | catgtacaaa | ttttatatg | gacatatgtt | ttcatttctt | 28020 |
| tgggtaaacc | cttaggagag | gaattcctag | gcgacatgag | aattttgttt | cctcttttga | 28080 |
| gaaactgcca | aacttttcca | aagcaaatgc | accattttac | attccatcag | cagtgtgaga | 28140 |
| gctccagttt | cttcacattc | tccctaacac | ttgttatttg | tgattttgat | tatagccaaa | 28200 |
| gatagatttt | attatcccca | ttttaagat | aaggatatca | tggtttagag | cagttgtcag | 28260 |
| gccatagaca | ggtactttgc | actctcagac | actggacctc | atctgccata | gcactttgaa | 28320 |
| atgaccttat | aataattgaa | agaggaaggc | cgggcatagt | ggttcacgcc | cgtaatccca | 28380 |
| gcactttggg | aggccgaggc | aggtggatca | cctgaggtca | ggagtttgag | accagcctgg | 28440 |
| ccaacatggt | gaaaccctcgt | ttctactaaa | aataccaaag | ttagctgggc | gtggtggcgg | 28500 |
| gtgcctgtaa | tcccagctac | ttgggaggct | gaggcaggag | aatcgcttga | acctgggaag | 28560 |
| tggaggttgc | agtgagtgga | gattgcacca | ctatgctcca | gcctaggcaa | taagagcaaa | 28620 |
| actccatctc | taaaaaaaaa | aaaaaaaaa | aaaggaaata | ataataattg | aaagaggaaa | 28680 |
| acatggaact | atatatggaa | ttgttttcaa | atactttagt | attttttcca | gaattaatgg | 28740 |
| gcaatttaat | atttcatata | attgacttct | gtaaatgact | ggtattcctt | ttttttttga | 28800 |
| gatggagtct | cactctgtgg | ccgaggttgg | agtgcagtgg | tgcaaccttg | gctcactgca | 28860 |
| atctctgcct | cccaggttaa | agcaattctc | ctgcctcagc | ctcctgagta | gctgggatta | 28920 |
| caggtgcctg | ccaccatgcc | tggctaattt | ttgtattttt | agtagagact | gggtttcacc | 28980 |
| atgttggtca | ggctgctctc | aaactcctaa | tgtctagtga | tccacccacc | ttggtctccc | 29040 |
| aaagttctgg | gattacaggt | gtgagccacc | acgcctggcc | aactggtatt | ccttttataa | 29100 |
| aatacgtatc | tgacttattt | tgttgcctc | attacatcaa | gatttacatc | caagttaaat | 29160 |
| ttgtatagat | tataggtaat | caagtgtggt | aagcacctac | tgaaatgttt | aaaaatttta | 29220 |
| gaatttcctt | actgtcaaaa | tgataattct | ttttttttt | tgagaagggg | tcttgctctt | 29280 |
| tcgcccaggc | tggagtgcag | tggtgcgatc | ttggctcact | gcaacctccg | actcctgggt | 29340 |
| tcaagtgatt | ctcctgcctc | agcctcctga | gtagctggga | ttacaggtgt | gtgccactat | 29400 |
| gcccagctaa | tttttgtat | ttttagtaga | gacagggttt | caccatattg | gccaggctgg | 29460 |
| tcctgaactc | ctgacctcag | gtgatacacc | caccttggcc | tcccaaagtg | ttgggattac | 29520 |
| aggtgtgagc | caccgcgccc | caccaaaatg | ataattctta | accagaggaa | atagacaaat | 29580 |
| gaacagaaac | tcacatggaa | aggtttgttc | caggggttca | cattcatgat | tgttcatcag | 29640 |

```
acttcagagc tttaaaaaat agaatacagg tgcacaggct ctaccccaga ttaagtgagt    29700
caggatcttt gtggttggct ctggggtgtc tgcatttgta aaaagctccc cagctgattc    29760
tgaggctcag ctgaggttga gaatcaatgg tttgtgtgac tgagatggtt ggcagtatga    29820
agatgttttt gagaaattta ctggcagacc tagctgggca tccagcttga ttggtctgtt    29880
gcatggggtg gaaaagatag ttggggtggg ggtatggggt ggctttggca ggtgggagat    29940
ggcagtgcag gtaatgcaga aaaggaattt aagtaaagta gtgtgtgttt ttgaagccaa    30000
tgagaagctt ccttataaag aaataatatt catatgctgt aactctattc ccacctcaac    30060
ttgttttgaa aactttaaat ctagagagaa gttgaaataa aggtacaatg aacacctgta    30120 ttgttttat ctaggttcac cagttaacat tttgctgtat taacactggc tcttcctccc     30180 aaccccttt ctaaaccatt tgaaagtaag atgcagtcac tgtggccttt gcatttaagt     30240
aactgtgaag aataggaata ttttcctaca taaccataat ataattatta cataatgaaa    30300
tttaaccttg gtattatacc gttaccgaac atacagtcta tatttgctct tcatagctct    30360
tttttttttt ttttgattcc aggatccagt tgaaaatcag gcattgcatc cagttatcat    30420
ggctttaatc ttaatgcctt ccctgcactg ttttgggaat atcttaatac tgctattttt    30480
gaagagtcca gctcagttat tctgcagaat gtctgttgat ttggctttgc tgtttcctca    30540
taagtagatc cagattatac gttttttgttg atgttgggtt cttctcagtg aatcacatcc    30600
gatgatgtca gcacgaggcc tgatcatttg gtttaggtag ctttcactag acttttttcat    30660 tgtaaaggta cctatccctt ttctaattaa taagtaatat gttgggtgat agtttgtgtg    30720
tgaatatcct tttctccagt gacctttcat ccaatggttt cagcattta aatgatcctg     30780 ggctgagtca gttttcagtg gtggctgcag acttgtggtt ttccaattct ttcatcactt    30840
ttacatttat taattggcag tctatgactt cttatagcca cataaagata attcaggaat    30900
tatctgaacc tatgaatgtt accttatttg gaaaagagt ctttgcagat acaattcaat      30960
taagaatctt gagatgagga gattatcctg gattatccaa tgggcccaa atccaatgac      31020 aaatgtcctt ggcagaggga gatttgagac aggagaagag aagacacgaa ggagggaagg    31080
aagtgatgtg accacagagg cagcgattgg agtgatgtag tcacaagcca aggagcacca    31140
acagccacca ggagctggaa gagcccaaga gtatatacta atacctggat ttgggacttg    31200
ggacttctgg tctctagaag taggaaagaa taaacatctg ttttttgtt                 31249

<210> SEQ ID NO 4
<211> LENGTH: 37000
<212> TYPE: DNA
<213> ORGANISM: Homo sapiens

<400> SEQUENCE: 4
gggaattgtt ttggatagga ctttcagatc aagtaaggtc agatcagcct ctcatcagaa        60
gacacttgta gcagagtgct tactaaggaa gtgaaggagc tctgagtttg tcatatgaat       120
attgggaaaa agaatgttcc aggcagtgaa aacagcatga gcaaaggccc tgaggcaata       180
gcatacttga tgtgttccac taaggagggc aatgttgtgc ctggagtgga gtcaacaagg       240
aagagattaa gctagaggct gaggtcagag agatgggtga ggtggccaga tcatatgagg       300
ccttgtaaat caagataagg actttctttg gcttttgagt aaaatgggaa actatagaga       360
ttttaagcca gaggagtgac atcatctgac ttcaaaggag ttttatagt gtgttgtggg       420 cttttatagg ctcaggcaag aggtggatag ggtggatggg gaatagatct tgtagagctg       480
```

```
agtgttccaa tatggtggcc tctggccaca agtggctact taaatgtaaa ttaattaaaa    540
ttttaaaaat taaaaattca ttttatcaat tgcactagcc acatttcaaa tgcacagtag    600
ccacatgtag ctagtggcta ctgtattgga cagtgagatg tagatcattt ccattgccac    660
agaaagttct actggacagt gctggtaggg tattaaaggt cttttgtaggg acttcagctt   720 ttactctgag taaatagaaa gccattggag ggttttaagc agaggaggaa catgctctga    780
cttatgattt cgaaagatca ctgttgagaa tagactgtaa gggggcaatg gtgaaagttg    840
atagaccatt aatagtctag atgagagatg accatgtctt cgatgagggg gtaggagtga    900
tgatgatgat aaattattgg attttggata tattttgaag gcagaaccaa taggcttttc    960
tgatgaaaat gatgtgatat gagaaaaaaa tgacaaaaag gttgtgggtg atgatgagag   1020
aagagaatac aaggccaaag agaagggatt tcccttgttg tggaggagtc tcactcacct   1080
tgaagcagga gggaaagcag ggatctgggt ggaaaaagat ctagagaatc ctcatctaag   1140
cagaagatga aggagtaaag agagaaagat gggtgtattg gaagcttgcg ggtgatggag   1200
aaagtttcaa ataattcttg gaaaataagt tgaaaaaaga aacgtaacac agttgttaga   1260
gcagggcatg attgcttgtg cctatagtcc cagctacttg ggatcctgag gcaggaggat   1320
ctcttgagcc caggagatgg aggctgcgtt gagctgtgtt tatgccactg cactccagcc   1380
taagcgacag agcaagactc catttcttaa aaataaaaca aaaatgtagt tgttagtatt   1440
gagggcccat aagaagttgg tgatgatgaa cctatctacg cttttgatca cctccagcag   1500
agtttgactg ttgcgtgcaa gcaaagagaa aggagatggc ggggttcaat gagggctgtc   1560
gttttcctag ataggtttgt agaaaaaaca gagaggaagg gagtttaagg gattggcaaa   1620
aaggatatag taataacaga ccatggaata aaaattgagt aagaaggaaa gtgaaaacag   1680
ctgaaggcta atgaattggg agaaagcaga tggatcaata gactggaggc cccaatattt   1740
ctaagagcag ttggagttgt tgtcatgcaa gttggaagga aagatgctta tccaaaagct   1800
gaatgcctga atcagtaatc ttgcggcaga gctattgtag gtgatgacaa ggtcagtcct   1860
ttgaagtcta tgcatatata tcttcattat aggctgactt gccaagtctt agaatttta    1920 caatataacc tcactgtgga tctcatctaa gcaggtttgg taaccaaaag ctcaagagcg   1980
tgagattgag accccagaga gctcatagcc tgtcacaaac cagctgtgta accacggacc   2040
ttgaggaaat gaaccttatg gtcccttccg tctctaatct gtgactccat agccccatta   2100
taatatagcc ttttcccaaa cactgacctt caacatagac cctgggggat ttttctatta   2160
aaaatttgca actctgcaca ttttttatctg ctgatgcctc ttggaatatt aaatgcttag   2220
aaagctgtcg tcgggatcac attctggaat cttgaccatg tagtcatctg agtgggtgtg   2280
acaggaagta taccagca gcatttgtgt ctgagtgtcc ttcagacact gggatggctg      2340
cacctttacc cgtcctctcc aactctctcc acctagaaag tattctttc tcttaatttt     2400 gttagagtta tataggaatg ctccttcagc agaaatgaca gaggctgttg ctctcagaat    2460
caaatgcaat aatgtgacct gtaaattcct gtgaatattt ggatatttta gcgatatttg    2520
tttattcaga agagattctg gatgcagaac tctcctcctc tctgttctct aaccctgctt    2580
tccaccatca ttcttctctc tctagggcac agagagaatt aagaacaacc taaggtaaat    2640
ttttaacaag atggtctagc ttgagctctg taggcttgac tgatgaaata agtagtagtt    2700
ttttgctaaa ataaccacat tgtttgcaaa agttttctcc tttgagtttt ctagggtcat    2760
tacaatgatc taactgcctt acctgctttt gaactggttg agcctcttgt gggaccgaaa    2820
acaaaagaag ggtgttgaaa tgcaaataga taactctggg tcccagtccc tgactgcaaa    2880
```

```
aggaagccaa aactgacaac aacgtctcct tctctacgga ggtttgtaga aaggctgtac    2940
aaaaatctca caagatgtat ttcttctcgt ggactggagt cccaaggtag gtaagaaaaa    3000
caaaaacaag ataaaaacaa acaaaggatt ccgtacttgg aatttgctca gtaccagttg    3060
aatagctaat tgtttcttgt gttcttcccc tcccccnttt ttttctgcct gaatagataa    3120
tccttacaaa acatctattc attctacaag tgaaaatttc aagaatattc tatactgacc    3180
ttggcaagag taatggaccg agattgagtg atgaatttgt gtgtgttgtg gctgatgtgc    3240
attttggtgc tttgtatgca agtttaagaa tatcttagca ataggaaagg aagatttatg    3300
gcagtttaat taatgaatat aatgaaggct aaaacttgta gataaattta taaggtacac    3360
aattattttt atagcttatt tttagcacaa aggtgattgt attttgttgc tttaagaaag    3420
gacctcttga taatactggc gtgttttata tttcaatgtg accagtttaa ctgatatgca    3480
aacaattatt ttttaaggga aataaaatga ggcagtagta caacttagcg aagaggacac    3540
tgtggcagat tctaacgact agattaaatt tgagctctta tttggctttt actaccaact    3600
gactgcataa ctttgggtca gttatttggc tcttttttt ttttaattta caaaattaga    3660
atgagaacta cagatagtga aaatatttgg aaaagctttt tgaagtccca cgtgaaaggc    3720
atcagaaaaa agagttgggt gattttttt aatgggaaat aatctgatat tgtcagtaaa    3780
cctaaatttt ttgtatatta atttattttt taagctgtta tttaatttca ggtgcttaag    3840
agctcttcaa tttgttaatg gaaagaaaca ccatttacac cggatggcta caaagcaacc    3900
ttattctggt aaaataatct cttaaatcct tatatacaca gtcactaact gttggcttta    3960
taaggtcagt agtagcaaaa cagccctgtg gcagttagaa gctcagcatg tccaagatag    4020
cactaacggg gaacaaacac aaaaaacagc aaacagttta aacagtacca tttgatttga    4080
atttaaccca atcttaaaca gaggactcta aaaaaacaat taccagcaaa gttacattaa    4140
ttagggagat cattaggttg tatcaatgca gtttagctat gccttttaaa aagtgaagat    4200
ggactagaag cggtggctca tacctgtaat ttcagcactt gggaggcca aggtgggagg    4260 atcccttgaa ctcaggactt tgagaccaac ttgggcaaca aagtgagacc atcatgtcta    4320
caaaatttta aaaattagct gggtgtggtg gggtatgcct gtggtcccaa ctatttggaa    4380
ggctgaagca ggaggatcgc ttgagcccag gaggtcaagg ctgcagtaag ccatgattgt    4440
gctactgcac tccaacctgg gcaactgagt gagaccctgt ctcaaaaaaa agaaaaagat    4500
tgaacttgca ggccaacatt tatttctgac tattgactac ttttgaaaga gaaagctttg    4560
gacactaaca ttctagtctc agaggcctca agaagcaca gccctgtaaa gaagaaaatt    4620
ctgctgggat tagcaagagc ctcaaggttt tgggaacttg gaatgccagg ctcagtgttc    4680
cgagttccaa tgttgactct gcctgtgagt caccctgaac tagtcactca gtctcttgtg    4740
tttccccctt tagagaagag ctaagactat tgacttttca ggagttgcaa acatgttac    4800 aaaaggatag gaaagtacta tgcaaacatg taaatatcat gaaatattgg ggggtacat    4860 tttaataaag ataagctgca ttcttctgat aattggaagt tgataatctt tatgtaaaga    4920
cagggagatt gatttcaaaa tagaggttaa tgcttgaaat tttaattcga acagtgtaaa    4980
tttggatcat tgtttgctct gttagtcgat gttgcttact gaaaggaaac tcttaacaag    5040
ttgtcttact agaatggctt atttcagag tcagacccc aggctttcta gaaatgtgta    5100
ttaaaattta gtaacctcac tttcaattgt tgagtatagg acactgtggt tgggtttcta    5160
tatatgttgt aaacaagcca aatacacaaa gtgaactctc tatggacctt aaaaaagtct    5220
```

```
taaaaatttt ttttgagga tattgaatga ggcacctatt ttattcctta cttttgcagg    5280
atagcttgtc agtgccagct tgggttttg aattctgact ttttgctggc catgatttgg    5340
ctgtctcatt aataagacaa acctttctaa agtggagctc attgttttt agttctttta    5400 atggtgtggc tagcctctca ttgttaaaga aagaaagaa tataatttt attcttcgtt     5460 ctttctggca actttatacc ctctactaac ccacccagtc ctgaaatcct gttagttttt    5520
ccatctgtga ctagcatctc tcttctgatt cccagtaaac gctactatat tcccatcatt    5580
caaaattaac aactgttatt atttttgtca tatcttcttc aatttttta aagaaataaa    5640 acaaaacatt gatgataaaa tcaagttgcc tttgaatatt aattccaagt ccatttcctc    5700
cttctgtcct cacttcccag agcccatgtt cagtttgtat acttttaat attttatata    5760 tatttgtatg tacccatagt taatatgtag tattgtttta tggatttaaa tatacataaa    5820
tgttttcttt tttagagaga gaggatctca ttctgtcacc caggctggag tgcatgatca    5880
tagctcactg cagcctcgac ctcctgggct caagtgatcc tcctgctcca gcctctcaag    5940
tagctaggac tacaggtttg tgccactatg cttggctaat tttttttttt ttttttgtaga    6000 gatgggatct tacaatgttg cctggtctca aactcctggc ctcaagagat cctcccgcct    6060
ctgcttccca aaatgctagg attacaagta tgaaccacca tgcccagcca actgttatat    6120
gatttgttta cttctctga gcattgtttt taaggtctag ccatgttttt gtacagacac     6180 acacacgt gcacacacac acacacccat ctatatat atattcatta tttttaattg        6240
ctgtctagca tttcttttct ttcttttct ttttttttt tttgagaaag actctcgctc     6300
tgtcacccag actggagtgc agtggcacga tctcagctca ctgcaacctc tgcctccgg    6360 gttcaagcaa ttcttctgcc tcagcctccc aagtagctgg gactacaggc gcctgccacc   6420
aagcccggct aattttttgta ttttttagtag agacgggtt tcaacatatt ggccagtctg   6480
gtctcaaact cccgacctca ggtgatctgc ccgccttggc ctcccaaagt gctgggatta    6540
taggcatgag ccaccacacc cggctatttg ctgtctagca tttcatggca taaataatac    6600
cacattttat cagtccattt attagtgaat atatgattgt ttatatttt ttcactaata     6660 tataggcaat agtttcttag tcttgattcc tagatgcagg attgctacat tttgaatatg    6720
cacaatttaa cttttaagag atattaccaa attgattttc aactgttgga aaactgtttc    6780
cccagatact ttccaacact tgtcagactt cttaatcttt gccaatttta ggggtaacaa    6840
atggttttcc ctgggctttc tagctttatt tcagttcatc ctattcatag ttgctggcct    6900
aatcctttct aaggacagca ctgctcaggg ccttgcctgg tcaaacactc tcagaagctc    6960
tgcactatct actcagtcca aactgcccca agtcctctgc aagcaacctg tcccacctca    7020
tctatccatg cccagctgga ccagaacgtg caacttacca cttctcaaa ctcagctttt     7080 acttttctgc ctctgcaact tgatcatgct cttctgcatt cctgtattga ttcaacaaat    7140
atttattgag ctctttactt cctgccaggt gctgggaata taagggtgaa aaagaaagac    7200
catatctagg catttatggg acttaacaat ttttagcaga ggatggggat gggcagaaaa    7260
taatccagta aaaaaattga gcacgataat tttccatagt actttataag tactataaag    7320
aaagtaaaat agaatgttaa tgagtttgtg tggaggagtg acggggtgg atgtgggca     7380 tgtccaggtg ggaactttag aggggcaggt gctcagcgaa ggctttacag agaaggttat    7440
attccccttg agaccagcag tgtgaagctc attcacagac cagaagtatt tctgatcctg    7500
agcaagtgca gatccctgca tgtaggggtg gcctcagagg atcctgagag gagcagagct    7560
gcccttgtgg ctggcagttg gggctaggag agtggtggat gctgtaggag acaaaggcag    7620
```

```
gcaaagccat gcctctcagg gccttgtgga tgctctctac caaagccact gcaggaaacc    7680
gtagtttgcc ctttaaagcc ctgtaaagcc gtgatcaaat cctctcttca taatcattcc    7740
tgatccagct ggctgggcgc gctctttctg gaccaccatt gcacagtagt ggtgcctctt    7800
aaggcattta acatagcact ttgggatcat gatgtctgtc cttcccatga gctattagaa    7860
tttgttttca tgttgctgtt ttgtttctac ctcacaaggg acaatacttt attgtctgga    7920
aagaggaaag tagaggagga aaaggtagaa cacagaagaa gcctgtcatt tttattgag    7980 tctggaatga actgagtttc agtgaaataa gctttcctgt tgtatatttg agctgatttt    8040
cacaatggca aatatgacaa atttaatttt ccttaaaaat tgataagacc agttggagtt    8100
ctaaaagtga ttttttctac cccttgaaga tcttttctca gaatagcagt ctgtaggctg    8160
tcacctaaag tgtcctgttt tcagtgctgc acctgctctg agcttcatct ttttacgaag    8220
acgtcatggt gtgctatctg tactgggaaa cttttcccag catcagccat ctcctgaaga    8280
taacattgtc tgctagagat tgtcatgtat gtggattgaa tctctttatc ttcatggtaa    8340
gtttggagtt gtgtattaga cctaccttac tggtgaaaag aatgaaggtt cgtagaggtc    8400
attacttgtc tgtccgcagg ttacgaaatt agagaatagc gaagctgaca cttgaatctg    8460
gggctactga ccaattctct atgaagcttc cacactttaa gtagtaacat agcaaagacc    8520
aagcacttaa aattatttct agatgaagcc tttgtgctct gaaccactgt gatcactgtt    8580
gatcgcattt tccttcttga actcattttc tattaatagg agcatttatc acagacagtg    8640
agaggcagtt tgtgcagcgg ggaagagcac gggctgtctg aagctagact gtctgagtca    8700
gggtcttctg tgccagcttg ctagctgtgt gggggaagtt acttaacatt tctgtggtta    8760
agtttcctta ttttagtat gaggataata acagcaccta cctcattggg ttgttgtaag    8820
gattaaatag gataatgtac ttaaaaggct tagaacagag ccttgtactt aataagtcct    8880
cagttaatgc tctcctagtc tcaggtctca gctcaaatgt cctctcctag ggaggcctta    8940
cctggcccct gtagctagcc tgggcctccc ccaggcattc aacatcttca ccctctgcct    9000
gcaccctgcc tacttccctc atggtgtttt ccctcttttg gggtaccagg tttattacag    9060
ggttgtctcc tctgtgacaa tgtgagcttt ccatgggttg gcttgtatgt tccagtttcc    9120
agctccagga cagtgcctgg catgtagttt gctctcaatg tacatttgtt taacggctct    9180
ctgtttctga aaatcctgaa tcagagcttt cattttgaac aaaatcgttg ctactctggt    9240
ttcttctcaa tatgccatat gtattagtgt tccctgaaac ttcattccca cagcttcaga    9300
catgatccca aatggctcaa gaatttgtac ttctagccct gactcctctt tctttacttt    9360
tttttttgag acagagtctc actctgtcgc ctgggctgga gtacagtggc gcgatcttgg    9420
ctcactgcaa cctctgcctc ccaggttcag gcaattctcc tgccgcagcc tcccaagtag    9480
ctgggattac aggcgcccgc cactatgccc agctaatttt ttgtattttt agtagtgatg    9540
gggtttcacc atgttggcca ggctggtctt gaactcctga cctcatgatt cgaccacctc    9600
ggcctcccaa agttctggga ttacaggtgt gagccaccaa gcccggccct gactcctctt    9660
tcaatctgta tttccaacta actgttcata aaacaaattc tggtaggtgt ccttagcaca    9720
acatgttcaa aaccaaatgc actacttttt tttttttttt tctaaaccag gtcctctttc    9780
tgtgccccca gccggttga caatgtgtgc cttcactcac ccaattagaa accttggagg    9840
tatcctgtac tcttctgtca cttaccctca gcctaaagcc aatcagtcac caaagtattg    9900
tctgtcatta tcatcatcat catcatcatc actgtcacca ctgatggagt gagaaccttg    9960
```

-continued

```
tgcagttgag catgaacccc aatttcattt gcaaaatgac ccagacagca gatttcatct   10020
catatgaaat aagcaaggtg aggttttgat gacgttacag acatggctaa gaagaggttg   10080
agaaccagca ttcagcccac ctgactccaa agctcatgcc ccgaacctca gaaacttctc   10140
cagtgagttc cttttttta atggcaggat cacaccatta gtttggactg gatccaacct   10200
ggattgttgc aacagccttt gatctgatct gtcaagccct gtgccttctg tgcaacccat   10260
tctctaccct ggcacgagca ttactaaaat accaatctgg tcctatgact cctctgcata   10320
aaaaccacgg ctggggctgg tcaagtgcaa cagtgtttac aactaattga tcacaaccag   10380
ttacagatat cttttgttcct tctttagcca aaaacaaaca gaaaaacaaa caaaacccaa   10440
ataacaaaaa caaacacaaa aaccccccca ttgtttgttc ccttttgcat cttttgaatt   10500
ctaaactcct cacatagcat aaaatcccct tctgggtctt ttcccagcct acaacccact   10560
tccccacctg ccccattccc cctgttgctc ctacctctgg ccttacttca gcccagggt    10620 cccctgctgg acatggcagg cccagcacat gctgccctgg gcccttcac tttgctttgt   10680 gacatatttt tcatccttca accttcagct cataagccat attctctgtg aaggcatcca   10740
gagggcccga gacagcccct cccacctgtg ttcctcagag cattctgtgc ccataattag   10800
ggtgaacaca tttctgaatc agcagtggaa atgtttcagt tcagacagtt acgcatgtgc   10860
ccctgaaggc aatgggacag ttaatagagc aaagtccaga agaaactctt ggagatgatt   10920
cctctttatc tgtctgctac cctgtagagg ggtggggaag gtacttccag ggtagagagc   10980
tgtgggtggc ccttgtatct cttggagatg attcctcttt gtctgtctgc taccctgtag   11040
aggggtgggg aaggtacttc cagggtagag agctgtgggt ggtccttgta tttgcccaca   11100
cctgacacga tgcctaactg ttgtttgctg aatgtatgaa gactatgcca ggcctgagat   11160
tcttttgaac ataaccaaat gtcatgtgta aatttctcca aataaccaac caacaaaccc   11220
agctctttat aacaatggac aatccagcat gagtattagg actctgttta agtctcaggt   11280
ttatcactag aacaattctc atagacacac ttcttcatct gtaaaatggg gataatagta   11340
gctacttacg ggagttgcag tgaagactct gtgaatgaat tgaaggaaat tagcaggcac   11400
agagtctggc aaagaagtct ttgtttcagg cacaaagata tgtgtagctc atcactataa   11460
acaggaacta gaaggcaagg tcatgttcta gaataacttt taaaagttag gatattgttg   11520 ggaatttaa aaggtaagac aattaaaaat atgactaata tttgtcagct tttttttttt   11580 tttttttga tacagagtct tgctctttta cccaggctgg agtgaagtgg cgccatctca   11640
gctcattaca gcctctgcct cccgggttta agcgattctc cctcctcagc cttcttgagt   11700
agctgggatt acaggcaccc gccatcatgc ccggctaatt tttgtatttt tagtagagac   11760
tggggttcac cgtgttgttc aggctggtct tgaactcctg acctcaagtg atccaccac    11820 ctcgacctcc caaagtgctg ggattacagg cttgagccac tgcgcctggc tcatttgtt    11880 agctttaaca tatgaagaga catcctccta aatgttaaag tactctttga catttacct    11940 atgcattta cagttgggct gggagagatg tgactcccgg tttgttttgc ctcacctttg   12000
catttcatca gctgtgtctg atcccagcct agcctgtgtg tcggaatcac ttggatgagt   12060
gttttacaga ctcctgggct ctaccccaaa cccactgaat cagaatgggg acaggaaggg   12120
aactgtaaat ctacatttat gaaaacctcc ccttgtggtt ttgatagtct gcaaggtttg   12180
ggaatcacta gttcccaaac acaccagtag aaaagcatat agtaattaac attctcaatt   12240
tctcagcttt acagtgtttg taattaaaaa tttttatttg ctttttttgta agcaatatta   12300 gctttctcaa tgtctgtttc accttcactg cagtctgttt atccagcctg ggaaaaaaac   12360
```

-continued

```
tggctccact taaacaatga gacaaaaaag gtgcaaacct gacagcttcc ctaccttttt    12420
tgcattagcg tgtaggtatt tcctccatgt cctaccaggg ccatttaaat gctaatatag    12480
ttaagtacaa caatcttttt agcaatcaga tggaattgtt ttttaccaca atcttatttc    12540
tcatttctcc agtccgtact tttccttttt tggggcaggg tgggggtagg gctagagggg    12600
catacattta aattctttga cctttcaaac cttaacaaaa attctctcct aatatcttct    12660
cagcagttct tgcaatgtgt gtatcctcta aacctgagct ctgtaatttg aatgtgctga    12720
gtcaccttgt ctttgcaggg tcaaacattt tgcatccagg aaaagtactg cagaaaatca    12780
caccattagc agctagctgg tatgttattt gaatatttga atacaaatag gaagactgga    12840
aaggagaaag ttactgtgta catagataca tagtaactta catatactta aaacaacctt    12900
tttttttttt ctaatagtct gctaagtcct ctttctgatt gatgactttt ttgtgtgtga    12960
aattctctaa atatttattt gtgttcctag aaagtgaaaa tgaatataaa tggtaaagca    13020
gttgccttgc aatgtttaat aaaaggagaa aatagtcttt gctattatac tgaagctttg    13080
cataattaag attcttgaat taattttaaa gaattaataa caaaaaaata caatcatgaa    13140
ccagatattg agagttaatg tctaatttaa gttcaacttt tagggagtcc gttttcctat    13200
tttgatcatg tagttgaata gacagtgagg agatgttact acaactgtat taatagagga    13260
agtggcagga agctacagtt tccttagaat cagaaagaaa gtttatagaa ctcactggaa    13320
atgagggtta tagataaaga ttgaagtagg aataacttct atttagaatt gctattgtat    13380
ttttgtaaca taagagtggt tttctttaaa gtaagtattt ggggctaaag agaatgccaa    13440
cactccactc acagggaagt cggaaagctt accagtatta acaaacatcc gaagtcattt    13500
cacaaggtgg aagtttacta tagaaccagt aaacataatc ttcctccagg gtgttttgag    13560
tcatgaatgg ggagcaactt gctcccttcg tggatggagc actggggaca agcttctctg    13620
catcagagcc tgtgaaatat caatagcaac agctactgta ctctgagtgc tcacttcctc    13680
tatgccagag gctggctctg gtcttttaatt gaattcgctc actatacagc cccctataca    13740
gaaggaacgc taattttcaa taccttaaag aggccaaatc attcccacag cattagtggc    13800
agagggggta tttgaaccca ggcagaatga ctcgaactcc ctggtaatta gccatggtgg    13860
agaatgtctc ccagctcaca aaaatgacta ctcactggca agtaacacta agtacagaaa    13920
gaatgtcatc agttggttgg tgttcttgct ttctctccgt gaacaattaa gagggcgcag    13980
aggtgagatg gggtggggtg ggataaaggg aaggcctgga agaagggaca gaagggctgc    14040
aaataatcac ccgggagccc agtgagactc agagaaagat tctaacctaa aatactcttc    14100
tgctgtcagc tattctgtaa ttaacatcca cagatgaaaa catgaagtgt attaaaaatc    14160
ctttgtgttt tttttcaatt ttgactgatg gacataatat aatgacttga taattaaaaa    14220
aaaagaaaga aagaaaaccc acaaaaccca acacccaaa attctaaact aactgctttt    14280
catcattcta ctccctgatt agacatggaa ttggctcgt tactacgggt agaacaatgg    14340
cctgtgttgg gcaggacaag ggcatggaag ctctccagca agcagcacag tgggacagca    14400
caggcttcta gcaggcatgg tttcagtctc aattgtttac aagccttggg atctggaaca    14460
attgatttga gccctacaac attagaatgg ttccttttct cagggcctaa tatgggtca     14520 gagaaggcac tcagcaagga gggttttttc agaggcccag gaagaactag ttcagaggcc    14580
gagcctcctg ggagaacacg tagatgagtg gggtcaggtg cctgtgtctg agatctagct    14640
caggtcaggg cagttttcat tgagaaggtg acatttgaac aaagatttga agttgctgag    14700
```

```
tgagttagcc atgtgggaat ctcaatagaa gagatttcca agcagaggaa acaactaagg   14760
agaaacagga aattgccttc tggcaagatg taggaacagc aaggaagtaa gtgtggctga   14820
aacagagtga gtgaggggta aagtagttga aagtgaggtc ggggagtaag agagtcagac   14880
tggccagcat cattttaagg actctgagtt ttaactatga gaggaacatg gagccattgc   14940
aaagttctga gcagaggagg acatgtgact gagagtttaa aaagatggct ctaagccagg   15000
tgcaatggct catgcctgta atcccagcac tctgggaggc cgaggcagga ggatcacttg   15060
aggccaggag tttgagacca gcctggacaa catagcctga cctcatctcc actaaaaaag   15120
aaataaagct gggtatgctg gttgcgtacc tgtagtccca gctactcagg aggctgaggt   15180
gggaggatca cttgagcctg ggaagttgag ggtgcactga gtcatgatca tgccactgta   15240
ctccagcctg ggcaacagag caagaccctg tctcaaaaac aacagcaaca acaaaaatct   15300
aaaacgattg ctctgattgc tatattcaga atagactggg tttgaagcag aaagaccagt   15360
taggagccat tgagtaatcc agacaagaga tgatgatggg tctgaccagg gttcataaca   15420
gtatgagggt gagaagtggg cagattctgg atctatgttg aaggtaaaac caacaggatt   15480
tatccctggg ttggatatgg aatgtgagtg gaaaagagaa cgtgaggatt tattccaggg   15540
cttatggcat gagcaactgg aaggatgcca ttgccaatac ctggggtggc aaggatatgc   15600
agaggaaaca gatttggggg gaacaccaag ggttcatttt tgcccatgtt gagtgtgaga   15660
tgtccacttg atatccaagt ggagatcaaa tggaggagag aaaggggtct ggtctggtga   15720
tacgctttta gaaattacca gtatataaat atttaaagcc cagagacaaa gagatcataa   15780
agggagtact gacagagaag agaagggatc agcagactga gctttgaggt gctacaataa   15840
ctgagagttc tagaaaaaga ggagggagcc ccagagggga cttgaaatgg agcaacaaat   15900
gaggctgtct tgaagatggc attcaccagg cagagagtag ggaaagaatt ctaggtgagg   15960
ggaagggtgg gtacccagac tcagaggtac aaaagcctga tctgggagag ggacggggaa   16020
gatagtaagt ggtgtggtat ggggaagagt agagtagagg ctgcaagatg ggcttctttg   16080
acatgtaagg gacttggacc ttcaatggaa gactttggga gttaatttct tgataattat   16140
gaggaagttg atggcagcta agactcattg acgtattatt ctaacttatt attctagcat   16200
gtgtcaagca ctgtgctaag caaattacat acattatctc acttaatctt tacacctacc   16260
ctttaagaaa gatagtagta ttatcctctg cagatgaaga aatgggctca gggggtcaaa   16320
gttatcagtg agtaaactgc cttaaccca ggtagttcca ttccagagtc catccttta   16380 accactaacc tgtcctgtct ccttgaggtc tggcacttct taaccaggtc tcagagggtc   16440
agcctgagag catgtgtcat ttccccatag aggacctgac ttcactgttt ctcagatgag   16500
gtgctttacc tgcaaagggt taaggtagat tctgggcacc agtgaaggag ttcaagtgga   16560
ggagcaactt gacaggattt gcttgtgtag gatgttgatc tggcagcagt gtggtgaaca   16620
gagtgcatga gggtgcctgc tagtaaggga gatctatttg gggaagatta gctcaatgtg   16680
agacctattg aggggcctga gggctgatga agcagtgtgc ttcaggctgc agggtcaggg   16740
tcttagtaag agatgagcta gatttgagag tcacgtggct gcaaatagaa tcagtggttc   16800
tgagggaggg aagcaatttt cagatattca ctgtccatat atacacactt ttctcaaatg   16860
gatcccttag agaacaggga aaatgcacac ctcttgcact tccatcatct tcctatggtg   16920
tgtttgggaa ggtaaaaaaa aacctccggg acccaaacct aggtccaatt tcaaatataa   16980
tgcatgtagg agaatgtgaa tgactcaggg ccagtgacac ttcctttac aagtcagatg   17040 agtctggctg ttcgctttca acatacttga agggagacct aaacacacac acacacacac   17100
```

```
acacacacac acacacagac acacacactc tttagagata gggtcttacc atgttgccca   17160
ggctggagtg cagtggctgt tcacaggtgt gatcatagta cactcagcc tggaacttca   17220 agtggtcctc ccacctcagc ctcaaagggt gtgggattac agttgcacac cactgtgcct   17280
ggctgaacat aaggatagat tacaacgtga tttggggcta tgactttcaa ggatttcaaa   17340
gatttgagtg acattgctgt agctaaaata cttccattct tttatttatt taaaaataat   17400
ttctcagtta ttgtatctat aaaaagaaca gtagtgatat aattatacca atggtttcat   17460
tataataata agtcatccac aaacccatta actaataata ggaaaataaa cccagttcat   17520
cgcattaatc tcattaaaga atgtatttcc aataaaactt tatattgaat gattgtcaaa   17580
gtttataata tacttatgat gttttgatta attgtgtact atgaataact ggaatttact   17640
actacttaat ccagaggaat ttttctttgt ctacctagag gattatggtc acaattttt   17700 ttttctattt taaatcttaa tttatgtcca tagttttgtg gatgagatct atgaatgggt   17760
tattaataaa aggttttgt ttgtttgttt gtttggtttt tttttgagac agagtctcac   17820
tctgtcatcc aggctggagt acagcagcgt gatctcagct cactgcaacc tccaacttcc   17880
aggttcaagc gattcttgtg cctcagcttc ccgagtagct gggattacag atgctcgcca   17940
ccatgcccag ctaattttg tatttttagt agagatgggg ttttcccatg ttggccaggc   18000
tggtcttgaa ctcctgacct caggtcatcc gctggcctca gtttcccaaa gtgctgagat   18060
tacaggcatg ggccactgtc cctggccaat aaaagctttt gaagcataaa aacaaatttc   18120
atttataatt ggtgggtaaa acaaaaactt gcatccaaat gtttgtagca gccttattca   18180
taataaccaa aaagtggaaa caattcaaat gtccaccagc tgatgaatgg ataaacaaaa   18240
tgtggcatat ccatacaatt gaatattatt ggacagtaaa aggaatgagt actgattcat   18300
tccacaacat ggatgaacct tgaaatatta tgctaagtaa aagaagccag tcacaaaaga   18360
ttacatatta tatgattcca tttgtatgaa atgttcagaa taggcaaatt tatggagaca   18420
gaaagtagat cagtggttgt ttagggctgt agtaggggag gggacaatga ggaatgagtg   18480
ctaatgggta ctaggtttat ttttggggtg atgaagatgt cttaaggctg attgtaccaa   18540
cgattgcagc tgtaaatatg ctgaaaacca ttaagttgca ttctttaaat ggataaatta   18600
tatggtatat gttttgtttt gttttgtctt gttttgaga cagagtctca ctctatcacc   18660
caggttggag tgcagtggcg cagtctcagc tcactgcaac ctctgtctcc tgggttcaag   18720
tgattctcct gcctcagcct ccccagtagc tgggataaca ggtgcacacc accatgcctg   18780
gctaatgttt tgtatttta gtagagatgg ggtttcatca tgctggccag actggtctcg   18840
aactcctgac ctcatgatcc acccacctca gcctcccaca gtgctgagat tacaggcatg   18900
agacactgtg cacagccagt atgtgtttta tatctcaata aggctgttaa aatatctgtg   18960
ggaggttggg cacagtggct tatgcctgta atcccagcac tttttttttt ttttgagatg   19020
gagtcccgtt ttgtcgcaca ggctggagtg cagtggcgtg atcccggctt actgcaacct   19080
ccgcctcccg ggttcaagcg attctcctgc ctcagcctcc caagtagctg gactacaga   19140 agtgcgccac catgcctggc taattttttg tattttagt agagacgggg tttcactgtg   19200
ttagccagga tggtctcgat ctcttgacct cgtgatccgc ctgcctcggc ctcccaaagt   19260
gctgggatta caggtgtgag ccaccatacc cagcctaatc ccagcagttt gggaggccga   19320
ggcaggagga tcacttgagg ccaggagttc aaaacaagct tggcaacat agtgagaacc   19380 cagtctctac aaaagaaaaa gtaaaaagtt agctggatgt ggtggcccat acctgtagcc   19440
```

```
tcagctacct gagagtctga ggcagagaat cttttgagcc caggagtttg aagccacgtg    19500
agctaccatt gcaccactgc actccagcct gagcaacaaa acaagacctg gtctccccca    19560
acctcctccc ccaccagaat tctgtggagt aagtgaatga aaacagaagt taaagcagat    19620
ataagaatga tacaatattc tgactataaa agaagatctt gtacatttac aaaacactat    19680
caattcattg caaccattta aatttgggat tatagctact tgggaggctg aggcagttgg    19740
attgcttgag ttcagaagtt tgagactaca gtgagccata atcgcccac tgcactctag    19800 cttggatgaa gagtgagccc cgtcaagtaa ataaataata aaataaataa ataaataatt    19860
tggatgtcaa atcagaaatt gcataggagg gccgggctca cgcctgtaat cccagcactt    19920
tgggtggccc aggtgggcag atcatgaggt caggagatca agaccagtct tgccaacaag    19980
gtgaaaccct gtctctacta aaatacaaaa aattagtcga gcgtggtggt gcacacctgt    20040
agtcccagct actcggaagg ccgaggcagg ggaatcgctt gaacccggga agtggaggtt    20100
gcatgagcca agatcgcgcc actgcactcc agcctggtga caggggggaca ctctgtctca    20160 aaacaaacaa acaaacaaaa agaaattgca taggaatatg tagttttgtt tttgtggggt    20220
tttctgtttt gttttgtttt tttgagacag gatctcgctc tgtcactcag gctggagagt    20280
agtggtgtga tcccggctca ctgcagcctc cacctcctgg gttcaagcga ttctcccacc    20340
tcagcctcct gggtgtctgg gaccacaggc ctactgccac aaaaccgcct gcctcggcct    20400
cccaaagtgc tgggattaca agcgtgagcc accgtgcgca gccctgtagt ttttatttta    20460
ggagattctt aagcaaaaaa gcctgaagcc cagagaatta aatctcttaa agagaatggc    20520
tagattaaat gagaaaagag gactaaagaa ggaaaatttc agactagccg atgtggcaaa    20580
accctgtctc tacaaaaaat ccaaaaatta gctgggcatg gtggtgtgta cctgtagtct    20640
caggtatgca ggagctgagg caggaggatc actttgacct agtctcattt aaaaacaaca    20700
aaaacaaaac aaaacaaaa aggaaagaga gaaaattagg aatactagca tctaaagaaa    20760
atgcaggaga aatggagaag taggactaga accacagaag gactgtttac agctggaggg    20820
tagtgtcaag catccctcag gattgtggaa gctcaggact caaaatcatc tgtgattggc    20880
aattatgaag tctttgactt tggcaccacc catttcagtg aattaattgc agtccagcac    20940
agagactgat ggctgggaac aggagttcag agaggttaga ggcgagaatc agagggagga    21000
agtgaagaca tcaactgtga actactttct tgagaagtta gaacagaaat aatacggcag    21060
tagtttggta acttttggga gaagtggtgt aaaggtagtt gttactactt tgaaaacgag    21120
attgatttga acataaacca aaggtaaaaa gctggtgagt gagagagagg agggatgctc    21180
atttctgttg tatgcaaaat gttctgcaaa tcagctagcc ttggctgtga cccctgggaa    21240 gccgagggg atgccatccc ccttacttca gaattgtggc ctttctcttc tggtgagcta    21300 ggaatttat tcagtacttc tcgggaattt tacaaactct tatctaggca gtgagccact    21360
atcttgatac tcagttttcca aaaccgcttg tttctacaga gctcatttcc aatgttgcca    21420
atgtttagtg ctacaacagg gatggggtg tggatggacc aacaggctag ctcaacattc    21480
ttttgaattt gggttaagtg actgatttag ggtaagagtg gctcccaggg ccaggcgcgg    21540
tggctcacgc ctgtaatccc agcactttgg gaggccgagg cgggcggatc acaaggtcag    21600
aagatcgaaa ccatcctggc taacatggtg aaacccgtc tctactaaaa atacaaaaaa    21660
ttagccgggt atggtggcgg gcgcctgttg tcccagctac tcgggaggct gaggcaggag    21720
aatggagtga acccgggagg cggagcttgt agtgagccga gatcgcgcca gtgcattcca    21780
gcctgggcta cagagtgaga ctccgtctca aaaaaaaaa aaaaaaaaaa aaaaaagag    21840
```

```
tggctcccga atttcttggg taggagtaaa aaagatttta cggtattttt ttttctcacc    21900
ttagttcttt agaattatgc tggaaggaac caattcacct caaataccaa ggaaatgggt    21960
gtgatgtagt aggcagagga gtagccttt ccatactgcc agcagaatgg agacagacct    22020
gggctcgcac acaccacccg gacccaggag tgggtggttc aatgtgtact gttaagacta    22080
aagaaggttg gccaggcgtg atggctcatg catgtaatcc caacatttg ggaggccaat    22140
gcgggcggat cactcgagcg caggagtttg agaccagcct gtgcaacatg gcgaaactcc    22200
atctctacaa aaatacaga aaagctgggt gtgttggcac gcacctgtag tcccagctgc    22260
tctggaggct gagttgggag aatcacctga gctcaggagg ttgaggctgt gtgagccatg    22320
gttgcaccac tgcactccag cctgggcgac agagaccctg tctcaattaa aataaaaaag    22380
aaggtcatgt gaaagctcac tgtgaacagg acttttttt ctctgtaggt gcttcattgt    22440
tacttcagtt tacttgaact catttcattg ttttcacact gttatgaaat gctctcaaca    22500
ataactgcaa caacaaatag agaagaaagg aagtatttag taatatcaag agagggccgt    22560
ggttagcatg agacatcttg cgttattcac cactgcaatg agaagaaaaa gactgagcaa    22620
agggaatttc atccatttct caaggattta gagagctaca tgctccattt gaaggtcaca    22680
ttgtacatgg tgaggtcaca ttaagggaat tgacttcctc ctctaaatcc ccctgatctt    22740
tatatatttc tttccatggt tttatgctaa tactttgaag aactgaagaa tgttatgagg    22800
tggccaggga atgctatggt tccaggtaaa tgtattttca aggtctttgg cagtcggtaa    22860
accattttcc aggacacact ttggtgtaag catactagta gtaatagtaa caagtattag    22920
caggaaaaac tatcttagtt ttttgaattt atacttaata ttgttattgt tcttaccttg    22980
ttttatagct gagatattaa gttccctgct gtgtgctgag ggcattgaga acccaaagat    23040
aaagaggaca cagcccctct aaaaaccttt ctagggccct gtggctcctt gtccttgggt    23100
ggaattcagg ggccctgtga actttatag gaaaagatta cagttttatc accctctaac    23160
tgcaatacag tatttccttc agttatcaat ggtaatgaca agccacagga gtgacagcta    23220
ttcccattta tacatatcac tactttgaaa taatggtagt catttgattt accactagat    23280
caataacaag gcacatatgg tatgacagcc aataaatgtt tgaatagttt gataactgta    23340
tttcataatt agttttctgc atatgcctat gtctatttta ccatattttg agaaggcttt    23400
aggaggcaca aaaaaggtt aagaaccct ttctgtttac tatctcatga ggaaggctag    23460
aagcttcaac agataaaatc agtacaaagt ggtgagtggc agctagaaac atgctcagga    23520
gctgtggagc acaggcttga gcagagattc agggaaggct gatggagaag attcctgagc    23580
tgcatctgga atgaagaaga aacagaagca ggaaaaggtc attcccagga gagaacagaa    23640
cagatcttag gcaggaaat ggcctatgtg gaaggcgggt actgacagtc agagcttgct    23700
tactgtgcta agtcttgggg gctcaagaat gaatgaggga cctcctaggt ggtcagtgtg    23760
ctcactgttc agaacaatgt ttatggggac agggtggaga ggggtatagt ttgaaaaagg    23820
aaatttttt tttggacacg gagtctcact ctgtctccca ggctggagtg caatggcatg    23880
atctcggctc actgcaatgt ctgcctccca ggttcaagcg attctcctgc ctcagcctct    23940
cgagtagctg ggattacagg tgtccaccac catgcccggc taattttgt atttttagta    24000
gagatggggt ttcaccatgt tggccaggct ggtctcaaac tcccaacctt aggtgatccg    24060
ctcgccttgg cctcccaaag tgctgggatt acaggcatga gccactgtgc ctggccgcct    24120
ttctagaatt ttatatgagt ggaatcatac accatgtgct cttctctttg gtctggcttc    24180
```

```
tttcacatgg cataatgcat ttgagatttg ttcatgctgt tgcaaatcaa cagttcattc    24240 ccaattttt  tgccaagcag tatttattat agaattatat actctgaaaa ggggaaaaaa    24300
accaaccttt gttttcataa aacaaatttt taaaaaggag tgagatttt  aatgcttatc    24360 aaatgggaat atgagttaaa aattgttgag aaatgctgct ccagcatgtg gtcagagagc    24420
attccagccc aagattttct tatgtcaatg ctaaatttga gcacatttgg aagtatttta    24480
gacctgaaag aaggcaggac atcaaaacaa ccactagagc cgagtgggcc tttgtaacca    24540
cagactctct gacgaaaaga tttgtaaaga ctctgcctaa tgaagagttc aaaaagcatt    24600
ttgtgtgtca tctgtttttc ttacagtctc cttacttggt agataagggg caagaattat    24660
tttccatgtt gcataaatag gaaatgaggt atagcgagtt tgagatactt attacccaag    24720
atcccaggga gtcagaggca gactgaggac tgcaaaagat ccctcctggt ccacaatctt    24780
agccttgcca gtaggctggg ctgaaagctt taaaaaaaaa tacagtaatt tcactttcac    24840
ttttgttctt gtttggggttg tgatacaatc tttaatttga aagaatgaag ggttttcttt    24900
tccttctttg tttttaaaac tttccccctct cttcttggta aacaccaaca tgtgtgttga    24960
ctctatccag ttgaactcaa caacctaatg cctgttttgt gccaggctct tttccaggca    25020
ctaaggaggc actgatctgg acaaatcctg gaggttactg tgaagcagga aggacaaaat    25080
gaccaaatga gaattaaatt actttttag  ggtcgtggaa gatttgaaaa tctgggaaa     25140 catatgtgtc ctctttcccc caaaaaatgc acatagtgtg tacacacaca cacacacaca    25200
cacacacaca cgtgtgtgtg tgcgcttggg ctcacatgat tttgcaatga ttttagcgtg    25260
tttagagacc ccccagaact tgtgtgtagg attggccttt ggatgagtat ttttggcata    25320
gaatgaaata gtaatgcctt gaaggcagca caaagccata gtcactgaat agagagaaag    25380
attcagagga tcctgtgaga tgggtggggc tgttagtgtt ttgatagaca cgtgtactga    25440
gttgggaggg tactaatttc tggaaggcaa tattccaggc agagggcaca tctgagaaag    25500
gtaggagggg agggaagcag aaaaatgcaa agcaatctga gaaacccagt ttggctggag    25560
gatagattat atgaagagca atcttcagaa acacccatag aaaggtaggc aggggtcata    25620
ttgtgagtga tactgagtaa gcaaggtgag tagtcttctt tttattctcc ccagtaaaat    25680
attctgcagt tccttttatt tttaattaga tggcaaaacc ccatctctat caaaaaacac    25740
aaaaattagc cgggcttggt ggtgcatgcc tgtagtccca gctacttggg aggctgaggc    25800
aagaggatca cttgagagtg agctgtgatc atgccactgc actccagcat ggctgacaca    25860
gcaagatgct gtctcaaaaa tatgtatata ttatatacag ttttctgttg ttgtttgttt    25920
ggtttttttg gagatggagt ttcattcttg ttgcccaggc tggagtgcag tggtgtgacc    25980
tctgctcact gcaacctccg cctcctgggt tcaagtgatt ctcctgcctc agcctcccga    26040
gtagctagga ctacaggtgt gcaccaccac acccagctaa ttttttatagt tttagtagag    26100 atggggtttt accatgttag tcaggctggt cttgaactgc tgacctcagg tgatccacca    26160
accttggcct cccaaagtgc taggattaca ggcgactggc ctttttttt  tttttttt     26220 tttgagatgg agtcttgctc tgtcacctag gctggagtgc agtggcacaa tctcggctca    26280
ctgcaacctc cgcctcccgg gttcaagcga ttcttctgcc tcagcctcat gagtagctgg    26340
gactgcagtt gcgtgccacc acacccagct aattttttgaa ttttttagtag agacgggggtt   26400 tcaccatatt ggccaggctg gaggttttttg tttgtttttt ttttttttgag atggagtctc   26460 actctgatgc ccaggctgga gtgcagtggc acagtctcag ttcactgcaa cctctggttc    26520
ccgggtttaa acagttctcc tgtctcagcc tcctgagtag ctgggactac aggtgcatgc    26580
```

```
caccaagacc agctaatttt tgtatttta gtagagatag agtttcacca tattggccag   26640
gctggaggtt ttttttttt tttgagatgg agtctcactc tgatgtccag gctggagtgc   26700
agtggtgcaa tctcagctca ctgcaacctc tgctttccag gtttaaggaa ttatcctgtc   26760
tcagcctcct gagtagctgg tacttacagg cacatgccac cacgaccagc taattttgt    26820 attttagta gagaagggt ttcaccctgt caccatattg gatggggttt caccatattg    26880
gcctcaaact cctgacctca ggtgatccac tcacctcagc ctcccaaaag tgctgggatt   26940
acaggcatga gccactgagc ctggccaaat cagttagttt tgctagtaa caattccccc    27000 taccactaaa atttcatggc tttaaacaat catatattta gcttgtgatt ttgtggtcag   27060
atgattctag tctgggcagc tcagctgggt agctgatgtc ttctgggctt gtccccatgt   27120
ctggagccaa ccaatgggtt agatggtggc caggtgatcc aggaaggctt cccttatgtg   27180
tggccactgg ctaagagcct tggtgctcct ccatgtttcc actcctctag caggctagca   27240
cgggcttatt cacatggtgg tcttaggat acaaatgcaa gcaggagagt aaacccagag    27300
cacaggtgaa ttaaagccac tgcttgcgta catttgcttc acaagtcaca tggccaacta   27360
aaatgcaggg gcaggaaata gactcaactt tctgatggga agaactgcaa catcacattg   27420
cagggatgtg gaagggagaa cttgtggtgg tttttgtaaa ctacctcacc tggtcattga   27480
atacattgat tccacagtat atgatagata caggcagcta acaaaatt ggattattgg     27540 ataaattatt ggccatatat atacatgtat atatgtacca tacttatttt gcaaataggc   27600
ttgaagcctg cctaggaaaa actgagtctt tttttctag cctatcttat ttttggatcc    27660
ttatattagt gatatatgga gcttaaatat tgcagaacta gtaacaaaat gttaatgtca   27720
atacctcaga aaagggagtt actgaagaat actgaactta atgtacagtt gaattaaata   27780
aagatagtag cctaagccaa atattattag actagtgaat gatagaaaca aaaagctaca   27840
aagaggtttg gtttgcatgt taaaaagtat cctatgcatg aaaccacttc acatctttat   27900
gcctcattgt catttccaat tagactactc tctagaatta tttcacattt ccaaaatggt   27960
tgaattagtt gggttacaat tccagctgca tacaggatta ttttacaggt aagctagcca   28020
tatctgggtt acaaaacagt gtcagaaata tggtgaatgg tgtttaccat tcttgcactc   28080
atatatctac acatgcagac taacagtgat gggacatgac ttatgcacca ggcattgtaa   28140
tacagagaaa aatcagacaa aaccctctcc ctccaggagc tcatatgctt tgtgagggag   28200
agagatacat aagtacagtt ccagagataa gtgctagtaa aattttgcag atgatactac    28260
agagcctaga tttttttttt tttcaagatc tctctctgtc actcaggctg gagtacagtg   28320
gtgcaatcaa ggctcacagc agcctcaacc tcctgggctc aggtgatcct ctcacctctg   28380
cctcccaagt agctggaacc acaggcgcat tagcatgcct gtctaatttt ttttttttt    28440 tccgagacag agtgttactc tattgcccag gctggagtgt agcggtacga tctcggctca   28500
ctgcaacctc cgcctcccgg gctcaagcaa ttctcctgcc tcagcctccc aagtagctgg   28560
gattacaggc atgcgccacc acgcccggct aatttttata ttttaataa agacagggtt    28620 tcaccatgtt ggccaggctg gtcgcgaact cttgacctca tgatccgcct gcctcagcct   28680
ctcaaagttc tgggattaca ggtgtgagcc actgtgcccg gccctaattt ttaaagtttg   28740
gagagataga ctctccctac gttgcccagg ctggtctcaa actcctgggc tccagtgaga   28800
cttccacctc agcctgccaa agtgctggga ttacaggcgt gagcccccat gcctgggcca   28860 gattttaac attggctttt tttttttttt tttttttttt ttttaagat tgagttttgc    28920
```

```
tcttgttgcc caggctggag tgcaatgtcc tgatcttggc tcaccacaac ctccacctcc    28980
tgggttcaag cgattctcct gcctcagcct cccaagtagc tgggattaca ggcatgtgcc    29040
accactcctg gctaattttg tattttagt agagacggag tttctccttg ttggccaggc     29100
tggtctcgaa ctcctgacct cagatgatcc acctgccttg gctcccaaa gtggtgggat     29160 tacaggcatg agccaccacg cctggcctaa cattggtttt ttatattagt aatgacatag    29220
caagtcactc tggaactttt ataaaggaca tctgcccagg tattaaccct ggagattctc    29280
attcattggg tatggagtgg ggaccagatg gctgtatttt ggaaaggcac aaatgatact    29340
gagaggtact tctaagaacc attgctttat aaaatgttag tgtggccggg tgcggtggct    29400
cacgcctgta atcccagcac tttgggtggc cgaggtgggt ggatcacctg aggtcaggag    29460
tttgagagca gcttggccaa catggtgaga ccccctctct actaaaaata caaaaactag    29520
ccagacgtgg tggcgggcac ttgtaatctc agctactaga gaggccgagg ccagagaatc    29580
gcttgaaccc cggaggcgga ggttgcactg agccgagatc gcgccactgc actccatcct    29640
gggtgacaga gtgagactct gtctcaaaaa gaaaaaaaa tgatgaaaga taggtttatt     29700 ggttttttt ttttttgag atggagtctc actctgtcgc ccacgctgga gtgcagcggc      29760
gcgatctcgg ctcactgcaa gctccacctc ccgagctcac accattctcc tgcctcagcc    29820
tccggagtag ctgggactac aggtgcctgc cactacgcct ggctaattgt ttgcattttt    29880 tttttttt tagtagagac gtggtttcac catgttagcc aggatggtct ccatctcctg      29940
acctcatgat ccgcccgcgt cgacctccca aagtgctggg attaggttta ttgttttaaa    30000
gaatagtttt attgagatat gattcacata aatgtaattc acccacttaa agtgtaaatt    30060
cggtggtttt aaatatagtc acagaattgt gcaaccatca ccagaatcaa ttttagggca    30120
ttcttattgc tccacaaaga aacctcgtgc ctattaccag tcactcccca catcttctca    30180
actcgtccag tcctaggcaa ccactaatgt actttctgtc tccagatttg tctctcctgg    30240
acatttcata taatatgtgg tcttttgtga ctggcttctt cctttctcgc ttcccctccg    30300 ctccccctccc ctccgttccc ctcccctcca ctccactccc ttctccccca ctcccctccc   30360
ttcctctccc ttccccctccc gtttcctttt tgatggagtc tccctatgtc acccaggctg    30420
gagtgcagtg acgcgatctt ggctcactgc aacctctgcc tcccggattc aagcaattct    30480
cttgcttccg cctcccaagt agctgggatt acaggtgtcc accaccacac ccagctaatt    30540
tttgtacttt tagtagagat ggggtttcac catgttggcc aggctggtct tgaactccca    30600
acctcaagtg atccacccac ctcagcctcc caaagtgctg agattacagg tgtgagccac    30660
cacacctggc ctgactggct tctttcacat agcataatgt tttcaaggtt catccgtgtt    30720
atagcatgtg tcagttcttc attctctttc atggatgaat agtattccat tgcatgaatt    30780
aaatgtagta caatttgttt atctatttct catttgggtt gtttccagta tttgcccaat    30840
atgaataaga atgatgctgc tggccgggcg agatggctca cgcctgtaat cccagcactt    30900 tgggaggct gacggggtg gatcacctga ggtcaagagt ttgaaactag ccttgaccaa      30960
catggtgaaa ccccgtctct actaaaaata caaaaattag ctgggcgttg tggcatccgc    31020
ctgtaatccc agctactagg gagactgagg caggagaatc gcttgaaccc gggaggcaaa    31080
ggttgcagtg agccgagatc gtgccgttgc actacagcct gggcaacaag agcaaaactc    31140
catctcaaaa aaaaaaaaa aaaaaaaaa gatgctgcta tgaacagtca tgtacaaatt      31200
tttatatgga catatgtttt catttctttg ggtaaaccct taggagagga attcctaggc    31260
gacatgagaa ttttgtttcc tcttttgaga aactgccaaa cttttccaaa gcaaatgcac    31320
```

```
cattttacat tccatcagca gtgtgagagc tccagtttct tcacattctc cctaacactt    31380
gttatttgtg attttgatta tagccaaaga tagattttat tatccccatt tttaagataa    31440
ggatatcatg gtttagagca gttgtcaggc catagacagg tactttgcac tctcagacac    31500
tggacctcat ctgccatagc actttgaaat gaccttataa taattgaaag aggaaggccg    31560
ggcatagtgg ttcacgcccg taatcccagc actttgggag gccgaggcag gtggatcacc    31620
tgaggtcagg agtttgagac cagcctggcc aacatggtga aaccctgttt ctactaaaaa    31680
taccaaagtt agctgggcgt ggtggcgggt gcctgtaatc ccagctactt gggaggctga    31740
ggcaggagaa tcgcttgaac ctgggaagtg gaggttgcag tgagtggaga ttgcaccact    31800
atgctccagc ctaggcaata agagcaaaac tccatctcta aaaaaaaaa aaaaaaaaa    31860 aggaaataat aataattgaa agaggaaaac atggaactat atatggaatt gtttcaaat    31920 actttagtat ttttttccaga attaatgggc aatttaatat ttcatataat tgacttctgt    31980
aaatgactgg tattccttttt tttttttgaga tggagtctca ctctgtggcc gaggttggag    32040
tgcagtggtg caaccttggc tcactgcaat ctctgcctcc caggttaaag caattctcct    32100
gcctcagcct cctgagtagc tgggattaca ggtgcctgcc accatgcctg gctaattttt    32160
gtatttttag tagagactgg gtttcaccat gttggtcagg ctgctctcaa actcctaatg    32220
tctagtgatc cacccacctt ggtctcccaa agttctggga ttacaggtgt gagccaccac    32280
gcctggccaa ctggtattcc ttttataaaa tacgtatctg acttattttt gttgcctcat    32340
tacatcaaga tttacatcca agttaaattt gtatagatta taggtaatca agtgtggtaa    32400
gcacctactg aaatgtttaa aaattttaga atttccttac tgtcaaaatg ataattcttt    32460 ttttttttg agaagggtc ttgctctttc gcccaggctg gagtgcagtg gtgcgatctt    32520
ggctcactgc aacctccgac tcctgggttc aagtgattct cctgcctcag cctcctgagt    32580
agctgggatt acaggtgtgt gccactatgc ccagctaatt ttttgtattt ttagtagaga    32640
cagggtttca ccatattggc caggctggtc ctgaactcct gacctcaggt gatacaccca    32700
ccttggcctc ccaaagtgtt gggattacag gtgtgagcca ccgcgcccca ccaaaatgat    32760
aattcttaac cagaggaaat agacaaatga acagaaactc acatggaaag gtttgttcca    32820
ggggttcaca ttcatgattg ttcatcagac ttcagagctt taaaaaatag aatacaggtg    32880
cacaggctct accccagatt aagtgagtca ggatctttgt ggttggctct ggggtgtctg    32940
catttgtaaa aagctcccca gctgattctg aggctcagct gaggttgaga atcaatggtt    33000
tgtgtgactg agatggttgg cagtatgaag atgttttga gaaatttact ggcagaccta    33060
gctgggcatc cagcttgatt ggtctgttgc atggggtgga aaagatagtt ggggtggggg    33120
tatgggtgtc tttggcagg tgggagatgg cagtgcaggt aatgcagaaa aggaatttaa    33180
gtaaagtagt gtgtgttttt gaagccaatg agaagcttcc ttataaagaa ataatattca    33240
tatgctgtaa ctctattccc acctcaactt gttttgaaaa ctttaaatct agagagaagt    33300
tgaaataaag gtacaatgaa cacctgtatt gtttttatct aggttcacca gttaacattt    33360
tgctgtatta acactggctc ttcctcccaa ccccctttct aaaccatttg aaagtaagat    33420
gcagtcactg tggcctttgc atttaagtaa ctgtgaagaa taggaatatt ttcctacata    33480
accataatat aattattaca taatgaaatt taaccttggt attataccgt taccgaacat    33540
acagtctata tttgctcttc atagctcttt ttttttttt ttgattccag gatccagttg    33600
aaaatcaggc attgcatcca gttatcatgg ctttaatctt aatgccttcc ctgcactgtt    33660
```

```
ttgggaatat cttaatactg ctattttttga agagtccagc tcagttattc tgcagaatgt   33720
ctgttgattt ggctttgctg tttcctcata agtagatcca gattatacgt ttttgttgat   33780
gttgggttct tctcagtgaa tcacatccga tgatgtcagc acgaggcctg atcatttggt   33840
ttaggtagct ttcactagac tttttcattg taaaggtacc tatcccttttt ctaattaata   33900 agtaatatgt tgggtgatag tttgtgtgtg aatatccttt tctccagtga cctttcatcc   33960
aatggtttca gcattttaaa tgatcctggg ctgagtcagt tttcagtggt ggctgcagac   34020
ttgtggtttt ccaattcttt catcactttt acatttatta attggcagtc tatgacttct   34080
tatagccaca taaagataat tcaggaatta tctgaaccta tgaatgttac cttatttgga   34140
aaaagagtct ttgcagatac aattcaatta agaatcttga gatgaggaga ttatcctgga   34200
ttatccaatg ggccctaaat ccaatgacaa atgtccttgg cagagggaga tttgagacag   34260
gagaagagaa gacacgaagg agggaaggaa gtgatgtgac cacagaggca gcgattggag   34320
tgatgtagtc acaagccaag gagcaccaac agccaccagg agctggaaga gcccaagagt   34380
atatactaat acctggattt gggacttggg acttctggtc tctagaagta ggaaagaata   34440
aacatctgtt ttttgtttgt ttgtttgttt tttctttttt ttgagtcagg gtcttgctct   34500
gtcacccagg ttgaagtgca gggggtgtgat cacggctcac tgcagccttg acctcctggt   34560
cccaagcaat ccaactcatc tcagtctctc gagtagctgg gagaccagcc accaaaccca   34620 gctaatttttt gtatttttta tagagatgag gtttcacacc atgttgcaca ggctggtctc   34680
gaactcctga gctcaagcga tctgcctgcc ttggcctccc gaactgcagg gattacaggc   34740
atgttatttt aagccactca gttttttacta cagcccacagg gaagcaatac aaaggtcaag   34800
ggaattttct gttttttaaaa tatggaggcc aggctcggtg gctcacgcct gtaatcctag   34860
cactttggga ggttgaggtg ggcggatcac ttgaggtcag gagttcaaga cgagcccaac   34920
caacatggtg aaaccccccgt ctctactaaa aatacaaaaa taaactggac ttcatggtgg   34980
gagtctgtaa tcccagctac ttgttcaaga gaatcacttg aacccgggag acagaggttg   35040
caatgagcca agatcgtgcc actgaactcc agccttggtg acagagcaag actccatatc   35100
tctttctctc tctctctctc tctctctata tatatatata tatacacaca cacacacaaa   35160
cagaagattt ccagcacacc agaaaggcat tctttctctg ttttgtatat atacatatac   35220
acacacacac gcacacacac acacacacag atacacacac acatatatac atacacacac   35280
acacacacat atatagatag atacacacac ttacacacac acaaacagaa gatttccagc   35340
acaccagaaa agcattcttt ctctgttgtt ttttttttcca tttatgtatc tcagacaggt   35400
ccaataactg gatctggaaa gactggaaat cttccttttg tccctctgtt tccctctcc    35460 acacttctcc accctgccct ctcctggggg agtctggccc ttatgaacca catcaaagga   35520
tcctctggct tccggttggg tttggccagt gggggaaccccc agcaggtaga ggggaggtgg   35580
agagcttggc tgtgtcctca agtagaaggc cactggttct ctcagcatgt cctctctaca   35640
tgcatgtcag ggtccccatg accactcctt tcttgcatcc ttaaggcctt ggagtagaca   35700
gcactgcttg ctagccccag gaacctgcac ttttccttgg ggttttctgt accgtatctg   35760
tatttacaaa tagcatcttt actaaatcct cttggaatta tgcagagttg aatatgccat   35820
ctacttctct gtggggactc tgactggtga tgcactttga aaggacagaa aaccttgagt   35880
ctctggacat ttctacagtg tttcacattc agcattgctg gtattgtaga taaatacctg   35940
tcgggtagtt gtatcatttt catgctcaat tattttttcag caaaagctct ttggactact   36000
attaatattc aatgtctttg tgttttctct tagatctccc taagtctcat atcttatgct   36060
```

```
atttgctaaa tgattatatt cttttttaaa aaaattttta atttttttaat ttttttttcta    36120 attttttcatc actctcagga tgtgattaca ttctttatct attaatattt tctttttttct    36180 tccacttctt gcccacaagt atcatcttga tcatgggtaa ataattgcat taatttaaaa    36240
atttcagctt atagtcatat gatgtttttt tcctcctaag aatttcagga aacaacatat    36300
tgtcctaagg tatttgtata cgtgtcacgg tcacttgttt ggtaattaaa tactgtgtcc    36360
tttgaatgcc tgtggaaagc tgtcttccct gatatttctc tctcaagata gccatgagcc    36420
cacaattctg attatcagtg cagagcgggg ccccaacttt ttattcttta tttttatttt    36480
agagatggag ttttgttctg tcgcccaggc tggagtgcag tggtgcagtc atggcttact    36540
gcagccttga actcctgggt tcaagcaatc ctcctgtcgc agcctcctga gtagctgggg    36600
ctaaaggtat gtgcaaccat acccagctaa tttttttttt ttttttgagac agagtctcgc    36660 tctgtagccc aggctggagc atagtggaat gatctcagct cactgcagcc tctgcctccc    36720
aggttcaagc aattcctctg cctcagcctc ctgagtagct gggattacag gtgcacacca    36780
gcatgcccgg ctaagttttta tatttttagt agtgacaggg tttcaccatg ttggccaggc    36840
tggtcttgaa ctcctgacct caggtaatcc gcctgcttca gcctcctaaa gtgctgggat    36900
tacaggcgtg agacaccgca ccagcctttt ttattttttat tattattatt ttttgagaca    36960
gagtctcact ctgtctccca ggctggagtg cagtggtgcg                          37000

<210> SEQ ID NO 5
<211> LENGTH: 30748
<212> TYPE: DNA
<213> ORGANISM: Homo sapiens

<400> SEQUENCE: 5
catgagtctg agcttctgct aaatgccttt tctaatttag ttttttcaaa gttttttgagc       60 gttcttttgg gttattcaat aacatggggt ttcctgatat tgtcttattc tctatttgtt       120
tttgttcttg tccctccaaa tgaattctaa atatctgatg gtcagaaaca gaattaattc       180
tcaataaaat tttataggta tgggtataag tgggcacgtt gttctctacc aaaccccctaa      240 acccaggaaa cagccacctc tagttgtccg gcacttggaa caacccttcc cagtgaaatg      300
atggaaagag gcacattcaa ggaaaaatgt tctgcattaa aatggtcacc tattttgctg      360
tgaacaattt gtcttgagat agtcttcccg atattcctaa gattcccccct tatttatcac     420 ttctctctct gcagatgttc agtctaccta tctctttctt ctccttactc tctctgcctg       480
tcccaaattt ctggttcccc taacttgcag gcctcacatt acctgaaact attcaaatat       540
ttatagaaca cctcttatgt gccagaccca ataccaggca ctaaaaatac agtcatgagc       600
aagatcaccc aacatacaca gagtaacaca gaacctacag agctttcagt ctagtgggga       660
aaacaatgaa aaacaaggaa tgacagaggg tggaggaatg cctgtgggca atgggagcag       720
agagcaggag taactgttcc tgcctggagg gctttctggt gctatgatgg gggatgagta       780
aggaattaag tgaacaggtg agaggatatt ctagagagag ctcgtgagac agaactagat       840
tgatttgttt aagcaactaa aaggaattcc atatccagtg ttacccagtg tgaggagatc       900
ttgggggtgg ggccggggaa gaaatagcca gctgagagtt ttaagctggg gagtcatgtg       960
attaaatttg cattttagaa ggctctcctc ccttcttcct gaggacagac tgaagaaaca      1020
tccaaggtgg tcttgaagga cactgggatc ctgtaacaca ggtaaaagat aaagactaat      1080
gtaatttcta tggggttgga gagaggtggt ctggtttgag aaatatttag gcaaaagcat      1140
```

```
aactgacagg acttggtggc tgataatagg tggtggtgtg ggagagagag tagcttaaga    1200
ggacacctgg tttctcatga acgtggctga aaggccagtc aggcctttcc tggatggtgg    1260
acatggtggg aggagcaggc ttgagtgtgg ggatgccaag ttaatcaaac tgaagttgga    1320
tattggattt gaggtgcctg ggagagagtg gagctcaaag gagagatcat ggcatctata    1380
tagatttgtg aatctttgga acagacagat agtaattaga gccatcagaa tgggtgagat    1440
aattaggaaa atatgagttc agccagaagc ctctcctcag ccccaccact tcagggacct    1500
gtaagcatgg cagcagctct gagtgagggt cagtgattcc agccgaggtg cagagacttt    1560
ttaatagcat tccctaaagt gtagttacac tgaaaaattg ttccccaaga gaaactacac    1620
acacacacac acacacacac acacacacac acaccacaca gttccatgct cagataagtt    1680
tggagaaatc tatatattat ttcccctgct tagagaatat taaggactga caagttctgc    1740
agtaaagacc ttttttacctt catttaattc agttttcccc acaagacagc cctggctgga    1800
gattactctg gatctgaatg tctcaggggtg aaggaagcgg gagacagcta gctttcccag    1860
aggcatgccc gcaagtcagc accgcagagt gcatctatct gttcatttat aagatgaaaa    1920
cattggggcc cagtgattgc ttccaagttt catagttagc tagtgataca tttgggttgt    1980
cacatactcc tttgacccaa tctaagaaaa ttccagtgat gcagcatagt gaaccagaa    2040 acacattttt caaatatat tgatcacagt gtttctcaaa aggccttctc tgtgaccttg    2100
aattttaatc ctacctctga catgtcttag ttgtatgagc ttgggcaaat tttctaacct    2160
ctttgagcgc ctgttttctt gtatataaat aaggatgtaa cagtaaccag taggattatt    2220
attaggtgtt accattaata aactgaggct gacagattga gacttgctca agatctcaca    2280
gctaaaagag ataaagctgg aactgaaact cagatctttg gctccaaatg tggtgtttcc    2340
tgtactaacc aaatcatttc taccagtgcc cctgggatta tgccttgggg actcaccta    2400 agacagtctt gctctcgaga cagagaagtc tgcaaatggt gtccaattca agtctagaga    2460
ctggctgaag ccagacagag ggagtatgag gaggggggcag agaatcttca gaaagacatt    2520
ccaaagtctc gggcctagaa aatgtttaga aatattggtt cctgtgttcc cctccagtct    2580
gtctacctga atgggaaact ggtggtgggg ccaggcatac ttcttttttga acaaatacac    2640 agttaattct gagatgccac cttgattgag aagcactgtc ctttctaag caaaaatcat    2700 tgccaaatta ccctagaatc caccactgct cacagatctg tgcctgaacc aacttggttt    2760
tgaagttttc ttttgtttca caaaactagt ttagggtggg ctgtgagagg aagcttctaa    2820
aaagccactg ggaaagtact aaatctctga gactaaagag ggcggactca gcctcacttc    2880
ctccttcttc tcatctgggc ttcctgtcgt cacagcatga tcatattttt tcacccttca    2940
cttctccttt tacacaaata gccccggata tctgtgttac cagccttgtc tcggccacct    3000
caaggataat cactaaattc tgccgaaagg actgaggaac ggtgcctgga aaaggtaagg    3060
ttgatgacgt tttaacttgg cttgctgtct aatgtggggt agggcgtatt cttaggggtc    3120
tccatatacc tctctagtaa ccataaaatc tccggcaact tctctttcac aaatatttag    3180
tgcacaaagt aaaacagatt agcaagatcc tagtaacatc cccaaaggca atcaggccag    3240
aaatactttt acttaatcag gttcccatta tctaaatctc tgagtcgagg cattcacatg    3300
ccttaattgc ttcagagctt gaattactct gtgtagtaat tcctgatgcc tggagctttc    3360
tatgcgagat gacattgggg agatttccta tgtgctctgg tcttcagaaa attggtcttg    3420
tgattttaaa gtgaggaaag aacccacagc cagagctgtc tttagaaaga cagctagaag    3480
acacagttct ttttcatttg agaaaatttc aaaagtaaat ttagtgactc ccactgtggt    3540
```

```
tcttcaaagc cactaaatag aaaggtggct aaaaatcaaa acaccaggat gtgctcagta    3600
actgtatttt aaaaggtgaa agctagacat ctctaaagga tgcatagatt gttggctttt    3660
aaggagcagg aagcacattg ggatcctcag catttcccca aattatcctt ggtgtacaaa    3720
acatgaccac tgataaatgt cacatgaaat gcacgtataa aatgcaatcc ccaaaacttg    3780
atactgcagt aatttccaat catgtgctgt aactaatgac tgaggttgca tggactcagc    3840
aaagtgttag cagagcttcg gtcctgactc tctgtgacca ccatcggaaa ctctatgtaa    3900
gagctttctt cttccaagac ctgtgagaat ttcacttgat tatgccctgg agcagaaagg    3960
agaaagttct ctttgattac acccacccat ctaagtatga ggattgggaa cagggcagag    4020
ggctctagat ttccaagagg ggtggggacg gggagagggc tctggattcc caaaacacct    4080
cagagtttat tgagccttgt attaaaaaat aaaaagcagt cttttaaata aattcactta    4140
ataatcaagt ggtaggtgcc tcctgaggcc aggcactgtg ctttgggaat tgtggggag    4200 ggagatgaaa aggtagaagg agaatatttg tctagcaaac agtcctactc ttaaggaact    4260
cccatgggag ataagagata tcatactatg cgtgtgcttt ggaagaaagc tgagaaaaag    4320
caaactccca gctgctggac aaacaaagag gttttgcttt ctcaatcttg aggagaatct    4380
gtactatttt gaaattgtgg ttgaatggga gcaaagactg aactgaaaca ttatttcctg    4440
tgatgtttcc tgtgtgggcc agttaagaac acttaatttt taaatgaaag gattgggtac    4500
ctttatattc atgaggaatg attccaagtt catgccttca cagctatggt taccaccacc    4560
taagtgacct cacctttgtt cactgacaag aggcacaaac tggaaaggac aaagtctgtt    4620
ggtccttggt tttttgtgcc ctctgattga cctctgactg cacagaggcc ctcggactct    4680
ggttctcctt tcccactcct accccatggc cagatatggc acttggtgct ggagatacag    4740
gataacagaa aagattatca tctgaaagga gttgtagagt ttattatgga tgacagtcac    4800
agcaatatac aaatacagtg caatgtgctc ttttctataa tagatggaga acgtgcacaa    4860
actgtaggag ttaggagtgt gccaaaaact gcctagagag gtgactggtg ggttcacttt    4920
cacagaagta tgggttttgct atggagacat tctagaccaa gggtgctgta tattcaaatt    4980
caaagaagtg tgtacctcca ggcatgttag aaatgagaga aagcaagtga gactgcagtg    5040
taacacacca tgtttacaga gccacatgaa gtggaaagcc cttctcccta cttggcacca    5100
gaaagtggag ggcaagatcg ctcaccaggc aggtcctagg tccagctctg ggtggggcta    5160
tgcccaccat gttcacacga cagaattgat gggatgtggg tttgaaatga gggagaagag    5220
gcaggttttt gcctcctcaa cctagatttt cacttagagc agaaggaagg gtggagcttc    5280
ttgtgaggtt acagccattg ttttcagctt agcttctgtt ccaggaagta ctgcattgat    5340
tcagttatag tggtttgttc tgcgtcccta gattagtcag cctagggcac ttcttgtacc    5400
gagcaagcat ccactgtgtg tagatcaccc tgggccctag agactgggca cctgtcctca    5460
ggaagctcct aggacccatc tgccactgca ggtgcagggc actgaagcaa agtaacccag    5520
agaaaacaga cagctatgca gagcaggact ccagcatggc tgctggggca gaggagggaa    5580
ggattgagct ggaggttggg tggtcagttt gagaaggctg tctggaggta ggttttggga    5640
aagagaaaga catgcatttg caaagccagt ggatgaccac tcagagtaaa ggccaggaat    5700
ctctatgctg agagttagag gtgagtgctc tctcttcatt atccatttca taagcacaca    5760
gcagaatttc tacccaagca atagcatcaa tatgtcatag ctctgaccaa gaattattgt    5820
aaaagaaaat atgacacaag catacatttt tataatcatt taaaatgaga gtgctatatt    5880
```

```
ccaagaatta gaatattggt acttcaagcg aagttagaga ttatttagat tcaaataaag    5940
tatcttaact cacaatgaga gccaataaat aggagctgtc gcaactgtcc aatctgctta    6000
cttttcaggt aaaatgactt gtccaaaaat cataaaatta cttaatagtt attcagaatg    6060
tcttctgatt ctctatggca tgctcttcct tctacattat actatagtcc cttttctaag    6120
agattttta ttaagtaagc atcattagac tgtattcttc atttacataa attcctagtg    6180
cattttaaca taagcaaaca taaaaatacc acttaattgt aaatgtaatt gatcttaagc    6240
tactatgcta gcaaactaaa tacttaacat atattttatt ttccaaacct ttttgtttgg    6300
cctttttctat ttcaggagaa ctagattgag gaatagggt aagaaatgat tttaatgcct    6360
catatctttt aaaacttgtt aaagttact tgttaaagta aatttgaact tatggcttac    6420
cttatatcag gagcaaataa aggcattcaa gaattattcc atagtttagt cttcttaaaa    6480
taactattgt agaatctcag tatttataac atagaagaca aattgtaatg attttgagat    6540
gagaatccct tagatcattt atttatttcc catctctta aaaaaatgac aaaattcaga    6600
ctgataaaaa ggttgaaaaa atattatgaa aaatttctaa atccttttca cccagatttc    6660
caaaatatta acattttact tcatttgttt attctctggc tctctcattt gacagtaatt    6720
agtaatttga ttgatgccct ttcccctaag aatgttagtg tatatttcta caaacaaatg    6780
cattctctta tataactact ttacaatgat caaaaccagg aaattaacac ttatgcaata    6840
taattaacaa tctatgtact ttattcagat tccaccaatt acctctttaa tattcttat     6900
agcaaaagga aatttctagt cacgcattgc cttcaactgt cactttgtc tcctttagtc    6960
tggaacactt cctgaatttt tcttgccatt gatattcttg aagagtaagg tcagttcttt    7020
tttagaatgt ttctccattt gggtttatct gatgtttcct catgattaga ttcaggttat    7080
ttaaatttt dataggaata ccaacaaagt ggcttttctt atcccacaaa gagtcttgct     7140
taatctgagc atagccagcc tgcagacacc atggacaggc ctctagccga gggaccccgt    7200
atgtaaagtt ctgcatattt ctacctagga ggacggagaa cctctggtct cttgactctg    7260
taacagtgct aactgtttta ggtaactgtt cctgatttac gaagtaagct tattagaaga    7320
gtccctgtcc cacctcagct gttattagta tcttgctaag ctcccacatg ggaggaagtg    7380
agcttccaag atcatctgga tttgtctttc ttcactttt ctctcctctt tcttcttcc     7440
ttatttctct cttcttctat aaatcgccaa atcctctccc ctaacagcga cctagaagaa    7500
acaaaatttt tatcagatta caattttagg aaggaataag ataacagata ttccttgatt    7560
agttgatgga gagatgagtg gacacgaata catgagagtt gatgctttgg cttcgtttta    7620
ttttactcct acttcttcct ctacaactgc ttattactct tcaaaggac gtacagcgat     7680
aactttgatt gcacctcagc cactgctcac aggagttcaa acgagctgat gaaaaatgga    7740
aggtcttctc ctggatgctc aacacattgc accaaatgag ttgggaagta ataggcacaa    7800
aaccagagcc tgggacgtg gaaagagcat gggctttgga ggctgaaaga acttggcctt    7860
caccctgcct ttgatgattc ttagctgggt gaccttgtgc cagtcctcgg cttctctatt    7920
tgcagaatgg ggctaatgac acctaagttg tcaggccgat ttgaggatta taaataagac    7980
atttatgagg aacttagtta ttttgtggga ttcagtgaac tatctattat gtatctcagt    8040
ttgtttgagc aaggcctaca tttgggagcc ctcactgggg cagattttcg ctcctattta    8100
gaaaactttt tcttaatca cagcctcaat tgtctttgct aaggaacaaa gactgccaca    8160
ggctctgtgt aggaagggat agggagccgt aattaccttg cgaatgctct tgtatgtaaa    8220
ttgacaatct gtatatagag aaatgtatat ggagaagtgt ctggaaagac gtttgccaaa    8280
```

```
atgctaatga tggttatctc tgggaggtgg gatttcagaa gattttatgc tttcttcttt    8340
atacttttct ttatttttta aatgtagaat ttttttttaa agaaagcatg cttacatttg    8400
ctttctattg ctggattttt caacttttc taataggttt gaatggagta agaaatgtgt     8460
tctaataata tatattctca atcttagctt acaaaggtgt ttctctacca aacacttcca    8520
ttcactgaaa gaaaacaatt tatgcatctt aaagaaactg tgcttacatt tgccttttat    8580
tgctgggatt ttccaacatg tcttaacaga gttcagtgga gaaagaaatg tgttctaata    8640
acgtattctc aatcttagca tacaaggtg tttttctatt aaacgctttt cttcactgaa     8700
aggaagtctt acagaaactg tacttgcatt tatttattta tcttttatta ctgaaattta    8760
acattttcaa tttgttctaa taggtacaaa tggaaaaaaa acatgtgctt ttctttattg    8820
tttgatttgt ttttgttttt ttatttttt tacaaatggc acacgaaacc tcttttaaa     8880 acgtatgaaa caagcaaggg attattcttg ccccgtgtat gttttattcc taaaaatctg    8940
ttagaagcta agggtaccc ttaggaatgg actggtaggg aaggtctgaa cttgatcttt    9000
cagtgagttt tcactgaata aggcagatac acagggactg agccatcctg gaaatagtat    9060
ctcatttagc cctcagaaca acctctgagg taagtattaa taccctatt tcaaagatat     9120 agtgaaagac aggttaagca agttgcccaa ggtcacactt ctgataagta gcactaacag    9180
aattcaaaac tagacctgtc tgattccaaa gctagtgttt atcaaactgt gttccacaga    9240
atactatgtt atttgacctg ttaataagtg atctgcaaca taaaactagg tttgtagtta    9300
tataaacata ttttttgtctt agagactcac agtgcacatt agcatataac aggtttttct    9360
cttacactgt tttttttttct ttatcttggc ttttgtttga ggagcactta ctaatatctc   9420
ataagcgtaa tggtctatgt agcaccaaag ctgtcttatg tggctccagc ctagcttgta    9480
atattggatc agataaggct gaagatgaag aactgataga ggttctttt tttttaactt     9540 aaaaaaattt taaatagag acagggtctc tctatgttgt tcaggctggt cttaaactcc     9600
taggctcaag ggcttctccc acctcagctt cccaaatggc tgggattaca ggtgtgagcc    9660
accatggcga gcctgatcga ggttcttgaa gcctctatcc aaccttaacc acttctaagc    9720
ttgattaaat tcaagagtag attacatggt gctgttagta caggtcaaaa aaagacagg    9780 gatggaatta gaaatccaca ggttctacca gctcaagccc attggaggaa actaagagc    9840 aaagttgatc cctaacctct atgttgagtt gtggaaggta gccacagtta agtgcagttt    9900
ggtcacgcag gtttcctgga aactgatatt ggtggctttt tgcatagaac catgagtcat    9960
gcatctaaga gtcatagact ttgactgtgg gaggggtgtc agttcctcta gatggtagtt   10020
ggaaggggtg ggaggcttaa tcactgccca gtaacagtga aaaggggaag gggaaacgga   10080
gcagcattct ctctgggggcc cttatggcat gtggcaaaag tagtgacaat cttccaccagg  10140 tgagaagatt ttcttactca atttagtatg agtctggaga ggtagaaagt gggagaggaa   10200
ggaagaagag gttcttcttc ctgtctgtga aggaaagaat cagtaggaat gtccctaagt   10260
ttgtgggcac ctagccagct ggtgttctgt ggacaatcag gttacacggg cctgaactaa   10320
ttgtcacagg ataccaggat gttggggctg atgtgactct aggaggcatc tggctcaatt   10380
cctttctgtt actgatgggt gagttagtta ttttcctatg tccaaaacat cagtttatta   10440
gcagactgaa aattcaagcc caaggctcct gtctctgcag tgtcatgttc attccactac   10500
atcagataat tctgaggtaa tgaggctttg agaattcaaa gatgaatagc atagatccta   10560
ccctcaagga gctcacattc tagtgaggga atagtcactt ataaaacaaa atggttagta   10620
```

```
caatggcaga ggtacacagg tattacagat actccttagg gcaagtgagg gttgggtgtg    10680
aagacttaga cacaaacaga gaggacttcc tggaaaagtg acacatcatt aggatgatga    10740
gtaactaacc agaataagag gccagaaaga aaagagaaaa tttcagcaaa gaaacacatt    10800
accaaagtaa ggaaggaagc attaagacaa ggattcaata ttgctttgct aaattttaaa    10860
gtataataca gggggtgttg ccatgagtgt ggagtgatgg acaggagcaa attaggaggg    10920
gcctttgacg taagtgtaca tgcataaatc catcaccaca gtcaaaacac tgagcgtatg    10980
catcactcac cacagattgt tgtggccttc tgtaatccct ttctctcacc cttccctgct    11040
ccctctctac tcacctcctg ccctccccca ccttcatcct cagacagtca ttgatctgct    11100
ttctgttgct atagattagt tttcattttc taaaatgtta tataactgga atcatacaga    11160
atgtactctt ttttatttaa cctctttcac tcaccatgat tattttttaca ttcacctgtg    11220 ctgtagaggg taacaacagt tcattctttt taattgctaa gtagtttcca ttgtaaaatt    11280
ataccactat ttatttatac attcacttgt ttatggacat ttgggttgct tccagtttgg    11340
gctattacaa ataatactac aaaactatga accttcctgt actagtccta gtatggacat    11400
atgctttcat ttctcttggg taaataccta ggagtagaat ggctggatca tatgataagt    11460
atatgtttaa ctttgtacaa aacgagcaaa ctgcttttga acatggttat accatttac     11520 attcccacca acagtgtata agagttccag tttcactaca tcctcaccaa cacttggtgt    11580
ggtcaggttt tgaaaacatt ttagccattc taggagatgt ggagtggtat cttaccatgg    11640
ttttaatttg catttcctta atgagtaatg aagtagagaa ttttttttcat gtccttattt    11700 gccatccata tagtatcttc tttggtgaat tgtctgttct gatcttttgc ccatttaaa     11760 aattggattg tttattttct taccattgag cttcaagagt tgttttttata ctctggatac    11820 atgccttta  tctcctgtgt gatttggaaa tattttgtcc cttctgtgcc ttgtcttttc    11880
attctcttaa cagtgtcttt tgaagagcag aagtttttaa ttttgaagaa gtccaattta    11940
tcaacttatt gtgcttttgg tgtcttatct gagaactctt tgcataacca aggttgcaaa    12000
tatttccttc tggagaatta tagtttttgga ttttacctttt agatctatga ttcatcacta    12060
gttacgattt cgtatggaga gaggtataaa tgcaagttca tttttgcata ttaatagaca    12120
attgttccag caccatttgt tgaaaaaagt attcttcatt ctgtaatata ttaattttgt    12180
attttttttg aaaatcagtt gtccatatgc atatggactc tattctgttc tcttgatata    12240
tttatttaac accagtgcta tcctgtcttt attgttgtag ttttatagaa agcaatataa    12300
ttaggtagtg tttgtactcc aattttgttc tttatcaaac tcattttttac tattctaagt    12360 cttttgcatt cccaaatgaa ttttagaatt aatttcttga agcctacaaa aaattctgct    12420
gtaatattga tggggattac aatctataga taaatttgga agaattgaca tcttaaaaat    12480
attgaattcc tggtagatgg acgtggtata tctctccatt atttgcatct tttcaatttc    12540
tttcagcaat gtttgttttt aagttttcag tgtacaattc tttcacaact tttgtcagat    12600
ttatgcctaa gtatttcata tatgatgcta ttgtaaatga tacttttaaa aatacttgat    12660
ttctaatggt tactagtgca tagaatgcta ttattttttg tggattgaat cttgtttcta    12720
gcaaccttgc tacacttact tgttagttct agtagtattt ttgtagattt atttagattt    12780
tctacaaaga cattcatgat atctgtgaac aaagccagtt ttactttttt ttctttccag    12840
tttggatgcc attcttttca tatttcattt gcactgccta gaaactccag tacaatgcca    12900
aatagagtag ttaagagtaa acagacttat tttcctcctt atataagggt aaggcatttg    12960
gtgttatacc attaagtatg atgttcttaa ttctatgccc ttcataaatg cctttttataa   13020
```

```
gtttgcataa gcgttcttct attcctagtt tgctaagagt tttcatcaaa aatagatgtt    13080
gaattttgtc aaataaattt cctgtatcta ttgagatgat aatttatttt ctctttcaat    13140
tcattaatat gattaattaa gtagtttttt caatgttaaa ataaccttgc attcctgaga    13200
gtagccccat ttgttcataa tttcttatca ttgttctata tcgttagatg ctttttacta    13260
aaatcttgtt tataattttc acatcttgtt ctgaggaaca ttggcccgtg gttttatttc    13320
ttgtaatatc tttctgcttt tagtatctga aaagtctggc ctcacaggat aaggtagaga    13380
gtgtaccctc cttttctatt ttctggaaga cttgatatag aatcagtatt atttctgcct    13440
tacatgttta gtagaaatca tcaataagac atctggacta gcagttttct ttatgggaag    13500
acttttaaac tccaaattca gtttcttatt agagatagga ttattcaggt tatctatttt    13560
ttgagtgaga tttggtaatt tgtgcctttc agtgaattca tctatttcat ctaagttgta    13620
ttggcatgaa gtcatttatt atattgactt atatttttga tatctataga atttgtagtg    13680
ttgttctctc aatcctaata ttgataatct ttgttctcta ttttaaaatt gattacctgt    13740
gtataagttt atcaatttta tcagtcttct aaaagagcca acttttgtgg ggttttttaaa   13800 attgttcttc tgtttaattg atttcagtgc ttatcttcat tatctacttc cttctgctta    13860
ttttgggttt agtttgttat acttttttcta gtttctcaag atgcaatctg aagtcattaa    13920
tttgagacca ctttcctttc agctatagac atttagcact aaaattcacc ccaaatatt     13980 gctttagtga cattcccaca ttttcaacat gttttttaaag tttttctcaa ttcagaattc    14040
taattttctc tttgatttct tctttcatct atgaactatt tagaaatatg ctatttagtt    14100
tcccaatttg aggaaacttt ctagggatat ttctgttatt gatttctaat tcaattcctt    14160
ctaaatttgt tgaaacttga tttatggtcc agaatggtct atcttggtaa atgtttcatg    14220
taaccttgaa aagaatgtat gttctgctgt tgtggggtgg agtgttctat cacaatcagt    14280
tagtttaagt tgactgatgc tgttgttcaa atatttactg cttttctgtc tactgattcc    14340
atcaactatt gagagaagga tattgaacta ttcaagtata acttatactt gtctatatct    14400
tctttcagtt ctgttcattt ctgtctcata aatttttgact aggtgcaaaa acacttagga    14460
tttttatgtt ttttagctca atcagtccct ttataattat aaagtaatct tctttatcct    14520
tgataatttt ttctgtaata gtgtttgttt tagtctaata tagacactcc agcctttttt    14580 tccctttat tagtgttagt atggtatatc ttttttccatc cttttacttt aaaatgtatt    14640
cgcttcttta tattttaaat gcattttttg taaacaacat aattgggtct tgttttttca    14700
atccatctat ttattcctgc ttcatatttt aagtattcag accatttcat ttactgtgat    14760
attggtatgg ttgggatttt agcatatttg tttttttattt gtctcatttt tctacttgtt    14820
cttatttttt tcccatttgt tgttcccct tttctctttt tctggcttct tttgattaat     14880
cgagtatttt ttaagatttt taccttcaag tgagatttcc actttacata taagaagctc    14940
acagtagtat acttccattt ctcccttccc agtctctaca ctattattat cataaagttt    15000
acttttacat ttattattaa tgcaatgcaa tactgttact atttttgttt gaacagttca    15060
gtatctatta aagagatttg ggcaggcgcg gtggctcatg cctgtaatcc cagcactttg    15120
ggaggccgag gcgggcggat cacaaggtca ggagatcgag accacgggga aacccgtct    15180 ctattaaaaa tacaaaaaat tagctggacg tggtggtagg cgcctgtagt cctagccact    15240
cgggaggctg aggcaggaga atggcgtgaa ccggggaggc ggagcttgca gtgagccgag    15300
atcgcgccac tgcactccag cctgggcgac agagcgagac tctgtctcaa aaacaaaaa    15360
```

```
acaaacaaca acaacaaaaa aagagattta agacgaggtg cggtggctca agcctgtaat    15420
cccaacactt taggaggctg agacaggcag atcacctgag gtcaggagtt cgagaccagc    15480
ctggccaaca tggcgaaacc ccctctctac taaaaacaca aaaaattagc tgggcgtggt    15540
ggtgcatgcc tgtaatccca gctactcagg aggctgaggc atgagaattt cttgaacctg    15600
agaggcggag gttgcagtga gccgagatca caccactgca ctccagcctg ggtcacagag    15660
caagactttg tctcaaaaaa ataaaaataa aataaaatta aagagattta ataacaaga    15720 aaaaagtat tgcgcattta ttcctgtagt caccatttct ggtgctcttt gttcctttgt    15780
gtaaatctgt agttccatct ggtctcattt ttcttctact tagaggattg cttttaacat    15840
ttcttgtagt atggatctac tgatgaggaa ttctttcacc ttttgtgtat cttaaagtcc    15900
tttttttaag ttattaaaat gtattttat tgggtataga tttttagtat gacaattttt    15960
tttctttagt attttaaatg tgttgctcca ctttcttcca gcttgcctgt tttccaataa    16020
gaagtctgct cttatcctta caattgttcc ttagtccata acatgtcttt ttttcccctg    16080
gttgttttaa gattttcttt ttatcactgt tccttgagta ctttgattat aaagaccta    16140 gtgtagcttt cttcatgttt cttgtgcttg gagttcattg agctattgag cttcttggtt    16200
ccatagggat attatttca tcaaatttag gattttattt agtcattatt tcttcaaatt    16260
atttttctat ctctcttctc tcctcaattt tagagactcc agtgacatgt atattaagcc    16320
acctgaaatt atttctcaac tcatgatgct ctgttcattt aaaacatttt attttctggc    16380
caggcatggt ggctcacacc tgtaatccca gcactttggg aggccgaggt gggtgggtca    16440
cttgaggtca ggcatgcgag accagcctgg ccaacatggt gaaaccctgt ctctactaaa    16500
aatacagaaa ttagttgggc atggtggcac gcgctgtggt cccagctact cgggaggctg    16560
atgcagaatt gcttgaatcc aggaggtgga ggctgccgtg agccaagatc acgccactgc    16620
actctagcct aggcaacaga gcgagactct gtctccaaga tatatatata tatatatatt    16680 tttttttt ctatctgtgt ttctttgagg atattttctc ttgccgtctt caagttcact    16740 agttttttc ttcagcaata tctaacctgc cattaatcca atccaatgta tttttcatgt    16800
cacacattgt agtttcatct ttagaagttt gatttgagtc tttttatatt ttccatgtct    16860
ctatttatgt ttatttatt ttatttat ttgagacgga gtctcgctct gtcacccagg    16920
ctgtagtgca gtggcgcgat ctcggctcac tccaagctcc gtctcccggg ttcacgccat    16980
tctcctgcct cagcctcccg agtagctggg actacaggcg cccaccacct cgcctggcta    17040 atttttcta tttttagta gagacgggg ttcaccgtgt tagccaggat ggtctcgatc    17100
tcctgacctt gtgatccgcc cgcctcggcc tcccaaagtg ctgggattac aggcgtgagc    17160
caccgcgccc agcctatttt tttgaaaaca tagtatctgg cttaatggct ttactaatct    17220
aacacctggg ttggttttca tctatcgcca tattataggt tgtactttct tgcttcttgc    17280
atgcctgata ttttgagtga atctatgtgt aaattttact ttgttggtg ctaaatattt    17340 ggcattccta taaatcttat tgagcttgt tttaggatgc acttaagtta cttggaaagt    17400
gtttaatatt ttgggcccctt actcttaaga tttgttgggt agaacagtgt tcagtctaga    17460
gctatctgtt ccctattact gaggccacat ccttctgtgt actctagcct gtgaatcttg    17520
gagttttcca gtctgactgg tgggaatagt cactggtgct gtgtgaatgc caggcactgc    17580
tcagatggta cctatccttg ggcagttttg tacatgcagg tgctaatcag gactcagcta    17640
aattcttaat ggacactttg gtagactgaa taataggccc caaatatgtc catgcacctt    17700
atagggcaaa gatgactttg aagttgtgat taaatcaaac atctcgaaat ggggtgatta    17760
```

```
tcctggatta gccaggtggt tcttatctaa tcatatgggc ccttataaga atgaagcagg   17820
agataagagt ggaaagtagc agatgtgatg acaaaagcaa gaagttgcac gatgcaagaa   17880
aggaggtaag gaatgcaggt gactttagaa gctgacaaac acaaggaaac aaattctctc   17940
cctgagccct taagaagaaa tgtagcctag ccaacaacct gaatgtatac ttctgaccct   18000
cagaactgta aaataataaa tttgcgttgc taaggcacga agtttgtggt aatgttttag   18060
cagcaatagg aaactgatgc aagcacccgc tgcgaatctc tggggtttgc tctctgtgca   18120
cctttctttt gtacattgcg gtgtcctgta aaccctagct gccttggtct cctcaaaatc   18180
tcagctctgc caggctctcc ctctatgctc catggtttgg aaactgtctg tgaatataag   18240
ctgaggcaat cacagggctc acaccattta tttcccatct ctcatgggtc cgtgcccttc   18300
attgtctcac attcagtgtt ttgcagacca ttattttata atctacattt tttagctgtt   18360
tcaggtgagg gggtaaatct ggtccctgtt aatccattgg ccagaggcac atttcccaaa   18420
tatatgattt tatattttta cgttaagaaa aggaaaatga aaaggtgaaa tgaattttta   18480
ataacatttt agttatctca atatgtacaa aatactataa tttaaaaatg taatccatat   18540
tgaaaaatta ctgatataat ccttttttgta ctaagtgtat attttacact tatagcacat   18600
agtaattcag actagccaga ttctaagtgc tcaaagctgt agcacagctc tagggtacag   18660
tgaatcatga gagtctgtgt ttagctgctc aaggggacta cattcatttg aatgtttcag   18720
cttttatgtc ctccaccatg aaatattctt tgatcaaccc agctgcaaat ctttgcatct   18780
tcatggcctt tgttactgtt ctttgggact tgacatattt tatctttat tgattgatgt   18840 agcttgtgca aagggcaaca ggaaggattc tcaagaattt ggaaatgagg actggcaaat   18900
gtcacattct aagagttaat ttaatttttt aaaattctag ataaaatgaa taagattatt   18960
tattcataga tgtgtcttac tctatgagat attttgtcag tgtgatactg ataaagggct   19020
gggaaacact caaattcatc attcactcct gataaacaga gtagttcttt aagactcaat   19080
aattggccgg gtgtggtggc tcaagcctgt aatcccaaca ctttgggagg ctgagacggg   19140
tagatcacca ggtcaggagt tcgagatcag cctggccaac atggtgaaac cccgtctcta   19200
ctaaaaaaaa atacaaaaat tagccgggcg tggtgacggg cgcctgtaac ccagctactc   19260
gggaggctga ggcaggagaa tggcttgaat ctggaaggtg gaggttgcag tgagctgaga   19320
tcatgccact gcatgccagc ctcggcgaaa gagcaaaact ccgtcaaata aataaataaa   19380
taaataaata aataaataaa taaagactaa ataatcatgg gttcaattta ttgagtaccg   19440
gtcttgctgt atgccagtct gtgtgataag atcatttaat attcacaacc accctataag   19500
ggataagtgt tggcccgttt tacataggaa gaaattgtga ctggaactgt taagttggtg   19560
tgcaattctc acacagctgt ttagaggcat atgtaagagg aaaattcaag tttgaccccca  19620 aagcctgggt agtaaatcat tacactttac ttctgatata tattcaaatg catttataat   19680
ctaatttatt ttattttatt aaagtaatca tgtagattta agaataatcc tgaggagtaa   19740
gacaagaaga aaagagggga aaagagcaca aagtaaagga aaaggatatg agatagatac   19800 aagtattgg tgtttacaac agagaaattc actttattgt ggaagagaag tagctcatca   19860
ggcttatcta cagcctggat gaactattcc ctcaagacca tgtgattccc aggtaccttg   19920
aaactgcaaa ggagatacta tggattgcac aagtgaccca tgcactggaa aaggcataat   19980
tttcatggaa aaaatcact gccccaacat tctgcttgat atatcagtcc tgtgcagggt   20040
tttaaaaatg agtcacttta tagaatatca ttacctctga cagaaaattc aaaattctgg   20100
```

```
ccaggtgcgg tagctcatgc ctgtaatccc agcactttgg gaggccgagg caggcggatc   20160
acctgaggtc agaagtttga ggccagacta ggcaacatgg tgaaacttcg tttctactaa   20220
aaatacaaaa attatccggg catgatggtg catgccttta gtctcagcta cctgggaggc   20280
tgaggtggga ggatcacttg agcctgggag gtgaaggttg cagtgaattg agattgtgcc   20340
actgcactcc agcctgggtg acagattgag accctgaaag aagaaagaaa gaaagagaga   20400
aagagaaaga gaaggaaag gaaagcgaaa aggaaaagtc aaaattctgt atctggattt   20460
ctagaattga gaaccagaca ttggacattg atgtcctcac taagaaaatg atattctagt   20520
tgaaaaaaat aaagcttaca ttgctatctc tttttacttc cccattgcat atttgttggc   20580
ttgttttatc tttgctgtaa gactgttgtc ttctggagga tagctactgc ttagtcatgg   20640
ttgcatcttc cacaacatct agaacagaaa acataaatgt ttctgcaata aagaataaa    20700 tgaggcgtgg atatgttccc cctactttca tgtggagaag tttactgatc aaatgtagca   20760
tgtacataaa tcacagagta tttaagaaac tggctgatca agctgttggc tttcttgatg   20820
gctgattgac cagtccatcc ctgacttcaa gggcttaagt gcccaggcac tagttgctaa   20880
tgctgcagtt agagctaaag cactggcctg gtctctgtca ctgtgactca tcctcttcta   20940
agaatggctc tattttcttc tacaatactt aattcaatgt taagcattgt tggcttgccg   21000
aattgggcaa aaactgaatg tctaagatga gccagttggt atttcagttt agaactagga   21060
aagcgcagag tttgggaaa cttccagag gagagccaca gctcaaaccc aaggtaatgc    21120
tagagatccc tgaacatttg tgcactctga tctctggcta ccttacagag tgaggtaact   21180
tactttcttc ttccttattc cttagggcaa gaatatcacg gcatgggcat gagtagcttg   21240
aaactgctga agtatgtcct gttttcttc aacttgctct tttgggtaag tgtatctctt    21300
ctgagcacgg tttagctcac ctttacccag ctaagctctc ctcattcctc tactgaagag   21360
gctggggtaa aatgcatgcg tgtttgggtc atgtccagca caaccatcct agaaacaaaa   21420
gagtaataat ttttccctc ttcctgccac agaataaacc tgcaaaattg aaaggtacca   21480
gtgcagttat taatggaggt gctgtttctc tctgagggct ttagtttact actactcata   21540
gctaacatat ataggtgaga aacctgagac tgtgctctgg atattgagtg cctctgtttt   21600
tcttgtcttt ttttctagat tccttgaaac aataagtgat tgaaaggaaa gtcaccctt    21660 ccagggaggt ttcactgtat aaaattcagc aattgaattt cagatatagg atgggttggt   21720
acttgtgtat atgagaagat tattataagt ttggcttctc tagttttctg cctagcaaga   21780
tgagcttcct caagcagggc atcttctcta catggtcatg gtttctacag agaaagccat   21840
gtgtgagcga ctgaaaagat aaggaaaaag aagttagacc tatatatggt gaagatactg   21900
tgtggctcac agaagtgatc tttccttggt atctggagat gggtaggaag agttgtgagt   21960
aggtctccac atgagaaagc tgagattgcc tctccaatgt aagcatggaa aagtttggta   22020
aagaaattgt tcatgagact cttgattgag ccagttaaaa ataaagtgat tctgatctca   22080
aggaagtgag aatatgagga gatacccaag aaccacattt tgcttcagga tgttgtggga   22140
ttcttccttt cagatctgtg gctgctgcat tttgggcttt gggatctacc tgctgatcca   22200
caacaacttc ggagtgctct tccataacct cccctccctc acgctgggca atgtgtttgt   22260
catcgtgggc tctattatca tggtagttgc cttcctgggc tgcatgggct ctatcaagga   22320
aaacaagtgt ctgcttatgt cggtgagtcc ttacagcaga tgtggtgccc caagtcgggg   22380
agatggtgcc taaatcccag gcaagatgtt tcttggtaga tcacttatag gcacagaaag   22440
atcataggaa aatgagattg gtacctcaga tcagccaagt ctgcccagac caatagtata   22500
```

```
ttatgtatga ctagggtccc atggacaggt gaaagagggc attgctatcc cccttgtagc   22560
catttttata ttgctaataa tgacttttgt cattattgta attccccttt atagcatttt   22620
attttttctt tatgtctgga tgaaatcagg tgtcatccat cttccaaaat cctcctcatg   22680
ctagctatta ttatgtactt tcagattctg actgagagtc gctaactaat ggaaaataat   22740
ttctaggctc tttcctcccc aaatgccaaa ggatgcttcc ttaactcatg tctgcacaag   22800
atactccgta gagagatcca acttaggtga gggctctggc tgcagccatt gaggtctaat   22860
gtgagagatg ctacagcctt ttgcatgttc cctatcaggt actatcctga ggagtacctt   22920
aaggcttagg ttttgcctgt aagcacagtg cctgtagagc actgagctct acatttctgt   22980
agtgttccca gaacagagct tgttgtaaca gtgccactct accaataggc gtgggtttct   23040
aatcacattg gttcttcctt aaatcatttg gttaatcttt tttccattat ggttcaacat   23100
tttggtggtg gttttttgtt ttgttttttt cttcttgttg ttgttttgga gatggagttt   23160
cactcttgtt gcccaggctg gagtgcaatg gcatgatctc agctcaccac agcctccgcc   23220
tcccgggttc aagccattct cctgcctcag cctcccgagt agctgggatt acagtcatgc   23280
gccaccatgt ccggctaatt ctgaattttt agtagagaca gggtttctcc atattggtca   23340
agctggtctc taactcccga ctttaggtga tccacctgcc tcggcctccc aaagtgttgg   23400
gattataggc gtaagccact gcgcccagtc tgtatgggtc aactcttaaa ctggagccaa   23460
gagaaagaat tttttaaaaa gtccctcttc tcagatagtt gtcagactaa tggcaaagga   23520
tggaagatag cagacatggg gtaaggtaaa tgttttaagc agtcaaaatt aatgttgggg   23580 taaaaaggt gaaggagaag gaataagtga aaatgttttc tgttgtgtgt tattagcata   23640
aaaggagtaa gcatcgaaag ctggaaacaa atatgagtta gaaccatggc taggacccttt  23700 cttttctacca ttgtacaggg ctcctctcag ccactaccag cagtcctcca cccagaggta   23760
tccctgatct tgtagaaagg accaggcccc aaatgatcta gtttaccaac cttttgctta   23820
actgcttcaa taggcagatg tcaaaattgc ttaacttatt caacaggtgg tggtgtgtat   23880
gtattatgca tgtagtgctc tgataggcac agcaggtagg agagagcaaa gaagacagtt   23940
gatctgccct ctagagtcta attgtagaaa aagaacacat attttcacaa aacaaaagaa   24000
ggcttacaac ggcctgagga ggcagaacag gaacaccctg tacgtgtgca aatgcccctg   24060
gatgctccca gagctgagtg gggtggac gagaatgggg atcagtgctg tgagaatgta   24120
tctgctttgt cccagttctt catcctgctg ctgattatcc tccttgctga ggtgaccttg   24180
gccatcctgc tctttgtata tgaacagaag gtaagttata aagacaacaa cttattgtct   24240
taatactgaa agtggggagt atgcagtgga gaagttggta caaagttaca gaataagttc   24300
tataatagag atagaaatga agtggaagga tagaggaaac agagagtaat tgtaattggg   24360
gggaaaaatt tgtatgaaag agattgtatc tgagtggtat cttgaggggt gcctggaaag   24420
agcagtaaaa caagtgtctc ttcctctact tgctttcctc tgtgtgtttg gcaggagaga   24480
atgtctgcct cagtgcctaa ggatagccct tgctttaatt gctccttttc ctcccttgta   24540
aagccagagc tctagaagga agcaagccta ctaaatactt cttccttcaa tgccacctca   24600
tgctcagcat gtatgcccat agataaacac cctcccctca cccttagttc tgaggagacc   24660
atttggaagg gaagcgcaag tggaaccact aacctatact ggaaattcct tattccttga   24720
actcacctgc ttttttaccat gtctcctctg ctggaatgtg cctgcccagc tgaatgagta   24780
tgtggctaag ggtctgaccg acagcatcca ccgttaccac tcagacaata gcaccaaggc   24840
```

```
agcgtgggac tccatccagt catttgtgag tacaggtgga atcctcttca gatcagccca    24900
gacttcattt tcaagcctaa atccttgggg gctagttcct ttttctggaa gtttcagaat    24960
ctaaggtcca catccctgaa tcccagaata atgccttggc tatcacaaac atgggagccc    25020
agtaattagt ctgattagta caaagttctc tacattctct ctttcatcct tttctaacat    25080
gaataggttt attttctaag ttctgctagg atgtgaagaa gacccaaaca cagcaaactg    25140
gattagttta tgtattttcc aaaattttac tgaaaacagc attgtataac acaagaaatt    25200
gccattgagt tcccgagttg cccaaatcag gcttgttacc tagcccacca acatcccatt    25260
cctcatgtgc tgtttccacc cacaaacgtg tatatgtaca gcatatacaa gctctgcatt    25320
cctgacatga tgtgttggga gataaagatg gagccttgca ccagtataat ctatttgtgt    25380
ctcgaaacag taccactatg aaagcacgct ggcttagtgt ggagtagaag aaatggcaca    25440
ggaattagag cctggagacc agaattgggt agccctgggg aagtcactta acttatttag    25500
atctccaatt cttattttt ttaattcagt ttagaaaact ttttattaca taattttag    25560 aaatatacaa aagagaaaaa cagaaaaatg aatctcccaa ctcctcaata gttaacattt    25620
tccagtgtca tctcatctaa ttccccacac tttttttgtt agaatatgtt aaagcaaata    25680
ctagacaata tattatttca cccactaaat ataaagaaac ttcttttaa tacacctaaa    25740 attttataat ttcttaatac cactaataaa gtctataatt aaatttccct aattttctca    25800
aaaaatttta attgacttgt tcaaatcaag atcttaacaa ggcctatgtg tttatatttg    25860
aatgataggt ctctctattt atcttttaat ctataatagt acacctcttt gttcttgctc    25920
tttgtggaaa gaaattaggc tatttgtcct ttagacttct ccactctcta gatcaggcta    25980
gttgcttcct cgagtatttt ggtatcaggg agtctctgtc tcccataagc cccatgaact    26040
taaaagtttg atgtggtttt tgttttgtgg taagactgcc atagctgtca cttcctgttg    26100
catcgtgtaa gcaggtacat aatgtctgat ggtcctcctt tctgtgatct taagattggt    26160
tggtgggtcc aggggtggtc agcctaatcc ctccattatg cagtccctgg gtgccttatt    26220
cttgatctgt aaaatgtgac tagattaagc acaggggtct ctactccaca gggatcttat    26280
gtgaatgaaa tggtataaca gattagaaag cactttgttt taaggagccc atagcaatca    26340
gaccaattct ggacttctgc tatagagtca gatctgaagg gcacacctt tcctctaagg    26400 tccacagctt ttttcactg ttgactttct aaccatcatc attttggggg tttggctttt    26460
agctgcagtg ttgtggtata aatggcacga gtgattggac cagtggccca ccagcatctt    26520 gccctcaga tcgaaaagtg gaggtaattt tgtcggcaat gtttctgtta ttgacctctt    26580
tgtttaaatg tttaattacc tcggaaactg cagtcataga ggacctagac cttctattga    26640
gaaacagggg accttgaata aaagagaggc cagggcaaca accttgggta attagaaaag    26700
tcagaaaaac atacgaacaa actcatttag actagagaca ctgtgattga tcttgctaca    26760
ctagactatt acattagagg ggaacagtta cttttgtgtg aaagtaggag agggttgtgt    26820
ctagatattt cttaagcaag aagtaggtct ccttatggtt aaagtgaaat gtataggtt    26880 gagatagaaa agtttctccc tctccctctt tctctgctct tcttccttgg agatggcaga    26940
atccagcccc ttagggaaat gaatcatagg tgaaggagta aggagttgag ggagacagag    27000
ttagtggaac tactgaaaca acctgtccaa ttaatttgga cctccagaat aggctctgag    27060
aagaagccac aactatcttc caactagact gaatccctga ggtcttgtct cctcatgtta    27120
tctgctcctg aaggggtttg gaaatctcca gggttttca ggtttgtgga gaaagactag    27180
gacaaccact gaccagcaac tgccctggca cttggtaggg ctatgatgga tttactgaat    27240
```

```
gttgaagcag aaagtgaaat gcaaaccaat tttagtattg catgccctat gttaatctct   27300
ggtcagcact gagtgttcaa agacagtagg acgtcggttg ctgacctgcc tcttagaagc   27360
tagtttaact cagcgggtaa ggatctagga cttctacatt agttaccact gtaatgataa   27420
caccaccaga aaagtctgta gtttaatatt tcccaccttn tgcctgtttc ttcattcacg   27480
caaagaaaat aaaaatataa tacctaagcc tctttgtatt acataaagca aaatgcaaag   27540
cactgtatct tccaaatact tcctcttgat atggtggaat tatagagtag tatcatttgt   27600
aactgaaatg tcttctaggg ttgctatgcg aaagcaagac tgtggtttca ttccaatttc   27660
ctgtatatcg gaatcatcac catctgtgta tgtgtgattg aggtaagagc ttaaccacag   27720
ggttattgtg aggattacat gagttaagtc aggtaagatt tcagaataat accaggtaca   27780
cagtatttac acaataaatg ttagctattt ttactaatat atgaattccc ccagccaagt   27840
agcaaataat gtaattaaca atttgcttta aggtatatag aaaatgtgct ataagaacat   27900
ctcttggccg ggcgtggtgg ctcacgcctg taatcccagc actttgggag gctgaggcag   27960
gcagatcacg aggtcaggag atcaagacca tcctggctaa catggtgaaa ccccgtctct   28020
actaaaaata caaaaaatta accagacgta gtggcaggtg tctgtagtcc cagctacttg   28080
ggaggctaag gtaggagaat ggcgtgaacc tgggaggcgg agcttgtagt gagtcaagat   28140
cgtgccactg cactcctgcc tgggcgacag agcgagactc tgtctccaga aaaaaaaaaa   28200
aaaaaagaa catctctctg gtcaattcat tcctcagaga tatgagtgat tcacatgatt   28260
cacagtcaaa caaaaaagcc accaagcaga atcccactgt gatccctcct cagctggtct   28320
gaaaaatacg aattgataaa gtatttcatt tgaaaacctg atcttgcatg ttaagggct    28380
gatgacgaaa attgtaatca atttcctctt tgtttctgtg cttagtttga caagtgatgg   28440
gtgaattgag ggtagttttt tgtccttttt aataaaaaag gacaaaaata atgtgatatt   28500
tctaacattt ttctacccaa gtgttgggta tatcatagat tagttaaaac tcaatcagga   28560
agctcagaga aaatgatttt tctctgtttg gaaacaaagg aggcacagag catggataga   28620
gataactcat tgcacagtgt tcagtgagca gaatatgacc atcctagcag cagggcttct   28680
gtgacttcct cagaagataa aacatgctcc agtactttac agcctgttat cttgtcatca   28740
ttgaccccgt ttctctcctc actgctattc tttaaccaaa ggaaagagct cctgagagag   28800
acttgaaagt aatggttgga agggtggttt cagtgtaatg gatacattct ttttctcaga   28860
ggccaatccc aggcattgtg aaagaaatgg cttttcttat gaagacttca aattttccca   28920
actcttttca caggtgttgg ggatgtcctt tgcactgacc ctgaactgcc agattgacaa   28980
aaccagccag accatagggc tatgatctgc agtagttctg tggtgaagag acttgtttca   29040
tctccggaaa tgcaaaacca tttatagcat gaagccctac atgatcactg caggatgatc   29100
ctcctcccat cctttcccct tttaggtccc tgtcttatac aaccagagaa gtgggtgttg   29160
gccaggcaca tccatctca ggcagcaaga caatctttca ctcactgacg gcagcagcca   29220
tgtctctcaa agtggtgaaa ctaatatctg agcatctttt agacaagaga ggcaaagaca   29280
aactggattt aatggcccaa catcaaaggg tgaacccagg atatgaattt ttgcatcttc   29340
ccattgtcga attagtctcc agcctctaaa taatgcccag tcttctcccc aaagtcaagc   29400
aagagactag ttgaagggag ttctggggcc aggctcactg gaccattgtc acaaccctct   29460
gtttctcttt gactaagtgc cctggctaca ggaattacac agttctcttt ctccaaaggg   29520
caagatctca tttcaatttc tttattagag ggccttattg atgtgttcta agtctttcca   29580
```

```
gaaaaaaact atccagtgat ttatatcctg atttcaacca gtcacttagc tgataatcac    29640
agtaagaaga cttctggtat tatctctcta tcagataaga ttttgttaat gtactatttt    29700
actcttcaat aaataaaaca gtttattatc tcaatcacaa cattcctata tatcaaacac    29760
tccttccatg acccagcctg attaccctga ttaatgcacc aaaccaggtg tattaattgt    29820
ctcctgctgc ataaaatatt actccaaaat ttagtggctg aggacaacaa acatttatta    29880
tctcatggtt tttgtgggtc aggaatctag gagcagctta gctgggtgat tctggttcac    29940
agtctctcat gtaactgcaa tcaacatgtc agcctgggct gcagtaacct taaggctcaa    30000
ctgaaagagg atctactttc aggctctctc acatcgctgt tggcaagcct cagatctttg    30060
ccacttgtgc ctttccacgg ggcttcctta tgacatggaa gctggcttcc ccccattaa     30120 agacatccaa gaaagggcat gagattcggc acccaaaaca gaagccacag tttgttgttt    30180
ttgttgttgt tgttttgaga tggagacttg ctttgtcaca taggctggag tgcagtggca    30240
caatctcggc tcactgcaac ctctgcctcc caagttcaag cgattctcct gcttcagcct    30300
cctgactggg accacaggtg tgtgccacca tgcctgacta atttttttgt gtgttttag     30360 tagagatggg gtttcaccat gttggccagg ctggtcttga actcctgacc tctggtgatc    30420
cacctgcttc agcctcccaa agtgctggga ttacaggcat gagccacgcc acagttttta    30480
tttataaccc cagatgtgcc accacatcag ttctgccata cactgtttta aaaaagtgag    30540
ttgaattgtt cagctcacac tcaaaaaaaa aaaaaacaa aaaaaaagg agattataga     30600 caagggtata aatctgtagc acatagagat cactggaggt catctaagag gttgccaacc    30660
ccaccatatt tgtttggtca aaaaagaag ctaaattgaa ttgtctataa gctaaattta     30720
attatctacg tataaccaca ctttgtaa                                        30748

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
ggggccaaga agatgacacg                                                    20

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
ggacgcatgt ggaggtcaga                                                    20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
cgtgtcatct tcttggcccc                                                    20

<210> SEQ ID NO 9
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 9
tcgtgtcatc ttcttggccc                                              20
```

MODULATION OF LNC05 EXPRESSION

STATEMENT OF GOVERNMENT SUPPORT

This invention was made with government support under CA013106, CA220997, and GM042694 awarded by the National Institutes of Health. The government has certain rights in the invention.

SEQUENCE LISTING

The present application is being filed along with a Sequence Listing in electronic format. The Sequence Listing is provided as a file entitled BIOL0307USASEQ_st25.txt, created on May 29, 2019 which is 132 KB in size. The information in the electronic format of the sequence listing is incorporated herein by reference in its entirety.

FIELD

Provided herein are methods, compounds, and compositions useful for reducing expression or activity of long intergenic non-protein coding RNA 862 (hereinafter referred to as lnc05) in an individual. Also, provided herein are methods, compounds, and compositions comprising lnc05-specific inhibitors, which can be useful in reducing lnc05-related diseases or conditions in an individual. Such methods, compounds, and compositions can be useful, for example, to treat, prevent, delay or ameliorate cancer in an individual.

BACKGROUND

Hepatocellular carcinoma (HCC), the most common type of liver malignancy, is one of the most lethal forms of cancer. HCC is usually not diagnosed until late stages and has a poor five-year survival rate of less than 14%. Excluding liver transplantation, the current standard of care for HCC is treatment with sorafenib, a multi-kinase inhibitor that targets Raf, receptor tyrosine kinases, and platelet-derived growth factor receptor, which extends median survival time from 7.9 months to 10.7 months. This modest gain emphasizes the urgent need to identify new and effective therapeutic targets for HCC.

Genome-wide analyses such as the ENCODE (ENCyclopedia Of DNA Elements) project have revealed that most of the genome is transcribed, even though less than 2% of the genome encodes for proteins. Thousands of transcripts greater than 200 nucleotides in length, called long non-coding RNAs (lncRNAs), are expressed in a tissue-specific manner and undergo changes in expression level during cellular differentiation and in cancers. LncRNAs have been implicated in numerous molecular functions including modulating transcriptional patterns, regulating protein activities, serving structural or organizational roles, altering RNA processing events, and serving as precursors to small RNAs.

SUMMARY

Provided herein are compositions, compounds and methods for modulating expression of lnc05-associated with cancer. In certain embodiments, the cancer is hepatocellular carcinoma. In certain embodiments, the cancer is breast cancer. In certain embodiments, these compositions, compounds and methods are for modulating the expression of lnc05. In certain embodiments, the lnc05 modulator is a lnc05-specific inhibitor. In certain embodiments, the lnc05-specific inhibitor decreases expression or activity of lnc05. In certain embodiments, lnc05-specific inhibitors include nucleic acids, proteins and small molecules. In certain embodiments, the lnc05-specific inhibitor is a nucleic acid. In certain embodiments, the lnc05-specific inhibitor comprises a modified oligonucleotide. In certain embodiments, the modified oligonucleotide can be single stranded or double stranded.

Certain embodiments are directed to lnc05-specific inhibitors useful for inhibiting lnc05, which can be useful for treating, ameliorating, or slowing progression of cancer. In certain embodiments, the cancer is hepatocellular carcinoma. In certain embodiments, the cancer is breast cancer. Certain embodiments relate to the novel findings of antisense inhibition of lnc05 resulting in impeding tumor initiation, decreasing tumor progression, cell proliferation, colony formation, metastasis, or a combination thereof. Certain embodiments are directed to lnc05-specific inhibitors useful in reducing tumor cell proliferation, colony formation, and metastasis.

DETAILED DESCRIPTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Compounds described by ISIS number (ISIS No.) indicate a combination of nucleobase sequence, chemical modification, and motif.

Unless otherwise indicated, the following terms have the following meanings:

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-O-methoxyethyl" (also 2'-MOE and 2'-O($CH_2$)$_2$—$OCH_3$) refers to an O-methoxy-ethyl modification at the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"3' target site" refers to the nucleotide of a target nucleic acid which is complementary to the 3'-most nucleotide of a particular compound.

"5' target site" refers to the nucleotide of a target nucleic acid which is complementary to the 5'-most nucleotide of a particular compound.

"5-methylcytosine" means a cytosine with a methyl group attached to the 5 position.

"About" means within ±10% of a value. For example, if it is stated, "the compounds affected about 70% inhibition of Inc05", it is implied that Inc05 levels are inhibited within a range of 60% and 80%.

"Administration" or "administering" refers to routes of introducing a compound or composition provided herein to an individual to perform its intended function. An example of a route of administration that can be used includes, but is not limited to parenteral administration, such as subcutaneous, intravenous, or intramuscular injection or infusion.

"Administered concomitantly" or "co-administration" means administration of two or more compounds in any manner in which the pharmacological effects of both are manifest in the patient. Concomitant administration does not require that both compounds be administered in a single pharmaceutical composition, in the same dosage form, by the same route of administration, or at the same time. The effects of both compounds need not manifest themselves at the same time. The effects need only be overlapping for a period of time and need not be coextensive. Concomitant administration or co-administration encompasses administration in parallel or sequentially.

"Amelioration" refers to an improvement or lessening of at least one indicator, sign, or symptom of an associated disease, disorder, or condition. In certain embodiments, amelioration includes a delay or slowing in the progression or severity of one or more indicators of a condition or disease. The progression or severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable and/or measurable activity attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound to the target.

"Antisense compound" means a compound comprising an oligonucleotide and optionally one or more additional features, such as a conjugate group or terminal group. Examples of antisense compounds include single-stranded and double-stranded compounds, such as, oligonucleotides, ribozymes, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means an oligonucleotide having a nucleobase sequence that is complementary to a target nucleic acid or region or segment thereof. In certain embodiments, an antisense oligonucleotide is specifically hybridizable to a target nucleic acid or region or segment thereof.

"Bicyclic nucleoside" or "BNA" means a nucleoside comprising a bicyclic sugar moiety. "Bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Cell-targeting moiety" means a conjugate group or portion of a conjugate group that is capable of binding to a particular cell type or particular cell types.

"cEt" or "constrained ethyl" means a bicyclic furanosyl sugar moiety comprising a bridge connecting the 4'-carbon and the 2'-carbon, wherein the bridge has the formula: 4'-CH(CH$_3$)—O-2'.

"Chemical modification" in a compound describes the substitutions or changes through chemical reaction, of any of the units in the compound. "Modified nucleoside" means a nucleoside having, independently, a modified sugar moiety and/or modified nucleobase. "Modified oligonucleotide" means an oligonucleotide comprising at least one modified internucleoside linkage, a modified sugar, and/or a modified nucleobase.

"Chemically distinct region" refers to a region of a compound that is in some way chemically different than another region of the same compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

"Cleavable moiety" means a bond or group of atoms that is cleaved under physiological conditions, for example, inside a cell, an animal, or a human.

"Complementary" in reference to an oligonucleotide means the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine ($^mC$) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Conjugate group" means a group of atoms that is attached to an oligonucleotide. Conjugate groups include a conjugate moiety and a conjugate linker that attaches the conjugate moiety to the oligonucleotide.

"Conjugate linker" means a group of atoms comprising at least one bond that connects a conjugate moiety to an oligonucleotide. "Conjugate moiety" means a group of atoms that is attached to an oligonucleotide via a conjugate linker.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Designing" or "Designed to" refer to the process of designing a compound that specifically hybridizes with a selected nucleic acid molecule.

"Diluent" means an ingredient in a composition that lacks pharmacological activity, but is pharmaceutically necessary or desirable. For example, the diluent in an injected composition can be a liquid, e.g. saline solution.

"Differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

"Dose" means a specified quantity of a compound or pharmaceutical agent provided in a single administration, or in a specified time period. In certain embodiments, a dose may be administered in two or more boluses, tablets, or injections. For example, in certain embodiments, where subcutaneous administration is desired, the desired dose may require a volume not easily accommodated by a single injection. In such embodiments, two or more injections may be used to achieve the desired dose. In certain embodiments, a dose may be administered in two or more injections to minimize injection site reaction in an individual. In other embodiments, the compound or pharmaceutical agent is administered by infusion over an extended period of time or continuously. Doses may be stated as the amount of pharmaceutical agent per hour, day, week or month.

"Dosing regimen" is a combination of doses designed to achieve one or more desired effects.

"Double-stranded compound" means a compound comprising two oligomeric compounds that are complementary to each other and form a duplex, and wherein one of the two said oligomeric compounds comprises an oligonucleotide.

"Effective amount" means the amount of compound sufficient to effectuate a desired physiological outcome in an individual in need of the compound. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Gapmer" means an oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Hybridization" means annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

"Immediately adjacent" means there are no intervening elements between the immediately adjacent elements of the same kind (e.g. no intervening nucleobases between the immediately adjacent nucleobases).

"Individual" means a human or non-human animal selected for treatment or therapy.

"Inhibiting the expression or activity" refers to a reduction or blockade of the expression or activity relative to the expression of activity in an untreated or control sample and does not necessarily indicate a total elimination of expression or activity.

"Internucleoside linkage" means a group or bond that forms a covalent linkage between adjacent nucleosides in an oligonucleotide. "Modified internucleoside linkage" means any internucleoside linkage other than a naturally occurring, phosphate internucleoside linkage. Non-phosphate linkages are referred to herein as modified internucleoside linkages.

"Lengthened oligonucleotides" are those that have one or more additional nucleosides relative to an oligonucleotide disclosed herein, e.g. a parent oligonucleotide.

"Linked nucleosides" means adjacent nucleosides linked together by an internucleoside linkage.

"lnc05" means long intergenic non-protein coding RNA 862 (also known as LINC00862, C1orf98, chromosome 1 open reading frame 98, small integral membrane protein 16, SMIM16, and NR_040064) and refers to any nucleic acid of lnc05. For example, in certain embodiments, lnc05 includes a DNA sequence encoding lnc05, an RNA sequence transcribed from DNA encoding lnc05 (including genomic DNA comprising introns and exons). The target may be referred to in either upper or lower case.

"lnc05-specific inhibitor" refers to any agent capable of specifically inhibiting lnc05 expression or activity at the molecular level. For example, lnc05-specific inhibitors include nucleic acids (including antisense compounds), peptides, antibodies, small molecules, and other agents capable of inhibiting the expression or activity of lnc05.

"Mismatch" or "non-complementary" means a nucleobase of a first oligonucleotide that is not complementary to the corresponding nucleobase of a second oligonucleotide or target nucleic acid when the first and second oligonucleotides are aligned. For example, nucleobases including but not limited to a universal nucleobase, inosine, and hypoxanthine, are capable of hybridizing with at least one nucleobase but are still mismatched or non-complementary with respect to nucleobase to which it hybridized. As another example, a nucleobase of a first oligonucleotide that is not capable of hybridizing to the corresponding nucleobase of a second oligonucleotide or target nucleic acid when the first and second oligonucleotides are aligned is a mismatch or non-complementary nucleobase.

"Modulating" refers to changing or adjusting a feature in a cell, tissue, organ or organism. For example, modulating lnc05 can mean to increase or decrease the level of lnc05 in a cell, tissue, organ or organism. A "modulator" effects the change in the cell, tissue, organ or organism. For example, a compound can be a modulator of lnc05 that decreases the amount of lnc05 in a cell, tissue, organ or organism.

"MOE" means methoxyethyl.

"Monomer" refers to a single unit of an oligomer. Monomers include, but are not limited to, nucleosides and nucleotides.

"Motif" means the pattern of unmodified and/or modified sugar moieties, nucleobases, and/or internucleoside linkages, in an oligonucleotide.

"Natural" or "naturally occurring" means found in nature.

"Non-bicyclic modified sugar" or "non-bicyclic modified sugar moiety" means a modified sugar moiety that comprises a modification, such as a substituent, that does not form a bridge between two atoms of the sugar to form a second ring.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase, and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase.

"Oligomeric compound" means a compound comprising a single oligonucleotide and optionally one or more additional features, such as a conjugate group or terminal group.

"Oligonucleotide" means a polymer of linked nucleosides each of which can be modified or unmodified, independent one from another. Unless otherwise indicated, oligonucleotides consist of 8-80 linked nucleosides. "Modified oligonucleotide" means an oligonucleotide, wherein at least one sugar, nucleobase, or internucleoside linkage is modified.

"Unmodified oligonucleotide" means an oligonucleotide that does not comprise any sugar, nucleobase, or internucleoside modification.

"Parent oligonucleotide" means an oligonucleotide whose sequence is used as the basis of design for more oligonucleotides of similar sequence but with different lengths, motifs, and/or chemistries. The newly designed oligonucleotides may have the same or overlapping sequence as the parent oligonucleotide.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Pharmaceutically acceptable carrier or diluent" means any substance suitable for use in administering to an individual. For example, a pharmaceutically acceptable carrier can be a sterile aqueous solution, such as PBS or water-for-injection.

"Pharmaceutically acceptable salts" means physiologically and pharmaceutically acceptable salts of compounds, such as oligomeric compounds or oligonucleotides, i.e., salts that retain the desired biological activity of the parent compound and do not impart undesired toxicological effects thereto.

"Pharmaceutical agent" means a compound that provides a therapeutic benefit when administered to an individual.

"Pharmaceutical composition" means a mixture of substances suitable for administering to an individual. For example, a pharmaceutical composition may comprise one or more compounds or salt thereof and a sterile aqueous solution.

"Phosphorothioate linkage" means a modified phosphate linkage in which one of the non-bridging oxygen atoms is replaced with a sulfur atom. A phosphorothioate internucleoside linkage is a modified internucleoside linkage.

"Phosphorus moiety" means a group of atoms comprising a phosphorus atom. In certain embodiments, a phosphorus moiety comprises a mono-, di-, or tri-phosphate, or phosphorothioate.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligomeric compound.

"Prevent" refers to delaying or forestalling the onset, development or progression of a disease, disorder, or condition for a period of time from minutes to indefinitely.

"Prodrug" means a compound in a form outside the body which, when administered to an individual, is metabolized to another form within the body or cells thereof. In certain embodiments, the metabolized form is the active, or more active, form of the compound (e.g., drug). Typically conversion of a prodrug within the body is facilitated by the action of an enzyme(s) (e.g., endogenous or viral enzyme) or chemical(s) present in cells or tissues, and/or by physiologic conditions.

"Reduce" means to bring down to a smaller extent, size, amount, or number.

"RefSeq No." is a unique combination of letters and numbers assigned to a sequence to indicate the sequence is for a particular target transcript (e.g., target gene). Such sequence and information about the target gene (collectively, the gene record) can be found in a genetic sequence database. Genetic sequence databases include the NCBI Reference Sequence database, GenBank, the European Nucleotide Archive, and the DNA Data Bank of Japan (the latter three forming the International Nucleotide Sequence Database Collaboration or INSDC).

"Region" is defined as a portion of the target nucleic acid having at least one identifiable structure, function, or characteristic.

"RNAi compound" means an antisense compound that acts, at least in part, through RISC or Ago2, but not through RNase H, to modulate a target nucleic acid and/or protein encoded by a target nucleic acid. RNAi compounds include, but are not limited to double-stranded siRNA, single-stranded RNA (ssRNA), and microRNA, including microRNA mimics.

"Segments" are defined as smaller or sub-portions of regions within a nucleic acid.

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded" in reference to a compound means the compound has only one oligonucleotide. "Self-complementary" means an oligonucleotide that at least partially hybridizes to itself. A compound consisting of one oligonucleotide, wherein the oligonucleotide of the compound is self-complementary, is a single-stranded compound. A single-stranded compound may be capable of binding to a complementary compound to form a duplex.

"Sites," are defined as unique nucleobase positions within a target nucleic acid.

"Specifically hybridizable" refers to an oligonucleotide having a sufficient degree of complementarity between the oligonucleotide and a target nucleic acid to induce a desired effect, while exhibiting minimal or no effects on non-target nucleic acids. In certain embodiments, specific hybridization occurs under physiological conditions.

"Specifically inhibit" a target nucleic acid means to reduce or block expression of the target nucleic acid while exhibiting fewer, minimal, or no effects on non-target nucleic acids reduction and does not necessarily indicate a total elimination of the target nucleic acid's expression.

"Standard cell assay" means assay(s) described in the Examples and reasonable variations thereof "Standard in vivo experiment" means the procedure(s) described in the Example(s) and reasonable variations thereof.

"Sugar moiety" means an unmodified sugar moiety or a modified sugar moiety. "Unmodified sugar moiety" or "unmodified sugar" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. "Modified sugar moiety" or "modified sugar" means a modified furanosyl sugar moiety or a sugar surrogate. "Modified furanosyl sugar moiety" means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars.

"Sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

"Synergy" or "synergize" refers to an effect of a combination that is greater than additive of the effects of each component alone at the same doses.

"Target gene" refers to a gene encoding a target.

"Targeting" means specific hybridization of a compound that to a target nucleic acid in order to induce a desired effect.

"Target nucleic acid," "target RNA," "target RNA transcript" and "nucleic acid target" all mean a nucleic acid capable of being targeted by compounds described herein.

"Target region" means a portion of a target nucleic acid to which one or more compounds is targeted.

"Target segment" means the sequence of nucleotides of a target nucleic acid to which a compound described herein is targeted. "5' target site" refers to the 5'-most nucleotide of a target segment. "3' target site" refers to the 3'-most nucleotide of a target segment.

"Terminal group" means a chemical group or group of atoms that is covalently linked to a terminus of an oligonucleotide.

"Therapeutically effective amount" means an amount of a compound, pharmaceutical agent, or composition that provides a therapeutic benefit to an individual.

"Treat" refers to administering a compound or pharmaceutical composition to an individual in order to effect an alteration or improvement of a disease, disorder, or condition in the individual.

Certain Embodiments

Certain embodiments provide methods, compounds, and compositions for modulating a cancer condition, or a symptom thereof, in an individual by administering the compound or composition to the individual, wherein the compound or composition comprises a lnc05 modulator. Modulation of lnc05 can lead to a decrease of lnc05 level or expression in order to treat, prevent, ameliorate or delay cancer, or a symptom thereof. In certain embodiments, the lnc05 modulator is a lnc05-specific inhibitor. In certain embodiments, the cancer is hepatocellular carcinoma. In certain embodiments, the cancer is breast cancer. In certain embodiments, lnc05-specific inhibitors are nucleic acids (including antisense compounds), peptides, antibodies, small molecules, and other agents capable of inhibiting the expression or activity of lnc05. In certain embodiments, the individual is human.

In certain embodiments disclosed herein, lnc05 has the sequence recited in SEQ ID No: 1-5.

Certain embodiments disclosed herein provide compounds or compositions comprising a lnc05 modulator. Such compounds or compositions are useful to treat, prevent, ameliorate or delay cancer, or a symptom thereof. In certain embodiments, the cancer is hepatocellular carcinoma. In certain embodiments. the cancer is breast cancer. In certain embodiments, the lnc05 modulator is a lnc05-specific inhibitor. In certain embodiments, the lnc05-specific inhibitor is a nucleic acid, polypeptide, antibody, small molecules, or other agent capable of inhibiting the expression or activity of lnc05. In certain embodiments, the lnc05-specific inhibitor is a nucleic acid targeting lnc05. In certain embodiments, the nucleic acid is single stranded. In certain embodiments, the nucleic acid is double stranded. In certain embodiments, the compound or composition comprises an antisense compound. In any of the foregoing embodiments, the compound or composition comprises an oligomeric compound. In certain embodiments, the compound or composition comprises an oligonucleotide targeting lnc05. In certain embodiments, the oligonucleotide is single stranded. In certain embodiments, the compound comprises deoxyribonucleotides. In certain embodiments, the compound comprises ribonucleotides and is double-stranded. In certain embodiments, the oligonucleotide is a modified oligonucleotide. In certain embodiments, the modified oligonucleotide is single stranded.

In any of the foregoing embodiments, the compound can comprise a modified oligonucleotide consisting of 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides.

In certain embodiments, at least one internucleoside linkage of said modified oligonucleotide is a modified internucleoside linkage. In certain embodiments, at least one internucleoside linkage is a phosphorothioate internucleoside linkage. In certain embodiments, the internucleoside linkages are phosphorothioate linkages and phosphate ester linkages.

In certain embodiments, any of the foregoing oligonucleotides comprises at least one modified sugar. In certain embodiments, at least one modified sugar comprises a 2'-O-methoxyethyl group. In certain embodiments, at least one modified sugar is a bicyclic sugar, such as a 4'-CH(CH$_3$)—O-2' group, a 4'-CH$_2$—O-2' group, or a 4'-(CH$_2$)$_2$—O-2' group.

In certain embodiments, at least one nucleoside of said modified oligonucleotide comprises a modified nucleobase. In certain embodiments, the modified nucleobase is a 5-methylcytosine.

Certain embodiments disclosed herein provide a compound or composition comprising a modified oligonucleotide comprising: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar. In certain embodiments, at least one internucleoside linkage is a phosphorothioate linkage. In certain embodiments, and at least one cytosine is a 5-methylcytosine.

In certain embodiments, the compounds or compositions disclosed herein further comprise a pharmaceutically acceptable carrier or diluent.

In certain embodiments, the compound or composition is co-administered with a second agent. In certain embodiments, the compound or composition and the second agent are administered concomitantly.

Certain embodiments disclosed herein provide a method of treating, preventing, delaying or ameliorating cancer in an individual comprising administering to the individual a compound or composition comprising a lnc05-specific inhibitor. In certain embodiments, the cancer is hepatocellular carcinoma. In certain embodiments, the cancer is breast cancer. In certain embodiments, the lnc05-specific inhibitor is a nucleic acid, peptide, antibody, small molecule or other agent capable of inhibiting the expression or activity of lnc05. In certain embodiments, the lnc05-specific inhibitor comprises an antisense compound or an oligomeric compound. In certain embodiments, the compound or composition comprises a modified oligonucleotide. In certain embodiments, the modified oligonucleotide is 10 to 30 linked nucleosides in length. In certain embodiments, the individual is human.

In certain embodiments, a method of inhibiting expression or activity of lnc05 in a cell comprises contacting the cell with a lnc05-specific inhibitor, thereby inhibiting expression or activity of lnc05 in the cell. In certain embodiments, the cell is a hepatocyte or liver cell. In certain embodiments the cell is a mammary cell. In certain embodiments, the cell is in the liver tissue. In certain embodiments, the cell is in the breast tissue. In certain embodiments, the cell is in the liver of an individual who has, or is at risk of having hepatocellular carcinoma. In certain embodiments, the cell is in the mammary gland of an individual who has, or is at risk of having breast cancer. In certain embodiments, the lnc05-specific inhibitor is targeted to lnc05, such as an oligonucleotide targeted to lnc05.

Certain embodiments disclosed herein provide a method of treating an individual at risk for cancer comprising administering to the individual a compound or composition comprising a lnc05-specific inhibitor. In certain embodiments, the cancer is hepatocellular carcinoma. In certain embodiments, the cancer is breast cancer. In certain embodiments, the lnc05-specific inhibitor is a nucleic acid, peptide, antibody, small molecule or other agent capable of inhibiting the expression or activity of lnc05. In certain embodiments, the compound or composition comprises an antisense compound or an oligomeric compound. In certain embodiments, the compound or composition comprises a modified oligonucleotide. In certain embodiments, the individual is human.

In certain embodiments, the administering is parenteral administration. In certain embodiments, the parenteral administration is subcutaneous administration. In certain embodiments, the parenteral administration is intravenous administration.

Certain embodiments provide compounds and compositions described herein for use in therapy. In certain embodiments, the therapy is used in treating, preventing, delaying the onset or slowing progression of a disease related to elevated expression or activity of lnc05. In certain embodiments, the disease is cancer. In certain embodiments, the cancer is hepatocellular carcinoma. In certain embodiments, the cancer is breast cancer. In certain embodiments, the therapy is used to stop tumor initiation, decrease tumor progression, cell proliferation, colony formation, metastasis, or a combination thereof. In certain embodiments, the compound or composition comprises a modified oligonucleotide 8 to 80 linked nucleosides in length. In certain embodiments, the modified oligonucleotide is 10 to 30 linked nucleosides in length. In certain embodiments, the compound or composition is administered to the individual parenterally.

Certain embodiments disclosed herein provide compounds or compositions described herein comprising a lnc05 modulator for the manufacture or preparation of a medicament for therapy. In certain embodiments, the therapy is used in treating, preventing, delaying the onset or slowing progression of a disease related to elevated expression or activity of lnc05. In certain embodiments, the disease is cancer. In certain embodiments, the cancer is hepatocellular carcinoma. In certain embodiments, the cancer is breast cancer. In certain embodiments, the therapy is used to stop tumor initiation, decrease tumor progression, cell proliferation, colony formation, metastasis, or a combination thereof. In certain embodiments, the compound or composition comprises a modified oligonucleotide 8 to 80 linked nucleosides in length. In certain embodiments, the modified oligonucleotide is 10 to 30 linked nucleosides in length. In certain embodiments, the compound or composition is administered to the individual parenterally.

Certain embodiments disclosed herein provide uses of a compound or composition comprising a modified oligonucleotide with: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar. In certain embodiments, at least one internucleoside linkage is a phosphorothioate linkage. In certain embodiments, and at least one cytosine is a 5-methylcytosine.

In certain embodiments, the compounds or compositions disclosed herein further comprise a pharmaceutically acceptable carrier or diluent.

In certain embodiments, the individual is a human.

In certain embodiments, administration comprises parenteral administration. In certain embodiments, parenteral administration comprises subcutaneous administration. In certain embodiments, parenteral administration comprises intravenous administration.

In certain embodiments, the compounds or compositions disclosed herein are designated as a first agent and the methods or uses disclosed herein further comprise administering a second agent. In certain embodiments, the first agent and the second agent are co-administered. In certain embodiments the first agent and the second agent are co-administered sequentially or concomitantly.

Certain Indications

Certain embodiments provided herein relate to methods of inhibiting lnc05 expression or activity, which can be useful for treating, preventing, or ameliorating a disease associated with lnc05 in an individual, by administration of a compound or composition that targets lnc05. In certain embodiments, such a compound or composition comprises a lnc05-specific inhibitor. In certain embodiments, the compound comprises an antisense compound or an oligomeric compound targeted to lnc05. In certain embodiments, the compound comprises a modified oligonucleotide targeted to lnc05.

In certain embodiments, a method of treating, preventing, or ameliorating a disease associated with a cancer in an individual comprises administering to the individual a compound or composition comprising a lnc05-specific inhibitor, thereby treating, preventing, or ameliorating the disease. In certain embodiments, the cancer is hepatocellular carcinoma. In certain embodiments, the cancer is breast cancer. In certain embodiments, the individual is human. In certain embodiments, the lnc05-specific inhibitor is a nucleic acid, peptide, antibody, small molecule or other agent capable of inhibiting the expression or activity of the lnc05. In certain embodiments, the lnc05-specific inhibitor is an antisense compound or an oligomeric compound targeted to lnc05. In certain embodiments, the lnc05-specific inhibitor is oligonucleotide targeted to lnc05. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded. In certain embodiments, the lnc05-specific inhibitor is administered to the individual parenterally.

Certain embodiments disclosed herein provide a method of reducing tumor progression in an individual comprising administering to the individual a compound or composition comprising a lnc05-specific inhibitor. In certain embodiments, the individual is human. In certain embodiments, the lnc05-specific inhibitor is a nucleic acid, peptide, antibody, small molecule or other agent capable of inhibiting the expression or activity of lnc05. In certain embodiments, the lnc05-specific inhibitor is an antisense compound or an oligomeric compound targeted to lnc05. In certain embodiments, the lnc05-specific inhibitor is oligonucleotide targeted to lnc05. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded. In certain embodiments, the lnc05-specific inhibitor is administered to the individual parenterally.

Certain embodiments disclosed herein provide a method of stopping or impeding tumor initiation in an individual comprising administering to the individual a compound or composition comprising a lnc05-specific inhibitor. In certain embodiments, the individual is human. In certain embodiments, the lnc05-specific inhibitor is a nucleic acid, peptide, antibody, small molecule or other agent capable of inhibiting the expression or activity of lnc05. In certain embodiments, the lnc05-specific inhibitor is an antisense compound or an oligomeric compound targeted to lnc05. In certain embodiments, the lnc05-specific inhibitor is oligonucleotide targeted to lnc05. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded. In certain embodiments, the lnc05-specific inhibitor is administered to the individual parenterally.

Certain embodiments disclosed herein provide a method of reducing cell proliferation in an individual comprising administering to the individual a compound or composition comprising a lnc05-specific inhibitor. In certain embodiments, the individual is human. In certain embodiments, the lnc05-specific inhibitor is a nucleic acid, peptide, antibody, small molecule or other agent capable of inhibiting the expression or activity of lnc05. In certain embodiments, the lnc05-specific inhibitor is an antisense compound or an oligomeric compound targeted to lnc05. In certain embodiments, the lnc05-specific inhibitor is oligonucleotide targeted to lnc05. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded. In certain embodiments, the lnc05-specific inhibitor is administered to the individual parenterally.

Certain embodiments disclosed herein provide a method of reducing colony formation in an individual comprising administering to the individual a compound or composition comprising a lnc05-specific inhibitor. In certain embodiments, the individual is human. In certain embodiments, the lnc05-specific inhibitor is a nucleic acid, peptide, antibody, small molecule or other agent capable of inhibiting the expression or activity of lnc05. In certain embodiments, the lnc05-specific inhibitor is an antisense compound or an oligomeric compound targeted to lnc05. In certain embodiments, the lnc05-specific inhibitor is oligonucleotide targeted to lnc05. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded. In certain embodiments, the lnc05-specific inhibitor is administered to the individual parenterally.

Certain embodiments disclosed herein provide a method of reducing metastasis in an individual comprising administering to the individual a compound or composition comprising a lnc05-specific inhibitor. In certain embodiments, the individual is human. In certain embodiments, the lnc05-specific inhibitor is a nucleic acid, peptide, antibody, small molecule or other agent capable of inhibiting the expression or activity of lnc05. In certain embodiments, the lnc05-specific inhibitor is an antisense compound or an oligomeric compound targeted to lnc05. In certain embodiments, the lnc05-specific inhibitor is oligonucleotide targeted to lnc05. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded. In certain embodiments, the lnc05-specific inhibitor is administered to the individual parenterally.

In certain embodiments, administering a compound or composition disclosed herein regulates or reduces one or more of tumor initiation, tumor progression, cell proliferation, colony formation, or metastasis, or a combination thereof. In certain embodiments, tumor progression is independently reduced by at least 5%, at least 10%, at least 20%, at least 30%, at least 35%, at least 40%, at least 45% or at least 50%. In certain embodiments, cell proliferation is independently increased by at least 5%, at least 10%, at least 20%, at least 30%, at least 35%, at least 40%, at least 45% or at least 50%. In certain embodiments, colony formation is independently increased by at least 5%, at least 10%, at least 20%, at least 30%, at least 35%, at least 40%, at least 45% or at least 50%. In certain embodiments, metastasis is independently increased by at least 5%, at least 10%, at least 20%, at least 30%, at least 35%, at least 40%, at least 45% or at least 50%.

Certain embodiments are drawn to a compound or composition comprising a lnc05-specific inhibitor for use in treating cancer. In certain embodiments, the cancer is hepatocellular carcinoma. In certain embodiments, the cancer is breast cancer. In certain embodiments, the lnc05-specific inhibitor is a nucleic acid, peptide, antibody, small molecule or other agent capable of inhibiting the expression or activity of lnc05. In certain embodiments, the lnc05-specific inhibitor is an antisense compound or an oligomeric compound targeted to lnc05. In certain embodiments, the lnc05-specific inhibitor is oligonucleotide targeted to lnc05. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded. In certain embodiments, the lnc05-specific inhibitor is administered to the individual parenterally.

In certain embodiments, use of a compound or composition disclosed herein results in tumor progression independently reduced by at least 5%, at least 10%, at least 20%, at least 30%, at least 35%, at least 40%, at least 45% or at least 50%. In certain embodiments, use of a compound or composition disclosed herein results in cell proliferation independently decreased by at least 5%, at least 10%, at least 20%, at least 30%, at least 35%, at least 40%, at least 45% or at least 50%. In certain embodiments, use of a compound or composition disclosed herein results in colony formation independently decreased by at least 5%, at least 10%, at least 20%, at least 30%, at least 35%, at least 40%, at least 45% or at least 50%. In certain embodiments, use of a compound or composition disclosed herein results in metastasis independently decreased by at least 5%, at least 10%, at least 20%, at least 30%, at least 35%, at least 40%, at least 45% or at least 50%.

Certain embodiments provide the use of a compound or composition as described herein in the manufacture or preparation of a medicament for treating, ameliorating, delaying or preventing one or more diseases, disorders, conditions, symptoms or physiological markers associated with lnc05. In certain embodiments, the compound or composition as described herein is used in the manufacture or preparation of a medicament for treating, ameliorating, delaying or preventing cancer, or a symptom or physiological marker thereof. In certain embodiments, the cancer is hepatocellular carcinoma. In certain embodiments, the cancer is breast cancer. In certain embodiments, the compound or composition comprises a nucleic acid, peptide, antibody, small molecule or other agent capable of inhibiting the expression or activity of lnc05. In certain embodiments, the compound or composition comprises an antisense compound or an oligomeric compound targeted to lnc05. In certain embodiments, the compound or composition comprises an oligonucleotide targeted to lnc05. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound or composition comprising a modified oligonucleotide can be single-stranded. In certain embodiments, the compound or composition comprising a modified oligonucleotide can be double-stranded.

Certain embodiments are drawn to use of a compound or composition for the manufacture or preparation of a medicament for treating cancer. Examples of such cancers are hepatocellular carcinoma. In certain embodiments, the cancer is breast cancer. In certain embodiments, the compound or composition comprises a nucleic acid, peptide, antibody, small molecule or other agent capable of inhibiting the expression or activity of lnc05. In certain embodiments, the compound or composition comprises an antisense compound or an oligomeric compound targeted to lnc05. In certain embodiments, the compound or composition comprises an oligonucleotide targeted to lnc05. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound or composition comprising a modified oligonucleotide can be single-stranded. In certain embodiments, the compound or composition comprising a modified oligonucleotide can be double-stranded.

Certain embodiments are drawn to use of a compound or composition for the manufacture or preparation of a medicament for decreasing tumor progression, cell proliferation, colony formation, metastasis, or a combination thereof in an individual having or at risk of having cancer. In certain embodiments, the cancer is hepatocellular carcinoma. In certain embodiments, the cancer is breast cancer. In certain embodiments, the compound or composition comprises a nucleic acid, peptide, antibody, small molecule or other agent capable of inhibiting the expression or activity of lnc05. In certain embodiments, the compound or composition comprises an antisense compound or an oligomeric compound targeted to lnc05. In certain embodiments, the compound or composition comprises an oligonucleotide targeted to lnc05. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound or composition comprising a modified oligonucleotide can be single-stranded. In certain embodiments, the compound or composition comprising a modified oligonucleotide can be double-stranded.

In any of the foregoing methods or uses, the compound or composition comprises an antisense compound targeted to lnc05. In certain embodiments, the compound comprises an oligonucleotide, for example an oligonucleotide consisting of 8 to 80 linked nucleosides, 10 to 30 linked nucleosides, 12 to 30 linked nucleosides, or 20 linked nucleosides. In certain embodiments, the oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide comprises a gap segment consisting of linked deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar.

In any of the foregoing methods or uses, the compound or composition comprises or consists of a modified oligonucleotide 12 to 30 linked nucleosides in length, wherein the modified oligonucleotide comprises:

a gap segment consisting of linked 2'-deoxynucleosides;
a 5' wing segment consisting of linked nucleosides; and
a 3' wing segment consisting of linked nucleosides;
wherein the gap segment is positioned between the 5' wing segment and the 3' wing segment and wherein each nucleoside of each wing segment comprises a modified sugar.

In any of the foregoing methods or uses, the compound or composition can be administered parenterally. For example, in certain embodiments the compound or composition can be administered through injection or infusion. Parenteral administration includes subcutaneous administration, intravenous administration, intramuscular administration, intraarterial administration, intraperitoneal administration, or intracranial administration. In certain embodiments, the parenteral administration is subcutaneous administration. In certain embodiments, the parenteral administration is intravenous administration. In certain embodiments, the compound or composition is co-administered with a second agent. In certain embodiments, the compound or composition and the second agent are administered concomitantly.

Certain Compounds

In certain embodiments, compounds described herein are antisense compounds. In certain embodiments, the antisense compound comprises or consists of an oligomeric compound. In certain embodiments, the oligomeric compound comprises a modified oligonucleotide. In certain embodiments, the modified oligonucleotide has a nucleobase sequence complementary to that of a target nucleic acid.

In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single-stranded. Such a single-stranded compound or antisense compound comprises or consists of an oligomeric compound. In certain embodiments, such an oligomeric compound comprises or consists of an oligonucleotide. In certain embodiments, the oligonucleotide is an antisense oligonucleotide. In certain embodiments, the oligonucleotide is modified. In certain embodiments, the oligonucleotide of a single-stranded antisense compound or oligomeric compound comprises a self-complementary nucleobase sequence.

In certain embodiments, compounds are double-stranded. Such double-stranded compounds comprise a first modified oligonucleotide having a region complementary to a target nucleic acid and a second modified oligonucleotide having a region complementary to the first modified oligonucleotide. In certain embodiments, the modified oligonucleotide is an RNA oligonucleotide. In such embodiments, the thymine nucleobase in the modified oligonucleotide is replaced by a uracil nucleobase. In certain embodiments, compound comprises a conjugate group. In certain embodiments, each modified oligonucleotide is 12-30 linked nucleosides in length.

In certain embodiments, compounds are double-stranded. Such double-stranded compounds comprise a first oligomeric compound having a region complementary to a target nucleic acid and a second oligomeric compound having a region complementary to the first oligomeric compound. The first oligomeric compound of such double stranded compounds typically comprises or consists of a modified oligonucleotide. The oligonucleotide of the second oligomeric compound of such double-stranded compound may be modified or unmodified. The oligomeric compounds of double-stranded compounds may include non-complementary overhanging nucleosides.

Examples of single-stranded and double-stranded compounds include but are not limited to oligonucleotides, siRNAs, microRNA targeting oligonucleotides, and single-stranded RNAi compounds, such as small hairpin RNAs (shRNAs), single-stranded siRNAs (ssRNAs), and microRNA mimics.

In certain embodiments, a compound described herein has a nucleobase sequence that, when written in the 5' to 3' direction, comprises the reverse complement of the target segment of a target nucleic acid to which it is targeted.

In certain embodiments, a compound described herein comprises an oligonucleotide 10 to 30 linked subunits in length. In certain embodiments, a compound described herein comprises an oligonucleotide is 12 to 30 linked subunits in length. In certain embodiments, a compound described herein comprises an oligonucleotide 12 to 22 linked subunits in length. In certain embodiments, a compound described herein comprises an oligonucleotide 14 to 30 linked subunits in length. In certain embodiments, a compound described herein comprises an oligonucleotide 14 to 20 linked subunits in length. In certain embodiments, a compound described herein comprises an oligonucleotide 15 to 30 linked subunits in length. In certain embodiments, a compound described herein comprises an oligonucleotide 15 to 20 linked subunits in length. In certain embodiments, a compound described herein comprises an oligonucleotide 16 to 30 linked subunits in length. In certain embodiments, a compound described herein comprises an oligonucleotide 16 to 20 linked subunits in length. In certain embodiments, a compound described herein comprises an oligonucleotide 17 to 30 linked subunits in length. In certain embodiments, a compound described herein comprises an oligonucleotide 17 to 20 linked subunits in length. In certain embodiments, a compound described herein comprises an oligonucleotide 18 to 30 linked subunits in length. In certain embodiments, a compound described herein comprises an oligonucleotide 18 to 21 linked subunits in length. In certain embodiments, a compound described herein comprises an oligonucleotide 18 to 20 linked subunits in length. In certain embodiments, a compound described herein comprises an oligonucleotide 20 to 30 linked subunits in length. In other words, such oligonucleotides are from 10 to 30 subunits, 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the linked subunits are nucleotides, nucleosides, or nucleobases.

In certain embodiments, compounds may be shortened or truncated. For example, a single subunit may be deleted from the 5' end (5' truncation), or alternatively from the 3' end (3' truncation). A shortened or truncated compound targeted to a lnc05 nucleic acid may have two subunits deleted from the 5' end, or alternatively may have two subunits deleted from the 3' end, of the compound. Alternatively, the deleted nucleosides may be dispersed throughout the compound.

When a single additional subunit is present in a lengthened compound, the additional subunit may be located at the 5' or 3' end of the compound. When two or more additional subunits are present, the added subunits may be adjacent to each other, for example, in a compound having two subunits added to the 5' end (5' addition), or alternatively to the 3' end (3' addition), of the compound. Alternatively, the added subunits may be dispersed throughout the compound.

It is possible to increase or decrease the length of a compound, such as an oligonucleotide, and/or introduce mismatch bases without eliminating activity (Woolf et al. (Proc. Natl. Acad. Sci. USA 89:7305-7309, 1992; Gautschi et al. *J. Natl. Cancer Inst.* 93:463-471, March 2001; Maher and Dolnick *Nuc. Acid. Res.* 16:3341-3358,1988). However, seemingly small changes in oligonucleotide sequence, chemistry and motif can make large differences in one or more of the many properties required for clinical development (Seth et al. *J. Med. Chem.* 2009, 52, 10; Egli et al. *J. Am. Chem. Soc.* 2011, 133, 16642).

In certain embodiments, compounds described herein are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics.

In certain embodiments, a double-stranded compound comprises a first strand comprising the nucleobase sequence complementary to a target region of a lnc05 nucleic acid and a second strand. In certain embodiments, the double-stranded compound comprises ribonucleotides in which the first strand has uracil (U) in place of thymine (T) and is complementary to a target region. In certain embodiments, a double-stranded compound comprises (i) a first strand comprising a nucleobase sequence complementary to a target region of a lnc05 nucleic acid, and (ii) a second strand. In certain embodiments, the double-stranded compound comprises one or more modified nucleotides in which the 2' position in the sugar contains a halogen (such as fluorine group; 2'-F) or contains an alkoxy group (such as a methoxy group; 2'-OMe). In certain embodiments, the double-stranded compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the dsRNA compound. In certain embodiments, the double-stranded compound comprises one or more linkages between adjacent nucleotides other than a naturally-occurring phosphodiester linkage. Examples of such linkages include phosphoramide, phosphorothioate, and phosphorodithioate linkages. The double-stranded compounds may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000. In certain embodiments, the first strand of the double-stranded compound is an siRNA guide strand and the second strand of the double-stranded compound is an siRNA passenger strand. In certain embodiments, the second strand of the double-stranded compound is complementary to the first strand. In certain embodiments, each strand of the double-stranded compound consists of 16, 17, 18, 19, 20, 21, 22, or 23 linked nucleosides.

In certain embodiments, a single-stranded compound described herein can comprise any of the oligonucleotide sequences targeted to lnc05 described herein. In certain embodiments, such a single-stranded compound is a single-stranded RNAi (ssRNAi) compound. In certain embodiments, a ssRNAi compound comprises the nucleobase sequence complementary to a target region of a lnc05 nucleic acid. In certain embodiments, the ssRNAi compound comprises ribonucleotides in which uracil (U) is in place of thymine (T). In certain embodiments, ssRNAi compound comprises a nucleobase sequence complementary to a target region of a lnc05 nucleic acid. In certain embodiments, a ssRNAi compound comprises one or more modified nucleotides in which the 2' position in the sugar contains a halogen (such as fluorine group; 2'-F) or contains an alkoxy group (such as a methoxy group; 2'-OMe). In certain embodiments, a ssRNAi compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the ssRNAi compound. In certain embodiments, the ssRNAi compound comprises one or more linkages between adjacent nucleotides other than a naturally-occurring phosphodiester linkage. Examples of such linkages include phosphoramide, phosphorothioate, and phosphorodithioate linkages. The ssRNAi compounds may also be chemically modified nucleic acid molecules as taught in U.S. Pat. No. 6,673,661. In other embodiments, the ssRNAi contains a capped strand, as disclosed, for example, by WO 00/63364, filed Apr. 19, 2000. In certain embodiments, the ssRNAi compound consists of 16, 17, 18, 19, 20, 21, 22, or 23 linked nucleosides.

In certain embodiments, compounds described herein comprise modified oligonucleotides. Certain modified oligonucleotides have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L) such as for amino acids etc. Included in the modified oligonucleotides provided herein are all such possible isomers, including their racemic and optically pure forms, unless specified otherwise. Likewise, all cis- and trans-isomers and tautomeric forms are also included.

Certain Mechanisms

In certain embodiments, compounds described herein comprise or consist of modified oligonucleotides. In certain embodiments, compounds described herein are antisense compounds. In certain embodiments, such antisense compounds comprise oligomeric compounds. In certain embodiments, compounds described herein are capable of hybridizing to a target nucleic acid, resulting in at least one antisense activity. In certain embodiments, compounds described herein selectively affect one or more target nucleic acid. Such selective compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA: DNA duplex. The DNA in such an RNA: DNA duplex need not be unmodified DNA. In certain embodiments, compounds described herein are sufficiently "DNA-like" to elicit RNase H activity. Further, in certain embodiments, one or more non-DNA-like nucleoside in the gap of a gapmer is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

In certain embodiments, hybridization of compounds described herein to a target nucleic acid does not result in recruitment of a protein that cleaves that target nucleic acid. In certain such embodiments, hybridization of the compound to the target nucleic acid results in alteration of splicing of the target nucleic acid. In certain embodiments, hybridization of the compound to a target nucleic acid results in inhibition of a binding interaction between the target nucleic acid and a protein or other nucleic acid. In certain such embodiments, hybridization of the compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or individual.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain such embodiments, the target nucleic acid is selected from: an mRNA and a pre-mRNA, including intronic, exonic and untranslated regions. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target region is an lncRNA.

Human gene sequences that encode lnc05 include, without limitation, the following gene sequences: NR_040064.1 (SEQ ID NO: 1), UCOO1GVD.1 (SEQ ID NO: 2), the complement of NC_000001.11 truncated from nucleotides 200342544 to 200373792 (SEQ ID NO: 3), the complement of NC_000001.11 truncated from nucleotides 200340001 to 200377000 (SEQ ID NO: 4) and the complement of NC_018912.2 truncated from nucleotides 201734377 to 201765595 (SEQ ID NO: 5).

Hybridization

In some embodiments, hybridization occurs between a compound disclosed herein and a lnc05 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Hybridization conditions are sequence-dependent and are determined by the nature and composition of the nucleic acid molecules to be hybridized.

Methods of determining whether a sequence is specifically hybridizable to a target nucleic acid are well known in the art. In certain embodiments, the compounds provided herein are specifically hybridizable with a lnc05 nucleic acid.

Complementarity

An oligonucleotide is said to be complementary to another nucleic acid when the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to adenine (A) and thymine (T), adenine (A) and uracil (U), cytosine (C) and guanine (G), and 5-methyl cytosine (mC) and guanine (G) unless otherwise specified. Complementary oligonucleotides and/or nucleic acids need not have nucleobase complementarity at each nucleoside and may include one or more nucleobase mismatches. An oligonucleotide is fully complementary or 100% complementary when such oligonucleotides have nucleobase matches at each nucleoside without any nucleobase mismatches.

In certain embodiments, compounds described herein comprise or consist of modified oligonucleotides. In certain embodiments, compounds described herein are antisense compounds. In certain embodiments, compounds comprise oligomeric compounds. Non-complementary nucleobases between a compound and a lnc05 nucleic acid may be tolerated provided that the compound remains able to specifically hybridize to a target nucleic acid. Moreover, a compound may hybridize over one or more segments of a lnc05 nucleic acid such that intervening or adjacent segments are not involved in the hybridization event (e.g., a loop structure, mismatch or hairpin structure).

In certain embodiments, the compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a lnc05 nucleic acid, a target region, target segment, or specified portion thereof. Percent complementarity of a compound with a target nucleic acid can be determined using routine methods.

For example, a compound in which 18 of 20 nucleobases of the compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, a compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of a compound with a region of a target nucleic acid can be determined routinely using BLAST programs (basic local alignment search tools) and PowerBLAST programs known in the art (Altschul et al., *J. Mol. Biol.,* 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, compounds described herein, or specified portions thereof, are fully complementary (i.e. 100% complementary) to a target nucleic acid, or specified portion thereof. For example, a compound may be fully complementary to a lnc05 nucleic acid, or a target region, or a target segment or target sequence thereof. As used herein, "fully complementary" means each nucleobase of a compound is capable of precise base pairing with the corresponding nucleobases of a target nucleic acid. For example, a 20 nucleobase compound is fully complementary to a target sequence that is 400 nucleobases long, so long as there is a corresponding 20 nucleobase portion of the target nucleic acid that is fully complementary to the compound. Fully complementary can also be used in reference to a specified portion of the first and/or the second nucleic acid. For example, a 20 nucleobase portion of a 30 nucleobase compound can be "fully complementary" to a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, compounds described herein comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region. In certain embodiments, the mismatch is specifically positioned within an oligonucleotide not having a gapmer motif. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

The location of a non-complementary nucleobase may be at the 5' end or 3' end of the compound. Alternatively, the non-complementary nucleobase or nucleobases may be at an internal position of the compound. When two or more non-complementary nucleobases are present, they may be contiguous (i.e. linked) or non-contiguous. In one embodiment, a non-complementary nucleobase is located in the wing segment of a gapmer oligonucleotide.

In certain embodiments, compounds described herein that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a lnc05 nucleic acid, or specified portion thereof.

In certain embodiments, compounds described herein that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a lnc05 nucleic acid, or specified portion thereof.

In certain embodiments, compounds described herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of a compound. In certain embodiments, the compounds are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 11, 12, 13, 14, 15, 16, 17, 18, 19, 20, or more nucleobase portion of a target segment, or a range defined by any two of these values.

Identity

The compounds provided herein may also have a defined percent identity to a particular nucleotide sequence, SEQ ID NO, or compound represented by a specific Isis number, or portion thereof. In certain embodiments, compounds described herein are antisense compounds or oligomeric compounds. In certain embodiments, compounds described herein are modified oligonucleotides. As used herein, a compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the compounds described herein as well as compounds having non-identical bases relative to the compounds provided herein also are contemplated. The non-identical bases may be adjacent to each other or dispersed throughout the compound. Percent identity of a compound is calculated according to the number of bases that have identical base pairing relative to the sequence to which it is being compared.

In certain embodiments, compounds described herein, or portions thereof, are, or are at least, 70%, 75%, 80%, 85%, 90%, 91%, 92%, 93%, 94%, 95%, 96%, 97%, 98%, 99% or 100% identical to one or more of the compounds or SEQ ID NOs, or a portion thereof, disclosed herein. In certain embodiments, compounds described herein are about 70%, 75%, 80%, 85%, 90%, 91%, 92%, 93%, 94%, 95%, 96%, 97%, 98%, or 99% identical, or any percentage between such values, to a particular nucleotide sequence, SEQ ID NO, or compound represented by a specific Isis number, or portion thereof, in which the compounds comprise an oligonucleotide having one or more mismatched nucleobases. In certain such embodiments, the mismatch is at position 1, 2, 3, 4, 5, 6, 7, 8, 9, 10, 11, or 12 from the 5'-end of the oligonucleotide. In certain such embodiments, the mismatch is at position 2, 3, 4, 5, 6, 7, 8, 9, 10, 11, or 12 from the 3'-end of the oligonucleotide.

In certain embodiments, compounds described herein are antisense compounds. In certain embodiments, a portion of the compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, compounds described herein are oligonucleotides. In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Certain Modified Compounds

In certain embodiments, compounds described herein comprise or consist of oligonucleotides consisting of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Modified Nucleosides

Modified nucleosides comprise a modified sugar moiety or a modified nucleobase or both a modified sugar moiety and a modified nucleobase.

1. Modified Sugar Moieties

In certain embodiments, sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for linearlynon-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl(R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted nucleoside or 2'-non-bicyclic modified nucleoside comprises a sugar moiety comprising a linear 2'-substituent group selected from: F, NH$_2$, N$_3$, OCF$_3$, OCH$_3$, O(CH$_2$)$_2$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_m$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a linear 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-non-bicyclic modified nucleoside comprises a sugar moiety comprising a linear 2'-substituent group selected from: F, OCH$_3$, and OCH$_2$CH$_2$OCH$_3$.

Nucleosides comprising modified sugar moieties, such as non-bicyclic modified sugar moieties, are referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modifed sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., J. Org. Chem.,2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O-2', wherein each R, R$_a$, and R$_b$, is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$, is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl(C(=O)—H), substituted acyl, CN, sulfonyl(S(=O)$_2$-J$_1$), or sulfoxyl(S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 20017, 129, 8362-8379; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wengel et al., U.S. Pat. No. 7,053,207, Imanishi et al., U.S. Pat. No. 6,268,490, Imanishi et al. U.S. Pat. No. 6,770,748, Imanishi et al., U.S. RE44,779; Wengel et al., U.S. Pat. No. 6,794,499, Wengel et al., U.S. Pat. No. 6,670,461; Wengel et al., U.S. Pat. No. 7,034,133, Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191, Torsten et al., WO 2004/106356, Wengel et al., WO 91999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

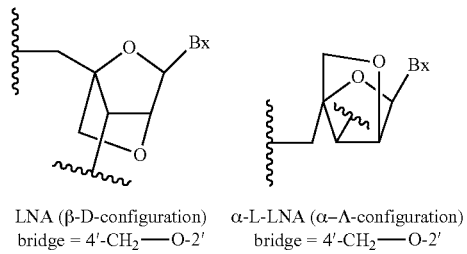

LNA (β-D-configuration)
bridge = 4'-CH$_2$—O-2'

α-L-LNA (α-Λ-configuration)
bridge = 4'-CH$_2$—O-2'

α-L-methyleneoxy (4'-CH$_2$—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see e.g., Leumann, C J. *Bioorg. & Med. Chem.* 2002,10, 841-854), fluoro HNA:

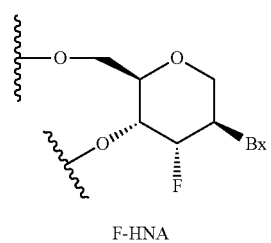

F-HNA ("F-HNA", see e.g., Swayze et al., U.S. Pat. No. 8,088,904; Swayze et al., U.S. Pat. No. 8,440,803; Swayze et al., U.S.; and Swayze et al., U.S. Pat. No. 9,005,906, F-HNA can also be referred to as a F-THP or 3'-fluoro tetrahydropyran), and nucleosides comprising additional modified THP compounds having the formula:

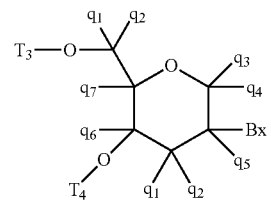

wherein, independently, for each of said modified THP nucleoside: Bx is a nucleobase moiety; $T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

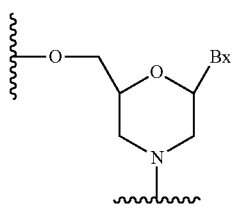

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieites. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to compounds described herein.

In certain embodiments, compounds described herein comprise modified oligonucleotides. In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimi¬dines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, 5-methylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (C≡C—CH3) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp).

Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403, Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

In certain embodiments, compounds targeted to a Inc05 nucleic acid comprise one or more modified nucleobases. In certain embodiments, the modified nucleobase is 5-methylcytosine. In certain embodiments, each cytosine is a 5-methylcytosine.

Modified Internucleoside Linkages

The naturally occurring internucleoside linkage of RNA and DNA is a 3' to 5' phosphodiester linkage. In certain embodiments, compounds described herein having one or more modified, i.e. non-naturally occurring, internucleoside linkages are often selected over compounds having naturally occurring internucleoside linkages because of desirable properties such as, for example, enhanced cellular uptake, enhanced affinity for target nucleic acids, and increased stability in the presence of nucleases.

In certain embodiments, compounds targeted to a Inc05 nucleic acid comprise one or more modified internucleoside linkages. In certain embodiments, the modified internucleoside linkages are phosphorothioate linkages. In certain embodiments, each internucleoside linkage of the compound is a phosphorothioate internucleoside linkage.

In certain embodiments, compounds described herein comprise oligonucleotides. Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates.

Methods of preparation of phosphorous-containing and non-phosphorous-containing linkages are well known.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH2-N($CH_3$)—O—CH2-), thiodiester, thionocarbamate (—O—C(=O)(NH)—S—); siloxane (—O—SiH2-O—); and N,N'-dimethylhydrazine (—CH2-N($CH_3$)—N($CH_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH2-N($CH_3$)—O-5'), amide-3 (3'-CH2-C(=O)—N(H)-5'), amide-4 (3'-CH2-N(H)—C(=O)-5'), formacetal (3'-O—CH2-O-5'), methoxypropyl, and thioformacetal (3'-S—CH2-O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH2 component parts.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosponate linkages. In certain embodiments, oligonucleotides having a gapmer nucleoside motif comprise a linkage motif comprising all phosphorothioate linkages except for one or two methylphosponate linkages. In certain embodiments, one methylphosponate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

B. Certain Motifs

In certain embodiments, compounds described herein comprise oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, compounds described herein comprise oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, a modified oligonucleotide has a fully modified sugar motif wherein each nucleoside of the modified oligonucleotide comprises a modified sugar moiety. In certain embodiments, modified oligonucleotides comprise or consist of a region having a fully modified sugar motif wherein each nucleoside of the region comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified oligonucleotide comprises the same 2'-modification.

2. Certain Nucleobase Motifs

In certain embodiments, compounds described herein comprise oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, compounds described herein comprise oligonucleotides. In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

C. Certain Modified Oligonucleotides

In certain embodiments, compounds described herein comprise modified oligonucleotides. In certain embodiments, the above modifications (sugar, nucleobase, internucleoside linkage) are incorporated into a modified oligonucleotide. In certain embodiments, modified oligonucleotides are characterized by their modification, motifs, and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

Compositions and Methods for Formulating Pharmaceutical Compositions

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

In certain embodiments, the present invention provides pharmaceutical compositions comprising one or more compounds or a salt thereof. In certain embodiments, the compounds are antisense compounds or oligomeric compounds. In certain embodiments, the compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more compound. In certain embodiments, such pharmaceutical composition consists of a sterile saline solution and one or more compound. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises one or more compound and phosphate-buffered saline (PBS). In certain embodiments, a pharmaceutical composition consists of one or more compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

A compound described herein targeted to a lnc05 nucleic acid can be utilized in pharmaceutical compositions by combining the compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising a compound targeted to a lnc05 nucleic acid and a pharmaceutically acceptable diluent. In certain embodiments, the pharmaceutically acceptable diluent is water. In certain embodiments, the compound comprises or consists of a modified oligonucleotide provided herein.

Pharmaceutical compositions comprising compounds provided herein encompass any pharmaceutically acceptable salts, esters, or salts of such esters, or any other oligonucleotide which, upon administration to an individual, including a human, is capable of providing (directly or indirectly) the biologically active metabolite or residue thereof. In certain embodiments, the compounds are antisense compounds or oligomeric compounds. In certain embodiments, the compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a compound which are cleaved by endogenous nucleases within the body, to form the active compound.

In certain embodiments, the compounds or compositions further comprise a pharmaceutically acceptable carrier or diluent.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Discovery of a Novel Long Non-Coding RNA, lnc05

Deep sequencing was performed on nuclei isolated from embryonic stem cells (ESC) and neural progenitor cells (NPC) derived from these cells to measure RNA expression levels in these cell types and to identify novel long non-coding RNAs that are upregulated in ESC.

Poly(A)-selected RNA was obtained from seven single cell-derived mouse ESC clones in the Castaneous/C57BL/6J hybrid background (Cast/BL6), seven single-cell-derived mouse NPC clones differentiated from Cast/BL6 ESCs in two separate derivations (clones 1-5 from the first derivation, and clones 6-7 from the second derivation), as well as AB2.2 (129S5/SvEvBrd) ESC cells and AB2.2-dervied NPC cells. For AB2.2 clones, RNA was isolated from both the whole-cell and nuclear fractions to estimate nuclear enrichment of a given gene product.

ESC colonies were maintained in cell culture as described in Bergmann, Jan H., et al. ("Regulation of the ESC transcriptome by nuclear long noncoding RNAs." *Genome research* 25.9 (2015): 1336-1341). NPCs were differentiated from ESCs via neurospheres as detailed in Eckersley-Maslin, Mélanie A. et al. ("Random Monoallelic Gene Expression Increases upon Embryonic Stem Cell Differentiation." Developmental cell 28.4 (2014): 351-365). Single ESCs and NPCs were seeded through limiting dilutions in 96 wells and expanded to obtain clonal populations.

For transcriptome analyses, total RNA was isolated using TRIzol reagent (Ambion) according to manufacturer's instructions. Nuclear RNA fractions were obtained by resuspending cells in 2×10$^7$/mL in ice-cold nuclei buffer (10 mM Tris pH 7.6, 10 mM NaCl, 2 mM MgCl2) supplemented with protease inhibitors (Sigma) and anti-RNAse (Ambion). After 10 minutes on ice, an equal volume of nuclei buffer containing 0.5% NP-40 was added for 5 minutes and nuclei were then collected, washed in nuclei buffer+NP-40, and lysed in TRIzol.

Poly(A)+ selected RNA was obtained using the Oligotex kit (Quigen) per manufacturer's instructions. RNA-seq libraries for 76-bp paired-end sequencing on the Illumina GAIIx platform were prepared as described in Parkhomchuk, Dmitri et al. ("Transcriptome Analysis by Strand-Specific Sequencing of Complementary DNA." *Nucleic Acids Research* 37.18 (2009): e123). Sequencing was performed on the Illumina GaIIx platform, per manufacturer's instructions. The deep-sequencing reads were then mapped to the mouse genome using TopHat2 as described Bergmann Jan H., et al, ("Regulation ESC transcriptome by nuclear long noncoding RNAs." *Genome research* 25.9 (2015): 1336-1346) to provide the input for an analysis of the RNA transcriptome. Transcriptome analysis was performed using Cufflinks2 (version 2.1.1; http://cufflinks.cbcb.umd.edu/) using transcript models from GENCODE M3. Expression was then analyzed using the GENGODE M3 annotation.

To allow a comparison of the transcriptome of ESCs and NPCs with other cell types, raw RNAseq data from the ENCODE project (The ENCODE Project Consortium. 2012. An integrated encyclopedia of DNA elements in the human genome. Nature 489: 57-74) corresponding to twenty two different mouse tissues was analyzed in the same way as the RNAseq data obtained from the ESC and NPC populations. A FPKM (Fragments Per Kilobase of transcript per Million mapped reads)-based expression matrix was created including this data and gene-level analysis led to the identification of lnc05 as a non-protein-coding gene specifically upregulated in ESCs and liver tissues. A weighted gene coexpression network analysis, as described in Langfelder and Horvath, 2008, was performed to determine which genes lnc05 correlates with, and it was found to be part of the cell cycle module of gene expression.

Example 2

Expression of the Gene in Various Cell Types

To determine the level of lnc05 RNA expression in various cell lines, RNA was extracted using TRIzol and qRT-PCR was performed using lnc05 specific primers [Forward sequence GGGGCCAAGAAGATGACACG (designated herein as SEQ ID NO: 6), Reverse sequence GGACG-CATGTGGAGGTCAGA (designated herein as SEQ ID NO: 7)]. The cell lines tested were ESC, NPC, a liver Hepatocellular carcinoma (HCC) cell line, HepA1-6, and an immortalized, non-cancerous mouse liver cell line, AML12. As presented in the Table below, expression of lnc05 is greatly increased in both ESC and HCC cells.

TABLE 1

Relative Expression of lnc05 in various cell types

| Cell Type | Expression relative to NPC |
| --- | --- |
| ESC | 4.5 |
| NPC | 1.0 |
| HepA1-6 | 18.6 |
| AML12 | 1.7 |

Example 3

Identification of a Potential Human Lnc05 Orthologue

Genes adjacent to lnc05 in the mouse were queried in the human genome to determine if there is a human orthologue of lnc05. An orthologue was identified, and the order of the gene locus is mapped at LINC00862. Information about the human orthologue is available at the NCBI website (Gene ID 554279).

Example 4

Expression of lnc05 in Liver Cancers

Data from The Cancer Genome Atlas (http://cancergenome.nih.gov/) was accessed via CBioPortal (http://www.cbioportal.org/). Expression levels of the gene LINC00862, corresponding to the human ortholog of lnc05, were examined in 14 different cell types. LINC00862 is upregulated in 10% of liver cancers, 11% of breast cancers, and 14% in cholangiocarcinoma. Expression was also upregulated in lung cancer, melanoma, and ovarian cancer.

To determine the expression levels in various HCC cell lines, RNA extraction was performed using TRIzol and qRT-PCR was performed using lnc05 specific primers as described in example 2. HepG2, Hep3B, and Huh? are HCC cell lines, while MCF-7 is a breast cancer cell line. Values are reported relative to MCF-7.

TABLE 2

Expression of lnc05 in cancer cell lines

| Cell line | Expression |
| --- | --- |
| HepG2 | 15.5 |
| Hep3B | 14.0 |
| Huh7 | 21.8 |
| MCF-7 | 1.0 |

Example 5

Antisense Inhibition of lnc05 In Vitro

Antisense oligonucleotides were designed to target human lnc05. These modified oligonucleotides were tested for their effects on lnc05 mRNA levels in HepA1-6 cells in vitro.

The newly designed chimeric antisense oligonucleotides ISIS 689207 (CGTGTCATCTTCTTGGCCCC, designated herein as SEQ ID NO: 8) and ISIS 730744 (TCGTGTCATCTTCTTGGCCC, designated herein as SEQ ID NO: 9) were designed as 5-10-5 MOE. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

Cells were plated at a density of 50,000 cells per well in 6-well plates and were treated with antisense oligonucleotide 24 hours after cell plating. After approximately 24 hours, RNA was isolated from the cells and lnc05 transcript levels were measured by quantitative real-time PCR as in example 2. Results are presented in the table below as fraction inhibition of lnc05 expression relative to cells treated with 1 μM of a scrambled control oligonucleotide.

TABLE 3

Inhibition of Lnc05 expression in HepA1-6 cells

| | Concentration (μM) | Relative Expression |
|---|---|---|
| Scrambled ASO | 1 | 1.0 |
| | 5 | 1.0 |
| ISIS 689207 | 1 | 0.7 |
| | 2.5 | 0.5 |
| | 5 | 0.5 |

To determine a time course of inhibition and to see if the knockdown of lnc05 affects the expression of the cell-cycle marker of proliferation protein mKi67, cells were treated with antisense oligonucleotide 24 hours after plating and then processed at different time points to isolate RNA as described in example 1. Quantitative real-time PCR was used to assess the levels of lnc05 RNA and the levels of mKi67 RNA.

TABLE 4

Time course of relative expression levels in HepA1-6 cells after antisense inhibition of lnc05

| Time | lnc05 | mKi67 |
|---|---|---|
| 0 h | 1.00 | 1.0 |
| 3 h | 1.03 | 0.9 |
| 6 h | 0.95 | 0.9 |
| 12 h | 0.85 | 1.0 |
| 24 h | 0.57 | 1.0 |
| 48 h | 0.25 | 0.3 |

To assess if the knockdown of lnc05 affects cell proliferation in HepA1-6 cells, a colony formation assay was performed. Cells were seeded at a density of 200 cells per well in a 6 well plate and antisense oligonucleotides were added at a concentration of 2.5 μM each. Cells were cultured for 2 weeks with fresh oligonucleotide added every four days. Colony formation was assessed at the end of the experiment by visual inspection.

TABLE 5

Colony formation in HepA1-6 cells

| Oligo ID | Relative colony formation |
|---|---|
| Scrambled | 1.0 |
| ISIS 689207 | 0.51 |
| ISIS 730744 | 0.46 |

To screen for concentration effects, this assay was repeated with two concentrations of antisense oligonucleotide targeting lnc05. The results are presented in the table below.

TABLE 6

| Oligo ID | Oligo Concentration (μM) | Relative colony formation |
|---|---|---|
| Scrambled ASO | 1 | 1.0 |
| | 2.5 | 1.0 |
| ISIS 689207 | 1 | 0.8 |
| | 2.5 | 0.5 |
| ISIS 730744 | 1 | 0.9 |
| | 2.5 | 0.4 |

Example 6

Expression of LINC00862 in Human Normal Liver, Cirrhotic Liver, and Hepatocellular Carcinoma To determine the levels of LINC00862, 80 human samples were accessed from the Biobank in the University of Navarra. Liver samples from healthy patients correspond to individuals with normal or minimal changes in the liver; samples were collected at surgery of digestive tumors or from percutaneous liver biopsy performed because of mild alterations of liver function. Liver samples from patients with cirrhosis, and samples from paired T/NT tissues (HCC tumors (T) and the adjacent non tumoral (NT) cirrhotic liver) were obtained from patients undergoing partial hepatectomy and/or liver transplantation. The results are presented in the table below. Values are reported relative to control

TABLE 7

Levels of LINC00862 in human tissue samples

| | Relative expression |
|---|---|
| Control | 1.0 |
| Cirrhosis | 4.1 |
| HCC | 1.7 |

What is claimed is:

1. A method of treating cancer in an individual having cancer comprising administering a compound comprising a modified oligonucleotide having a nucleobase sequence complementary to a lnc05 nucleic acid to the individual, thereby treating the cancer in the individual.

2. The method of claim 1, wherein the compound is single-stranded.

3. The method of claim 1, wherein the compound is double-stranded.

4. The method of claim 1, wherein the modified oligonucleotide is 12 to 30 linked nucleosides in length.

5. The method of claim 1, wherein the modified oligonucleotide comprises at least one modified internucleoside linkage, at least one modified sugar moiety, or at least one modified nucleobase.

6. The method of claim 5, wherein the at least one modified internucleoside linkage is a phosphorothioate internucleoside linkage, the at least one modified sugar is a bicyclic sugar or 2'-O-methyoxyethyl, and the at least one modified nucleobase is a 5-methylcytosine.

7. The method of claim 5, wherein at least one modified sugar comprises a 4'-CH(CH3)-O-2' bridge or a 4'-(CH2)n-O-2' bridge, wherein n is 1 or 2.

8. The method of claim 1, wherein the modified oligonucleotide comprises:
   a gap segment consisting of linked deoxynucleosides;
   a 5' wing segment consisting of linked nucleosides;
   a 3' wing segment consisting of linked nucleosides;
   wherein the gap segment is positioned immediately adjacent to and between the 5' wing segment and the 3' wing segment and wherein each nucleoside of each wing segment comprises a modified sugar.

9. The method of claim 8, wherein the modified oligonucleotide consists of 20 linked nucleosides and has a nucleobase sequence consisting of the nucleobase sequence of SEQ ID NO: 8, wherein the modified oligonucleotide comprises:
   a gap segment consisting of 10 linked deoxynucleosides;
   a 5' wing segment consisting of 5 linked nucleosides;
   a 3' wing segment consisting of 5 linked nucleosides;
   wherein the gap segment is positioned immediately adjacent to and between the 5' wing segment and the 3' wing segment, each nucleoside of each wing segment comprises a 2'-O-methoxyethyl nucleoside, each internucleoside linkage of the modified oligonucleotide is a phosphorothioate linkage, and each cytosine of the modified oligonucleotide is a 5-methylcytosine.

10. The method of claim 1, wherein the lnc05 nucleic acid has the sequence of any of SEQ ID NOs: 1-5.

11. The method of claim 10, wherein the modified oligonucleotide is at least 90% complementary to the lnc05 nucleic acid.

12. The method of claim 10, wherein the modified oligonucleotide is at least 95% complementary to the lnc05 nucleic acid.

13. The method of claim 10, wherein the modified oligonucleotide is 100% complementary to the lnc05 nucleic acid.

* * * * *